(12) United States Patent
Wallace et al.

(10) Patent No.: US 8,845,639 B2
(45) Date of Patent: Sep. 30, 2014

(54) TISSUE MODIFICATION DEVICES

(75) Inventors: Michael P. Wallace, Pleasanton, CA (US); Robert Garabedian, Sunnyvale, CA (US); Gregory P. Schmitz, Los Gatos, CA (US); Jeffery L. Bleich, Palo Alto, CA (US); Nestor C. Cantorna, Union City, CA (US); Ronald Leguidleguid, Fremont, CA (US); Roy Leguidleguid, Union City, CA (US); Michael Sheinberg, Diablo, CA (US)

(73) Assignee: Baxano Surgical, Inc., Raleigh, NC (US)

( * ) Notice: Subject to any disclaimer, the term of this patent is extended or adjusted under 35 U.S.C. 154(b) by 41 days.

(21) Appl. No.: 13/007,381

(22) Filed: Jan. 14, 2011

(65) Prior Publication Data

US 2011/0112539 A1    May 12, 2011

Related U.S. Application Data

(63) Continuation of application No. PCT/US2009/050492, filed on Jul. 14, 2009, which is (Continued)

(51) Int. Cl.
| | |
|---|---|
| *A61B 17/00* | (2006.01) |
| *A61B 17/16* | (2006.01) |
| *A61B 17/3207* | (2006.01) |
| *A61B 17/14* | (2006.01) |
| *A61B 19/00* | (2006.01) |
| *A61B 17/32* | (2006.01) |

(52) U.S. Cl.
CPC ....... *A61B 17/1671* (2013.01); *A61B 2017/145* (2013.01); *A61B 2019/5454* (2013.01); *A61B 2017/320004* (2013.01); *A61B 17/320016* (2013.01); *A61B 2019/5425* (2013.01); *A61B 17/14* (2013.01); *A61B 2019/5466* (2013.01); *A61B 2017/00261* (2013.01); *A61B 17/32002* (2013.01); *A61B 2017/32006* (2013.01); *A61B 17/3207* (2013.01); *A61B 2017/32008* (2013.01); *A61B 2017/143* (2013.01)

USPC ............................................... 606/85; 606/82

(58) Field of Classification Search
CPC .................. A61B 17/1671; A61B 17/320016; A61B 17/3207
USPC ............................ 29/81.1, 81.17; 606/82, 85
See application file for complete search history.

(56) References Cited

U.S. PATENT DOCUMENTS

| | | |
|---|---|---|
| 184,804 A | 11/1876 | Stohlmann |
| 289,104 A | 11/1883 | How |

(Continued)

FOREIGN PATENT DOCUMENTS

| | | |
|---|---|---|
| DE | 3209403 A1 | 9/1983 |
| DE | 4036804 A1 | 5/1992 |

(Continued)

OTHER PUBLICATIONS

Arcenio et al.; U.S. Appl. No. 12/980,165 entitled "Systems and Methods for Performing Spinal Fusion", filed Dec. 28, 2010.

(Continued)

*Primary Examiner* — David Bates
(74) *Attorney, Agent, or Firm* — Shay Glenn LLP

(57) ABSTRACT

Described herein are elongate devices for modifying tissue having a plurality of flexibly connected and rungs or links, and methods of using them, including methods of using them to decompress stenotic spinal tissue. These devices may be included as part of a system for modifying tissue. In general, these devices include a plurality of blades positioned on for formed from) rungs that are flexibly connected and may be separated by one or more spacers. The rungs are typically wider than they are long (e.g., rectangular). The rungs may be arranged, ladder like, and may be connected by a flexible connector substrate or between two or more cables. Different sized rungs may be used, or rungs with different cutting properties. In some variations the tissue modification devices may have a non-linear axial shape, or may be converted from a first axial shape to a second axial shape.

19 Claims, 38 Drawing Sheets

Related U.S. Application Data a continuation-in-part of application No. 12/324,147, filed on Nov. 26, 2008, now Pat. No. 8,192,436.

(60) Provisional application No. 61/080,647, filed on Jul. 14, 2008, provisional application No. 61/081,685, filed on Jul. 17, 2008, provisional application No. 61/163,699, filed on Mar. 26, 2009, provisional application No. 61/080,647, filed on Jul. 14, 2008.

(56) References Cited

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 1,967,116 A | 7/1934 | Gerdetz |
| 1,967,117 A | 7/1934 | Gerdetz |
| 2,043,603 A | 6/1936 | Allward |
| 2,106,186 A | 1/1938 | Mulholland |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,599,920 A | 1/1952 | Jakobsson et al. |
| 2,679,839 A | 6/1954 | Metzger et al. |
| 2,704,064 A | 5/1955 | Fizzell |
| 2,752,964 A | 7/1956 | Prusinski |
| 2,773,495 A | 12/1956 | Lefevre |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,214,824 A * | 11/1965 | Brown ............... 29/81.02 |
| 3,297,014 A | 1/1967 | Snow |
| 3,310,082 A | 3/1967 | Tramerye |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,598,101 A | 8/1971 | Hensley |
| 3,624,484 A | 11/1971 | Colyer |
| 3,640,280 A | 2/1972 | Slanker et al. |
| 3,651,844 A | 3/1972 | Barnes |
| 3,661,137 A | 5/1972 | Prowse et al. |
| 3,664,329 A | 5/1972 | Naylor |
| 3,682,162 A | 8/1972 | Colyer |
| 3,699,729 A | 10/1972 | Garvey et al. |
| 3,741,192 A | 6/1973 | Avery |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,884,212 A | 5/1975 | Armstrong et al. |
| 3,956,858 A | 5/1976 | Catlin et al. |
| 3,957,036 A | 5/1976 | Normann |
| 3,958,332 A | 5/1976 | Gates et al. |
| 3,960,518 A | 6/1976 | Hall |
| 3,978,862 A | 9/1976 | Morrison |
| 3,999,294 A | 12/1976 | Shoben |
| 4,015,931 A | 4/1977 | Thakur |
| 4,016,857 A | 4/1977 | Hall |
| 4,031,878 A | 6/1977 | Hall |
| RE29,491 E | 12/1977 | Snow |
| 4,097,246 A | 6/1978 | Olson |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,193,188 A | 3/1980 | Johnson |
| 4,203,444 A | 5/1980 | Bonnell et al. |
| 4,207,897 A | 6/1980 | Lloyd et al. |
| 4,258,763 A | 3/1981 | Figueredo et al. |
| 4,259,276 A | 3/1981 | Rawlings |
| 4,273,169 A | 6/1981 | Baenen |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,674,474 A | 6/1987 | Baril |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,793,232 A | 12/1988 | Villemin et al. |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,856,490 A | 8/1989 | Kawase et al. |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashef |
| 4,907,564 A | 3/1990 | Sowa et al. |
| 4,912,799 A * | 4/1990 | Coleman, Jr. ............... 15/104.04 |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,153 A | 2/1991 | Asbery |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,080,086 A | 1/1992 | Tomlinson et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,216,999 A | 6/1993 | Han |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |

(56) References Cited

U.S. PATENT DOCUMENTS

| | | |
|---|---|---|
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,377,659 A | 1/1995 | Tank et al. |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,462,479 A | 10/1995 | Hajek |
| 5,472,262 A | 12/1995 | Buyens et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,591,170 A | 1/1997 | Spievack et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,749,775 A | 5/1998 | Fish |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Åsum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,928,159 A | 7/1999 | Eggers et al. |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,105,568 A | 8/2000 | Yu |
| 6,106,558 A | 8/2000 | Picha |
| 6,113,534 A | 9/2000 | Koros et al. |
| 6,119,674 A | 9/2000 | Eriksson et al. |
| D432,384 S | 10/2000 | Simons |
| 6,131,558 A | 10/2000 | Weber |
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,178,960 B1 | 1/2001 | Svensson |
| 6,205,360 B1 | 3/2001 | Carter |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,257,223 B1 | 7/2001 | Ghio |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |

(56) References Cited

U.S. PATENT DOCUMENTS

| | | |
|---|---|---|
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,859 B1 | 7/2002 | Foley et al. |
| 6,425,887 B1 | 7/2002 | McGuckin et al. |
| 6,428,486 B2 | 8/2002 | Ritchart et al. |
| 6,436,101 B1 | 8/2002 | Hamada |
| 6,442,848 B1 | 9/2002 | Dean |
| 6,446,621 B1 * | 9/2002 | Svensson .................. 125/21 |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |
| 6,478,805 B1 | 11/2002 | Marino et al. |
| 6,487,439 B1 | 11/2002 | Skladnev et al. |
| 6,488,636 B2 | 12/2002 | Bryan et al. |
| 6,491,646 B1 | 12/2002 | Blackledge |
| 6,500,128 B2 | 12/2002 | Marino |
| 6,500,189 B1 | 12/2002 | Lang et al. |
| 6,512,958 B1 | 1/2003 | Swoyer et al. |
| 6,516,223 B2 | 2/2003 | Hofmann |
| 6,520,907 B1 | 2/2003 | Foley et al. |
| 6,527,786 B1 | 3/2003 | Davis et al. |
| 6,533,749 B1 | 3/2003 | Mitusina et al. |
| 6,535,759 B1 | 3/2003 | Epstein et al. |
| 6,540,742 B1 | 4/2003 | Thomas et al. |
| 6,540,761 B2 | 4/2003 | Houser |
| 6,546,270 B1 | 4/2003 | Goldin et al. |
| 6,558,353 B2 | 5/2003 | Zohmann |
| 6,558,390 B2 | 5/2003 | Cragg |
| 6,562,033 B2 | 5/2003 | Shah et al. |
| 6,564,078 B1 | 5/2003 | Marino et al. |
| 6,564,079 B1 | 5/2003 | Cory et al. |
| 6,564,088 B1 | 5/2003 | Soller et al. |
| 6,569,160 B1 | 5/2003 | Goldin et al. |
| 6,575,979 B1 | 6/2003 | Cragg |
| 6,579,291 B1 | 6/2003 | Keith et al. |
| 6,584,345 B2 | 6/2003 | Govari |
| 6,592,559 B1 | 7/2003 | Pakter et al. |
| 6,595,932 B2 | 7/2003 | Ferrera |
| 6,597,955 B2 | 7/2003 | Panescu et al. |
| 6,606,523 B1 | 8/2003 | Jenkins |
| 6,607,530 B1 | 8/2003 | Carl et al. |
| 6,609,018 B2 | 8/2003 | Cory et al. |
| 6,610,066 B2 | 8/2003 | Dinger et al. |
| 6,620,129 B2 | 9/2003 | Stecker et al. |
| 6,622,731 B2 | 9/2003 | Daniel et al. |
| 6,624,510 B1 | 9/2003 | Chan et al. |
| 6,626,916 B1 | 9/2003 | Yeung et al. |
| 6,632,184 B1 | 10/2003 | Truwit |
| 6,638,233 B2 | 10/2003 | Corvi et al. |
| RE38,335 E | 11/2003 | Aust et al. |
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,685,709 B2 | 2/2004 | Sklar |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,815 B2 | 5/2004 | Ginn |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,764,491 B2 | 7/2004 | Frey et al. |
| 6,772,012 B2 | 8/2004 | Woloszko et al. |
| 6,776,765 B2 | 8/2004 | Soukup et al. |
| 6,786,876 B2 | 9/2004 | Cox |
| 6,788,966 B2 | 9/2004 | Kenan et al. |
| 6,790,210 B1 | 9/2004 | Cragg et al. |
| 6,795,737 B2 | 9/2004 | Gielen et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,881,131 B2 | 4/2005 | Parsells et al. |
| 6,882,879 B2 | 4/2005 | Rock |
| 6,884,220 B2 | 4/2005 | Aviv et al. |
| 6,890,353 B2 | 5/2005 | Cohn et al. |
| 6,895,283 B2 | 5/2005 | Erickson et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,915,794 B2 | 7/2005 | Tommasini |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,953,461 B2 | 10/2005 | McClurken et al. |
| 6,962,587 B2 | 11/2005 | Johnson et al. |
| 6,969,392 B2 | 11/2005 | Gitis et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,069,083 B2 | 6/2006 | Finch et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,089,925 B1 | 8/2006 | Lin et al. |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,169,147 B2 | 1/2007 | Nosel |

(56) References Cited

U.S. PATENT DOCUMENTS

| | | | |
|---|---|---|---|
| 7,172,562 B2 | 2/2007 | McKinley | |
| 7,177,677 B2 | 2/2007 | Kaula et al. | |
| 7,181,289 B2 | 2/2007 | Pflueger et al. | |
| 7,189,240 B1 * | 3/2007 | Dekel | 606/85 |
| 7,192,430 B2 | 3/2007 | Truckai et al. | |
| 7,198,598 B2 | 4/2007 | Smith et al. | |
| 7,198,626 B2 | 4/2007 | Lee et al. | |
| 7,207,949 B2 | 4/2007 | Miles et al. | |
| 7,211,082 B2 | 5/2007 | Hall et al | |
| 7,214,186 B2 | 5/2007 | Ritland | |
| 7,214,197 B2 | 5/2007 | Prass | |
| 7,216,001 B2 | 5/2007 | Hacker et al. | |
| 7,223,278 B2 | 5/2007 | Davison et al. | |
| 7,236,832 B2 | 6/2007 | Hemmerling et al. | |
| 7,238,189 B2 | 7/2007 | Schmieding et al. | |
| 7,239,911 B2 | 7/2007 | Scholz | |
| 7,245,789 B2 | 7/2007 | Bates et al. | |
| 7,270,658 B2 | 9/2007 | Woloszko et al. | |
| 7,270,659 B2 | 9/2007 | Ricart et al. | |
| 7,282,033 B2 | 10/2007 | Urmey | |
| 7,282,061 B2 | 10/2007 | Sharkey et al. | |
| 7,295,881 B2 | 11/2007 | Cohen et al. | |
| 7,309,277 B2 | 12/2007 | Nishio et al. | |
| 7,318,823 B2 | 1/2008 | Sharps et al. | |
| 7,337,005 B2 | 2/2008 | Kim et al. | |
| 7,337,006 B2 | 2/2008 | Kim et al. | |
| 7,367,972 B2 | 5/2008 | Francischelli et al. | |
| 7,373,935 B2 | 5/2008 | Lawler et al. | |
| 7,383,639 B2 | 6/2008 | Malandain | |
| 7,390,330 B2 | 6/2008 | Harp | |
| 7,419,487 B2 | 9/2008 | Johnson et al. | |
| 7,449,019 B2 | 11/2008 | Uchida et al. | |
| 7,452,351 B2 | 11/2008 | Miller et al. | |
| 7,470,236 B1 | 12/2008 | Kelleher et al. | |
| 7,476,226 B2 | 1/2009 | Weikel et al. | |
| 7,494,473 B2 | 2/2009 | Eggers et al. | |
| 7,500,977 B2 | 3/2009 | Assell et al. | |
| 7,503,920 B2 | 3/2009 | Siegal | |
| 7,507,218 B2 | 3/2009 | Aliski et al. | |
| 7,522,953 B2 | 4/2009 | Gharib et al. | |
| 7,553,307 B2 | 6/2009 | Bleich et al. | |
| 7,555,343 B2 | 6/2009 | Bleich | |
| 7,578,819 B2 | 8/2009 | Bleich et al. | |
| 7,617,006 B2 | 11/2009 | Metzler et al. | |
| 7,641,658 B2 | 1/2010 | Shaolian et al. | |
| 7,648,521 B2 | 1/2010 | Hestad | |
| 7,655,026 B2 | 2/2010 | Justis et al. | |
| 7,666,186 B2 | 2/2010 | Harp | |
| 7,666,209 B2 | 2/2010 | Zucherman et al. | |
| 7,738,968 B2 | 6/2010 | Bleich | |
| 7,738,969 B2 | 6/2010 | Bleich | |
| 7,740,631 B2 | 6/2010 | Bleich et al. | |
| 7,857,813 B2 | 12/2010 | Schmitz et al. | |
| 8,303,516 B2 | 11/2012 | Schmitz et al. | |
| 2001/0014806 A1 | 8/2001 | Ellman et al. | |
| 2001/0025192 A1 | 9/2001 | Gerber et al. | |
| 2001/0039419 A1 | 11/2001 | Francischelli et al. | |
| 2002/0022788 A1 | 2/2002 | Corvi et al. | |
| 2002/0029060 A1 | 3/2002 | Hogendijk | |
| 2002/0106681 A1 | 8/2002 | Wexler et al. | |
| 2002/0138091 A1 | 9/2002 | Pflueger | |
| 2002/0165590 A1 | 11/2002 | Crowe et al. | |
| 2002/0183647 A1 | 12/2002 | Gozani et al. | |
| 2003/0015203 A1 | 1/2003 | Makower et al. | |
| 2003/0074037 A1 | 4/2003 | Moore et al. | |
| 2003/0105503 A1 | 6/2003 | Marino | |
| 2003/0113906 A1 | 6/2003 | Sangha et al. | |
| 2003/0130655 A1 | 7/2003 | Woloszko et al. | |
| 2003/0130738 A1 | 7/2003 | Hovda et al. | |
| 2003/0167021 A1 | 9/2003 | Shimm | |
| 2003/0187368 A1 | 10/2003 | Sata et al. | |
| 2003/0188749 A1 | 10/2003 | Nichols et al. | |
| 2003/0212400 A1 | 11/2003 | Bloemer et al. | |
| 2003/0225412 A1 | 12/2003 | Shiraishi | |
| 2003/0225415 A1 | 12/2003 | Richard | |
| 2004/0006379 A1 | 1/2004 | Brett | |
| 2004/0006391 A1 | 1/2004 | Reiley | |
| 2004/0019359 A1 | 1/2004 | Worley et al. | |
| 2004/0030330 A1 | 2/2004 | Brassell et al. | |
| 2004/0049208 A1 | 3/2004 | Hill et al. | |
| 2004/0059260 A1 | 3/2004 | Truwit | |
| 2004/0064058 A1 | 4/2004 | McKay | |
| 2004/0097927 A1 | 5/2004 | Yeung et al. | |
| 2004/0106940 A1 | 6/2004 | Shaolian et al. | |
| 2004/0111084 A1 | 6/2004 | Brett | |
| 2004/0122433 A1 | 6/2004 | Loubens et al. | |
| 2004/0122482 A1 | 6/2004 | Tung et al. | |
| 2004/0127893 A1 | 7/2004 | Hovda | |
| 2004/0143165 A1 | 7/2004 | Alleyne | |
| 2004/0143280 A1 | 7/2004 | Suddaby | |
| 2004/0162609 A1 | 8/2004 | Hossainy et al. | |
| 2004/0167444 A1 | 8/2004 | Laroya et al. | |
| 2004/0167553 A1 | 8/2004 | Simpson et al. | |
| 2004/0181150 A1 | 9/2004 | Evans et al. | |
| 2004/0199084 A1 | 10/2004 | Kelleher et al. | |
| 2004/0199159 A1 | 10/2004 | Lee et al. | |
| 2004/0220576 A1 | 11/2004 | Sklar | |
| 2004/0225233 A1 | 11/2004 | Frankowski et al. | |
| 2004/0260358 A1 | 12/2004 | Vaughan et al. | |
| 2005/0027199 A1 | 2/2005 | Clarke | |
| 2005/0033393 A1 | 2/2005 | Daglow | |
| 2005/0049592 A1 | 3/2005 | Keith et al. | |
| 2005/0149035 A1 | 7/2005 | Pimenta et al. | |
| 2005/0171587 A1 | 8/2005 | Daglow et al. | |
| 2005/0182454 A1 | 8/2005 | Gharib et al. | |
| 2005/0187537 A1 | 8/2005 | Loeb et al. | |
| 2005/0197661 A1 | 9/2005 | Carrison et al. | |
| 2005/0203599 A1 | 9/2005 | Garabedian et al. | |
| 2005/0209610 A1 | 9/2005 | Carrison | |
| 2005/0209617 A1 | 9/2005 | Koven et al. | |
| 2005/0209622 A1 | 9/2005 | Carrison | |
| 2005/0216023 A1 | 9/2005 | Aram et al. | |
| 2005/0222598 A1 | 10/2005 | Ho et al. | |
| 2005/0222647 A1 | 10/2005 | Wahlstrand et al. | |
| 2005/0256423 A1 | 11/2005 | Kirsner | |
| 2005/0261692 A1 | 11/2005 | Carrison et al. | |
| 2005/0267529 A1 | 12/2005 | Crockett et al. | |
| 2005/0277942 A1 | 12/2005 | Kullas et al. | |
| 2005/0283148 A1 | 12/2005 | Janssen et al. | |
| 2005/0283204 A1 | 12/2005 | Buhlmann et al. | |
| 2006/0004369 A1 | 1/2006 | Patel et al. | |
| 2006/0015035 A1 | 1/2006 | Rock | |
| 2006/0025702 A1 | 2/2006 | Sterrantino et al. | |
| 2006/0025703 A1 | 2/2006 | Miles et al. | |
| 2006/0025797 A1 | 2/2006 | Lock et al. | |
| 2006/0030854 A1 | 2/2006 | Haines | |
| 2006/0036211 A1 | 2/2006 | Solsberg et al. | |
| 2006/0036271 A1 | 2/2006 | Schomer et al. | |
| 2006/0036272 A1 | 2/2006 | Solsberg et al. | |
| 2006/0058732 A1 | 3/2006 | Harp | |
| 2006/0064101 A1 | 3/2006 | Arramon | |
| 2006/0079919 A1 | 4/2006 | Harp | |
| 2006/0085048 A1 | 4/2006 | Cory et al. | |
| 2006/0085049 A1 | 4/2006 | Cory et al. | |
| 2006/0089633 A1 | 4/2006 | Bleich et al. | |
| 2006/0089650 A1 | 4/2006 | Nolde | |
| 2006/0089688 A1 | 4/2006 | Panescu | |
| 2006/0095028 A1 | 5/2006 | Bleich | |
| 2006/0095059 A1 | 5/2006 | Bleich et al. | |
| 2006/0100651 A1 | 5/2006 | Bleich | |
| 2006/0122458 A1 | 6/2006 | Bleich | |
| 2006/0122620 A1 | 6/2006 | Kim | |
| 2006/0122653 A1 | 6/2006 | Bradley et al. | |
| 2006/0122654 A1 | 6/2006 | Bradley et al. | |
| 2006/0129201 A1 | 6/2006 | Lee et al. | |
| 2006/0142753 A1 | 6/2006 | Francischelli et al. | |
| 2006/0149278 A1 | 7/2006 | Abdou | |
| 2006/0161189 A1 | 7/2006 | Harp | |
| 2006/0173374 A1 | 8/2006 | Neubardt et al. | |
| 2006/0184175 A1 | 8/2006 | Schomer et al. | |
| 2006/0195107 A1 | 8/2006 | Jones et al. | |
| 2006/0200153 A1 | 9/2006 | Harp | |
| 2006/0200154 A1 | 9/2006 | Harp | |
| 2006/0200155 A1 | 9/2006 | Harp | |

(56) References Cited

U.S. PATENT DOCUMENTS

| | | |
|---|---|---|
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1 | 10/2006 | Bleich et al. |
| 2006/0264952 A1 | 11/2006 | Nelson et al. |
| 2006/0264994 A1 | 11/2006 | Schomer et al. |
| 2006/0271080 A1 | 11/2006 | Suddaby |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123888 A1 | 5/2007 | Bleich et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0213795 A1 | 9/2007 | Bradley et al. |
| 2007/0225703 A1 | 9/2007 | Schmitz et al. |
| 2007/0255162 A1 | 11/2007 | Abboud et al. |
| 2007/0255369 A1 | 11/2007 | Bonde et al. |
| 2007/0260252 A1 | 11/2007 | Schmitz et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0282343 A1 | 12/2007 | Hashimoto et al. |
| 2007/0293782 A1 | 12/2007 | Marino |
| 2007/0299403 A1 | 12/2007 | Crowe et al. |
| 2007/0299459 A1 | 12/2007 | Way et al. |
| 2008/0033465 A1 | 2/2008 | Schmitz et al. |
| 2008/0051812 A1 | 2/2008 | Schmitz et al. |
| 2008/0058820 A1 | 3/2008 | Harp |
| 2008/0058874 A1 | 3/2008 | Westlund et al. |
| 2008/0064945 A1 | 3/2008 | Marino et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0188850 A1 | 8/2008 | Mody et al. |
| 2008/0197024 A1 | 8/2008 | Simpson et al. |
| 2008/0200912 A1 | 8/2008 | Long |
| 2008/0221383 A1 | 9/2008 | Way et al. |
| 2008/0221586 A1 | 9/2008 | Garcia-Bengochea et al. |
| 2008/0255439 A1 | 10/2008 | Tang et al. |
| 2008/0255624 A1 | 10/2008 | Arcenio et al. |
| 2008/0275458 A1 | 11/2008 | Bleich et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0036936 A1 | 2/2009 | Solsberg et al. |
| 2009/0054804 A1 | 2/2009 | Gharib et al. |
| 2009/0054936 A1 | 2/2009 | Eggen et al. |
| 2009/0054941 A1 | 2/2009 | Eggen et al. |
| 2009/0062871 A1 | 3/2009 | Chin et al. |
| 2009/0062872 A1 | 3/2009 | Chin et al. |
| 2009/0069709 A1 | 3/2009 | Schmitz et al. |
| 2009/0082763 A1 | 3/2009 | Quick et al. |
| 2009/0105604 A1 | 4/2009 | Bertagnoli et al. |
| 2009/0105788 A1 | 4/2009 | Bartol et al. |
| 2009/0118709 A1 | 5/2009 | Sand et al. |
| 2009/0124934 A1 | 5/2009 | Rabbitte et al. |
| 2009/0138056 A1 | 5/2009 | Anderson et al. |
| 2009/0143807 A1 | 6/2009 | Sand |
| 2009/0143829 A1 | 6/2009 | Shluzas |
| 2009/0149865 A1 | 6/2009 | Schmitz et al. |
| 2009/0171381 A1 | 7/2009 | Schmitz et al. |
| 2009/0177112 A1 | 7/2009 | Gharib et al. |
| 2009/0177144 A1 | 7/2009 | Masmanidis et al. |
| 2009/0177241 A1 | 7/2009 | Bleich et al. |
| 2009/0182382 A1 | 7/2009 | Justis et al. |
| 2009/0192403 A1 | 7/2009 | Gharib et al. |
| 2009/0204016 A1 | 8/2009 | Gharib et al. |
| 2009/0204119 A1 | 8/2009 | Bleich et al. |
| 2009/0209879 A1 | 8/2009 | Kaula et al. |
| 2009/0216284 A1 | 8/2009 | Chin et al. |
| 2009/0299166 A1 | 12/2009 | Nishida |
| 2010/0004654 A1 | 1/2010 | Schmitz et al. |
| 2010/0010334 A1 | 1/2010 | Bleich et al. |
| 2010/0057087 A1 | 3/2010 | Cha |
| 2010/0094231 A1 | 4/2010 | Bleich et al. |
| 2010/0274250 A1 | 10/2010 | Wallace et al. |
| 2010/0331883 A1 | 12/2010 | Schmitz et al. |
| 2010/0331900 A1 | 12/2010 | Garabedian et al. |
| 2011/0004207 A1 | 1/2011 | Wallace et al. |
| 2011/0046613 A1 | 2/2011 | Schmitz et al. |
| 2011/0190772 A1 | 8/2011 | Saadat et al. |
| 2011/0224709 A1 | 9/2011 | Bleich |
| 2011/0224710 A1 | 9/2011 | Bleich |
| 2012/0016368 A1 | 1/2012 | Bleich et al. |
| 2012/0022538 A1 | 1/2012 | Schmitz et al. |
| 2012/0065639 A1 | 3/2012 | Schmitz et al. |
| 2012/0078255 A1 | 3/2012 | Bleich et al. |
| 2012/0095468 A1 | 4/2012 | Wallace et al. |
| 2012/0123294 A1 | 5/2012 | Sun et al. |
| 2012/0143206 A1 | 6/2012 | Wallace et al. |
| 2012/0184809 A1 | 7/2012 | Bleich et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |
| 2013/0172895 A1 | 7/2013 | Wallace et al. |

FOREIGN PATENT DOCUMENTS

| | | |
|---|---|---|
| DE | 19516999 A1 | 11/1996 |
| EP | 0160625 A2 | 11/1985 |
| EP | 0213434 A1 | 3/1987 |
| EP | 359883 A1 | 3/1990 |
| EP | 0414280 A2 | 2/1991 |
| EP | 0450506 A2 | 10/1991 |
| EP | 1304080 A2 | 4/2003 |
| EP | 1340467 A2 | 9/2003 |

(56) References Cited

FOREIGN PATENT DOCUMENTS

| | | |
|---|---|---|
| EP | 1207794 B1 | 5/2004 |
| EP | 1315463 B1 | 5/2005 |
| EP | 1611851 A1 | 1/2006 |
| EP | 1006885 B1 | 9/2006 |
| EP | 1731249 A1 | 12/2006 |
| FR | 2706309 | 12/1994 |
| GB | 723197 A | 2/1955 |
| GB | 2243094 A | 10/1991 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO-96/22057 | 7/1996 |
| WO | WO96/35539 A1 | 11/1996 |
| WO | WO97/14362 A1 | 4/1997 |
| WO | WO-97/34536 A2 | 9/1997 |
| WO | WO-99/18866 A1 | 4/1999 |
| WO | WO-99/21500 A1 | 5/1999 |
| WO | WO99/55506 A1 | 11/1999 |
| WO | WO-00/67651 A1 | 11/2000 |
| WO | WO-01/08571 A1 | 2/2001 |
| WO | WO-01/62168 A2 | 8/2001 |
| WO | WO-02/07901 A1 | 1/2002 |
| WO | WO-02/34120 A2 | 5/2002 |
| WO | WO-02/076311 A2 | 10/2002 |
| WO | WO03/009960 A1 | 2/2003 |
| WO | WO-03/026482 A2 | 4/2003 |
| WO | WO-03/066147 A1 | 8/2003 |
| WO | WO-2004/002331 A1 | 1/2004 |
| WO | WO-2004/028351 A2 | 4/2004 |
| WO | WO-2004/043272 A1 | 5/2004 |
| WO | WO-20041056267 A1 | 7/2004 |
| WO | WO-2004/078066 A2 | 9/2004 |
| WO | WO-2004/080316 A1 | 9/2004 |
| WO | WO-2004/096080 A2 | 11/2004 |
| WO | WO-2005/009300 A1 | 2/2005 |
| WO | WO-2005/057467 A2 | 6/2005 |
| WO | WO-2005/077282 A1 | 8/2005 |
| WO | WO-2005/089433 A2 | 9/2005 |
| WO | WO-2006/009705 A2 | 1/2006 |
| WO | WO-2006/015302 A1 | 2/2006 |
| WO | WO-2006/017507 A2 | 2/2006 |
| WO | WO-2006/039279 A2 | 4/2006 |
| WO | WO-2006/042206 A2 | 4/2006 |
| WO | WO-2006/044727 A2 | 4/2006 |
| WO | WO-2006/047598 A1 | 5/2006 |
| WO | WO-2006/058079 A3 | 6/2006 |
| WO | WO-2006/058195 A2 | 6/2006 |
| WO | WO-2006/062555 A2 | 6/2006 |
| WO | WO-2006/086241 A2 | 8/2006 |
| WO | WO-2006/099285 A2 | 9/2006 |
| WO | WO-2006/102085 A2 | 9/2006 |
| WO | WO-2007/008709 A2 | 1/2007 |
| WO | WO-2007/021588 A1 | 2/2007 |
| WO | WO-2007/022194 A2 | 2/2007 |
| WO | WO-2007/059343 A2 | 2/2007 |
| WO | WO-2007/067632 A2 | 6/2007 |
| WO | WO-2008/008898 A2 | 1/2008 |
| WO | WO2008/014504 A2 | 1/2008 |
| WO | WO-2008/157513 A1 | 12/2008 |
| WO | WO-2009/012265 A2 | 1/2009 |
| WO | WO-2009/018220 A1 | 2/2009 |
| WO | WO-2009/021116 A2 | 2/2009 |
| WO | WO-2009/036156 A1 | 3/2009 |
| WO | WO-2009/046046 A1 | 4/2009 |
| WO | WO-2009/058566 A1 | 5/2009 |
| WO | WO-2009/151926 A2 | 12/2009 |
| WO | WO-2010/014538 | 4/2010 |

OTHER PUBLICATIONS

Bleich et al.; U.S. Appl. No. 12/984,162 entitled "Devices and Methods for Tissue Access", filed Jan. 4, 2011.
Wallace et al.; U.S. Appl. No. 12/911,537 entitled "Devices and Methods for Treating Tissue", filed Oct. 25, 2010.
Wallace et al.; U.S. Appl. No. 13/007,381 entitled "Tissue Modification Devices", filed Jan. 14, 2011.
Mopec Bone-Cutting tool, Product brochure, Total pp. 4. First accessed Dec. 15, 2005.
Edwards et al; "T-Saw Laminoplasty for the Management of Cervical Spondylotic Myelopathy," SPINE, Lippincott Williams & Wilkins, Inc., vol. 25 (14): 1788-1794. Jan. 1, 2000.
Honl et al; "The Use of Water-Jetting Technology in Prostheses Revision Surgery—First Results of Parameter Studies on Bone and Bone Cement," J. Biomed Mater Res (Applied Biomaterials), John Wiley & Sons, Inc, 53, 6: 781-790. Jan. 1, 2000.
Jun, Byung-Yoon, "Posterior Lumbar Interbody Fusion With Restoration of Lamina and Facet Fusion," SPINE, Lippincott Williams & Wilkins, Inc., vol. 25 No. 8, 917-922. Jan. 1, 2000.
Abdel-Wanis et al., "Tumor growth potential after tumoral and instrumental contamination: an in-vivo comparative study of T-saw, Gigli saw, and scalpel," Journal of orthopaedic science, vol. 6, 424-429. Jan. 1, 2001.
Codman Laminectomy Shaver (a Johnson & Johnson company www.codman.com) catalogue, pp. 416-431, [online] Retrieved from the internet: <URL: http:IIwww.codman.com/PDFs/Catalog_04_R.pdf >. Jan. 1, 2001.
Ellman Int. Disc-FX System Accessories K052241 [online] Retrieved from the Internet: <URL: http://www.ellman.com/ medical/ >. Jan. 1, 2001.
Hara et al., "En Bloc Laminoplasty Performed with Threadwire Saw: Technical Note," Neurosurgery, vol. 48, No. 1, pp. 235-239. Jan. 1, 2001.
Hata et al; "A less invasive surgery for rotator cuff tear: Mini-open repair," Journal of Shoulder and Elbow Surgery, vol. 10 No. 1, 11-16. Jan. 1, 2001.
Integra Ruggles TM Kerrison Rongeurs [online] Retrieved from the internet: <URL: http://www.integra-ls.com/products!? product=22>. Jan. 1, 2001.
US Surgical Kerrison Spinal Rongeur K943116 [online] Retrieved from the internet: <URL: http://www.ussurg.com/uss/index.html>. Jan. 1, 2001.
Sen, Cengiz, Tibia proksimalinde Gigli testeresi ile yapilanperkütan osteotominin güvenilirligi: Kadavra calismasi, Acta orthopaedica et traumatologica turcica, vol. 36, 136-140; (In Russian w/ Eng Summary). Jan. 1, 2002.
Shiraishi T., "A new technique for exposure of the cervical spine laminae," Journal of neurosurgery. Spine, vol. 96(1), 122-126. Jan. 1, 2002.
Shiraishi T., Skip laminectomy—a new treatment for cervical spondylotic myelopathy, preserving bilateral muscular attachments to the spinous processes: a preliminary report, Spine, vol. 2(2), 108-115. Jan. 1, 2002.
Tomita et al., "The Use of the T-Saw for Expansive Midline laminoplasty in the Treatment of Cervical Myelopathy," Orthopedics and Traumatology, No. 3, pp. 169-178, Jan. 1, 2002.
Martin-Benlloch et al., "Expansive Laminoplasty as a Method for Managing Cervical Multilevel Spondylotic Myelopathy," Spine, Lippincott Williams & Wilkins, Inc., vol. 28 No. 7, 680-684. Jan. 1, 2003.
Miyamoto et al., "Kyphectomy Using a Surgical Threadwire (T-saw) for Kyphotic Deformity in a Child With Myelomeningocele," SPINE, Lippincott Williams & Wilkins, Inc., vol. 28 No. 10, E187-E190. Jan. 1, 2003.
Shiraishi et al., "Results of Skip Laminectomy—Minimum 2-Year Follow-up Study Compared With Open-Door Laminoplasty," Spine, Lippincott Williams & Wilkins, Inc., vol. 28 No. 24, 2667-2672. Jan. 1, 2003.
Takada et al., "Unusual Metastasis to the Cauda Equina From Renal Cell Carcinoma," SPINE, Lippincott Williams & Wilkins, Inc., vol. 28 No. 6, E114-E117. Jan. 1, 2003.
Eralp et al., "A comparison of two osteotomy techniques for tibial lengthening," Archives of orthopaedic and trauma surgery, vol. 124:298-300. Jan. 1, 2004.
Skippen et al., "The Chain Saw—Scottish Invention," Scottish Medical Journal, vol. 49(2), 72-75. Jan. 1, 2004.

(56) References Cited

OTHER PUBLICATIONS

Bohinski et al., "Novel use of a threadwire saw for high sacral amputation," Journal of neurosurgery: Spine, vol. 3, 71-78. Jan. 1, 2005.
Nakagiri et al., "Thoracoscopic Rib Resection Using a Gigli Saw," The Annals of Thoracic Surgery, vol. 80, 755-756. Jan. 1, 2005.
Osaka et al., "Clinical significance of a wide excision policy for sacrococcygeal chordoma," J Cancer Res Clin Oncol, Total pp. 6. Jan. 1, 2005.
Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar_ste Jan. 1, 2006.
Park et al; "Cases of the Excision of Carious Joints," John Scrymgeour, Glasgow, Total pp. 6. Jan. 1, 1806.
Pancoast, Joseph, "A Treatise on Operative Surgery," Carey and Hart, Philadelphia, Total pp. 11. Jan. 1, 1844.
Truax, Charles, "The Mechanics of Surgery," Chicago, IL; Total pp. 3. Jan. 1, 1899.
Burrows, Harold, "Surgical instruments and appliances used in operations," Faber and Faber, London, total pp. 4. Jan. 1, 1937.
Wilkins, Robert H, "Neurosurgical Classics," Johnson Reprint Corporation, New York, 377-382. Jan. 1, 1965.
Dammann, Gordon, Pictorial Encyclopedia of Civil War Medical Instruments and Equipment, Pictorial Histories Publishing Company, Missoula, Montana, Total pp. 2. Jan. 1, 1983.
Barer Malvin, "Instrument to Enhance Passage of the Gigli Saw," Journal of Pediatric Orthopedics, Raven Press, New York, 4:762-763. Jan. 1, 1984.
Paley et al., "Percutaneous Osteotomies," Orthopedic Clinics of North America, vol. 22 No. 4, 613-624. Jan. 1, 1991.
Paktiss et al., "Afghan Percutaneous Osteotomy," Journal of Pediatric Orthopaedics, Raven Press Ltd, New York, vol. 13 No. 4, 531-533. Jan. 1, 1993.
Peltier, Leonard Orthopedics: A History and Iconography, Norman Publishing, San Francisco, 1993, Total pp. 3. Jan. 1, 1993.
Rutkow, Ira, "Surgery An Illustrated History," Mosby—Year Book, Inc., St. Louis, Total pp. 4. Jan. 1, 1993.
Goel, Atul, "Neurosurgical forum, Supraorbital Craniotomy," Journal of Neurosurgery, vol. 81, 642-643. Jan. 1, 1994.
Tomita et al., "Total en bloc spondylectomy and circumspinal decompression for solitary spinal metastasis," Paraplegia, 32:36-46. Jan. 1, 1994.
Tomita K. et al., "Total en bloc spondylectomy for solitary spinal metastases," International Orthopaedics (SICOT), 1994, 18: 291-298. Jan. 1, 1994.

Brunori et al., "Celebrating the centennial (1894-1994): Leonardo Gigli and his wire saw," J. Neurosurg, 82:1086-1090. Jan. 1, 1995.
Tomita et al., "The Threadwire Saw: a New Device for Cutting Bone," The Journal of Bone and Joint Surgery, vol. 78, 1915-1917. Jan. 1, 1995.
Baumgart et al., "Indikation and Technik der Knochendurchtrennung," Der Chirurg, vol. 69:1188-1196. (in German with Eng Summary). Jan. 1, 1998.
Stevens et al., "Calvarial Bone Graft Harvest Using the Gigli Saw," Journal of Oral and Maxillofacial Surgery, vol. 56, 798-799. Jan. 1, 1998.
Tomita et al., "Expansive Midline T-Saw Laminoplasty (Modified Spinour Process-Splitting) for the Management of Cervical Myelopathy," SPINE, Lippincott Williams & Wilkins, Inc, 23(1), 32-37. Jan. 1, 1998.
Fujita et al., "Chordoma in the Cervical Spine Managed with En Bloc Excision," SPINE, Lippincott Williams & Wilkins, Inc., 24 (17), 1848-1851. Jan. 1, 1999.
Gore Smoother User Manual, W. L. Gore & Associates, Inc. Flagstaff, AZ, Dec. 1999,Total pages 3. Jan. 1, 1999.
Kawahara et al., "Recapping T-Saw Laminoplasty for Spinal Cord Tumors," SPINE, 1999, vol. 24 No. 13, pp. 1363-1370. Jan. 1, 1999.
Peavy et al., "Comparison of Cortical Bone Ablations by Using Infrared Laser Wavelengths 2.9 to 9.2 µm, Lasers in Surgery and Medicine," vol. 26, 421-434. Jan. 1, 1999.
Zeppelin Laminectomy Rongeur K901372, [online] Retrieved from the internet: <URL: http://www.zeppelin-medical.com/download/instruments.pdf>. Oct. 24, 2006.
Reckling Frederick, "Modified Stethoscope Earpiece Makes Excellent Gigli Saw Guide," J Bone and Joint Surgery Am, 54-A(8), 1787-1788. Dec. 1, 1972.
Schwieger et al., "Abrasive Water Jet Cutting as a New Procedure for Cutting Cancellous Bone—In Vitro Testing in Comparison with the Oscillating Saw," Wiley Interscience, www.interscience,wiley.com, 223-228. Sep. 20, 2004.
Herkowitz, "The Cervical Spine Surgery Atlas", 2004, Lippincott Williams & Wilkins; 2nd Edition; pp. 203-206, & 208; Dec. 2003.
Ohta et al., "Superimposed Mechanomyographic Response at Different Contraction Intensity in Medial Gastrocnemius and Soleus Muscles," International Journal of Sport and Health Science: vol. 5, 63-70, Nov. 2007.
Schmitz et al.; U.S. Appl. No. 13/588,969 entitled "Access and Tissue Modification Systems and Methods," filed Aug. 17, 2012.
Saadat et al.; U.S. Appl. No. 13/913,801 entitled "Powered Tissue Modification Devices and Methods," filed Jun. 10, 2013.

* cited by examiner

FIG. 6
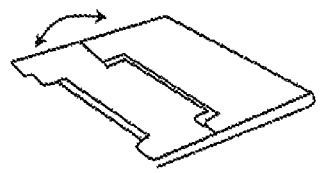
FIG. 7
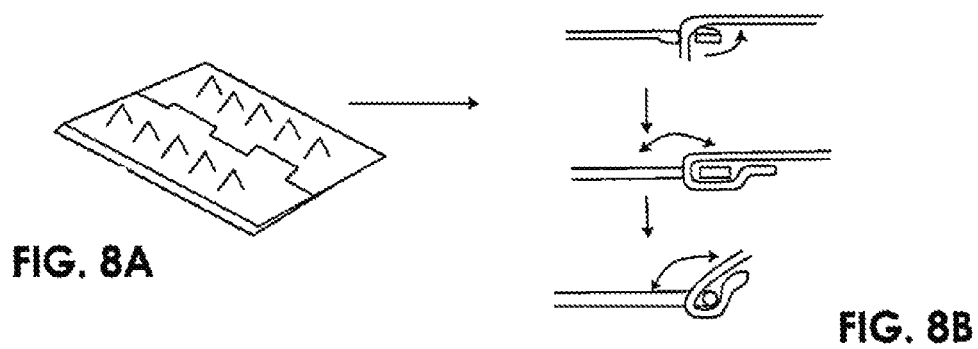
FIG. 8A
FIG. 8B

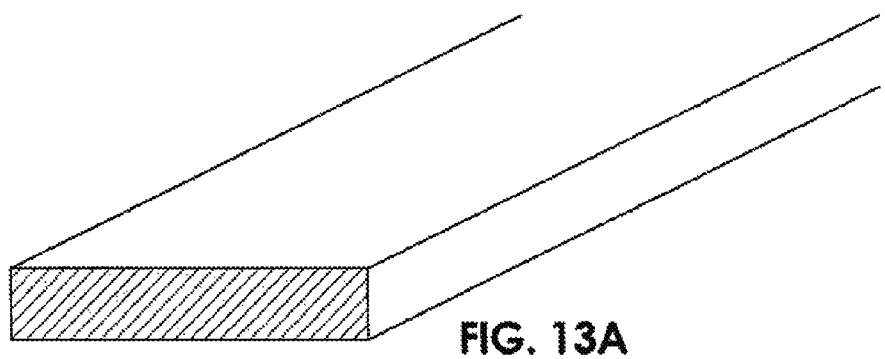
FIG. 13A
FIG. 13B1
FIG. 13B2
FIG. 13B3
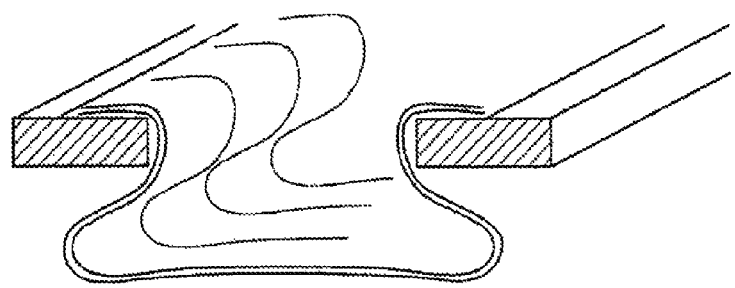
FIG. 14A
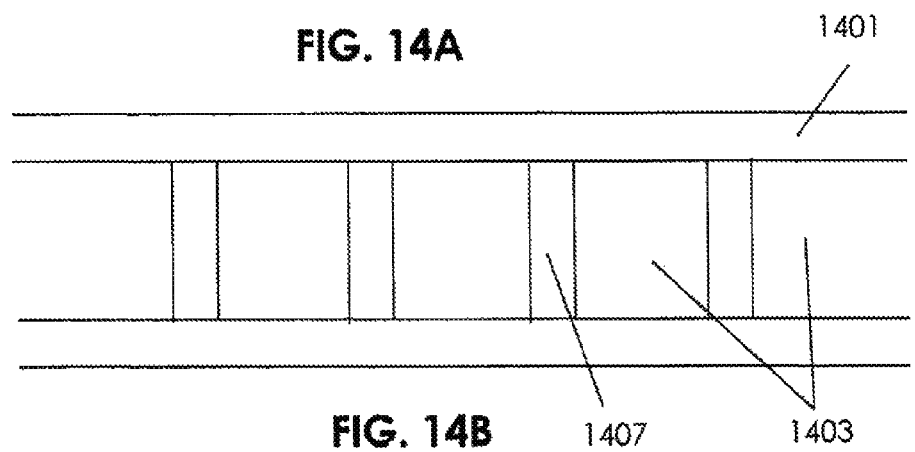
FIG. 14B   1407   1403

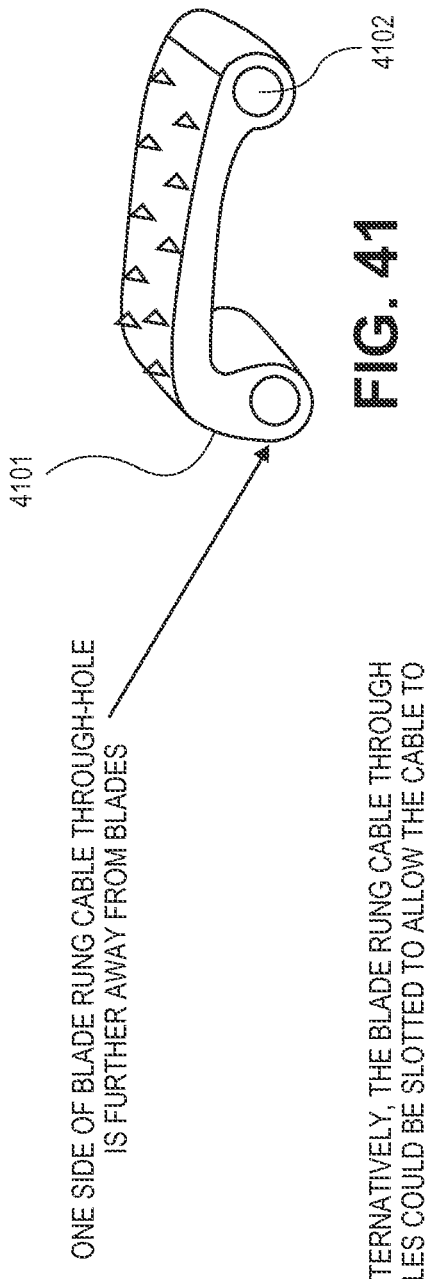
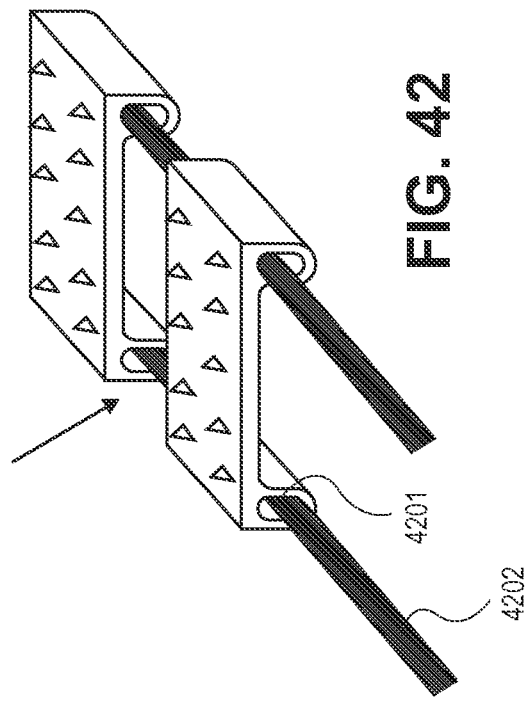
FIG. 41
FIG. 42

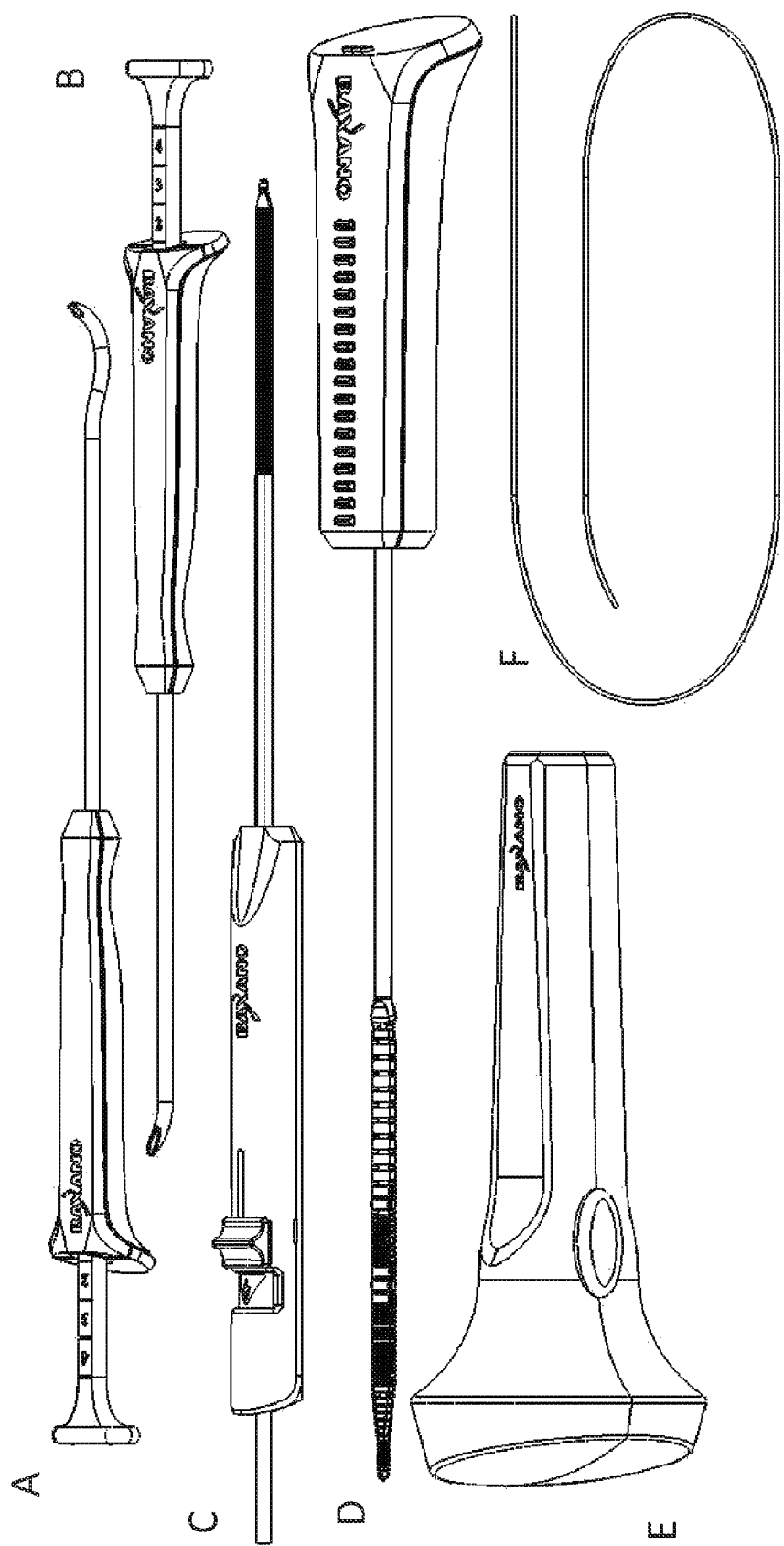
FIG. 43A-F

TISSUE MODIFICATION DEVICES

CROSS-REFERENCE TO RELATED APPLICATIONS

This application is a continuation of International Patent Application No. PCT/US2009/050492, filed on Jul. 14, 2009, published as WO 2010/009093, which claims priority to U.S. Provisional Patent Application No. 61/080,647, filed on Jul. 14, 2008; U.S. Provisional Patent Application No. 61/081, 685, filed on Jul. 17, 2008; and U.S. Provisional Patent Application 61/163,699, filed on Mar. 26, 2009, each of which are herein incorporated by reference in their entirety.

This application is also a continuation-in-part of U.S. patent application Ser. No. 12/324,147, filed on Nov. 26, 2008, published as 2009/0149865, which claims priority to U.S. Provisional Patent Application No. 61/080,647, filed on Jul. 14, 2008 and U.S. Provisional Patent Application No. 61/081,685, filed on Jul. 17, 2008, each of which are herein incorporated by reference in their entirety.

INCORPORATION BY REFERENCE

All publications and patent applications mentioned in this specification are herein incorporated by reference in their entirety as if each individual publication or patent application was specifically and individually indicated to be incorporated by reference.

FIELD OF THE INVENTION

The present invention relates generally to medical/surgical devices and methods. More specifically, the present invention relates to flexible tissue modification devices and methods of modifying tissue using such devices, particularly for treatment of spinal stenosis.

BACKGROUND OF THE INVENTION

A significant number of surgical procedures involve modifying tissue in a patient's body, such as by removing, cutting, shaving, abrading, shrinking, ablating or otherwise modifying tissue. Minimally invasive (or "less invasive") surgical procedures often involve modifying tissue through one or more small incisions or percutaneous access, and thus may be more technically challenging procedures. Some of the challenges of minimally invasive tissue modification procedures include working in a smaller operating field, working with smaller devices, and trying to operate with reduced or even no direct visualization of the tissue (or tissues) being modified. For example, using arthroscopic surgical techniques for repairing joints such as the knee or the shoulder, it may be quite challenging to modify certain tissues to achieve a desired result, due to the required small size of arthroscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% (or more) of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the affected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for modifying target tissue in a spine to help ameliorate or treat spinal stenosis, while inhibiting unwanted damage to non-target tissues. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity resulting from currently available surgical treatments. Furthermore, such techniques may also remove both ligament and bone during spinal stenosis decompression. Such techniques could substantially cut ligament rather than substantially tearing, ripping, or shredding it, and remove ligament without leaving a substantial amount of target ligament present after the procedure. It may also be advantageous to have minimally invasive or less invasive tissue modification devices capable of treating target tissues in parts of the body other than the spine. At least some of these objectives will be met by the present invention.

SUMMARY OF THE INVENTION

Described herein are improved devices for modifying tissue and methods of using them. These devices may be included as part of a system for modifying tissue. In general, these devices include a plurality of blades positioned on (or formed from) rungs that are flexibly connected. The rungs may be rigid, somewhat flat and wider than they are long (e.g., rectangular), or they may have other shapes. The rungs may be arranged, ladder like, to a flexible substrate, or to one or more cable(s). Different sized rungs may be used. The blades (on the rungs) may be arranged toward the side edges of the rungs and/or in a staggered arrangement. Any of the devices described herein may be used as part of a tissue decompression (e.g., spinal decompression) method to modify tissue such as soft tissue (e.g., ligamentum flavum, etc.) and hard tissue (e.g., bone). In particular, these devices may be used as part of a spinal decompression technique within a spinal foramen.

In some variations, a tissue-collection or tissue capture element (e.g., chamber, bag, or the like) may be used to collect the cut or modified tissue.

As mentioned, different shaped, or differently configured rungs may be used. For example, a single device may include two or more different kinds of cutting rungs (e.g., runs including cutting elements). In some variations, the devices may include two or more regions, in which each region has a different type of rung. For example, a rungs adapted for side cutting may be located proximally or distally to rungs adapted for cutting bone, or for cutting material perpendicular to the face of the device.

In any of the variations described herein, the devices may include one or more spacers between individual rungs. The spacers may be rigid or flexible, and may be shaped. Shaping the spacers my help determine profile of the cutting surface, and may allow for tissue collection/capture between the rungs. Variations of spacers are described herein. A spacer may be attached to the same substrate (e.g., cable, mesh, etc.) to which the cutting rungs are attached.

The devices described herein may be used as part of a guide-based access and decompression system, including those previously described in any of the following patent applications and provisional patent applications, each of which is herein incorporated by reference in its entirety: U.S. patent application Ser. No. 11/250,332, titled "DEVICES AND METHODS FOR SELECTIVE SURGICAL REMOVAL OF TISSUE" (filed Oct. 15, 2005), U.S. patent application Ser. No. 11/251,199, titled "DEVICES AND METHODS FOR TISSUE ACCESS" (Oct. 15, 2005), U.S. patent application Ser. No. 11/375,265, titled "METHODS AND APPARATUS FOR TISSUE MODIFICATION" (filed Mar. 13, 2006), U.S. patent application Ser. No. 11/405,848, titled "MECHANICAL TISSUE MODIFICATION DEVICES AND METHODS" (filed Apr. 17, 2006), U.S. patent application Ser. No. 11/429,377, titled "FLEXIBLE TISSUE RASP" (filed May 4, 2006), U.S. patent application Ser. No. 11/538,345, titled "ARTICULATING TISSUE CUTTING DEVICE" (filed Oct. 3, 2006), U.S. patent application Ser. No. 11/687,548, titled "TISSUE REMOVAL WITH AT LEAST PARTIALLY FLEXIBLE DEVICES" (filed Mar. 16, 2007), U.S. patent application Ser. No. 11/687,558, titled "FLEXIBLE TISSUE REMOVAL DEVICES AND METHODS" (filed Mar. 16, 2007), U.S. patent application Ser. No. 11/870,370, titled "PERCUTANEOUS SPINAL STENOSIS TREATMENT" (filed Oct. 10, 2007), and U.S. patent application Ser. No. 12/127,535, titled "GUIDEWIRE EXCHANGE SYSTEMS TO TREAT SPINAL STENOSIS" (filed May 27, 2008).

In particular, the devices described herein may use a guidewire-based system that is configured so that the device may be pulled into position and/or tensioned so as to be urged against a tissue, and thereby modify the tissue. This configuration may be referred to as a bimanual system, since both ends (e.g., the proximal end and the distal end of the device) may be tensioned or pulled to modify the tissue. Tissue may be modified by removal or smoothing of the tissue, and may be performed by pulling the devices described herein through the tissue so that the working surface (e.g., the blades on the rungs) contacts one or more tissue surfaces.

For example, described herein are flexible tissue-modification devices for removing tissue from a patient. These devices may have a flexible elongate body with an axial length, a width and a thickness, wherein the axial length is greater than the width and the width is greater than the thickness. These devices may also include: a connector extending longitudinally along the axial length of the device; a plurality of tissue-cutting rungs that are flexibly connected by the connector, wherein each rung extends at least partially across the width of the body; at least one cutting edge on each of the tissue-cutting rungs; and a plurality of spacers wherein each rung is separated from an adjacent rung by one or more spacers along the connector.

Another variation of a flexible tissue-modification device for removing tissue from a patient includes: a proximal handle; a connector comprising at least two flexible elongate cables, wherein the cables extend substantially adjacent to each other from the proximal end region of the device to the distal end region of the device; a plurality of tissue-cutting rungs extending between the cables; a plurality of spacers wherein one or more spaces separates the tissue-cutting rungs; and at least one cutting edge on the tissue-cutting rungs, wherein the at least one cutting edge is sized and configured to cut soft tissue.

These plurality of tissue-cutting rungs may include rungs of having different configurations and/or sizes. For example, the blades may be placed in different locations or have different shapes. The rungs may also be different shapes or sizes. In some variations the different rungs may be grouped together (to for a first region, a second region, etc.). Different rungs may interact with the tissue differently, leading to different ways of cutting and handling tissue of various types (e.g., soft tissue, bone, etc.).

Any appropriate connector may be used. For example, the connector may be a at least one cable, a mesh or woven material, a hinged joint, or the like. The tissue-cutting rungs and spacers may be threaded on the connector.

Any of these tissue modification devices may also include a guidewire coupler at the distal end of the device. In some variations, the devices include a protective side guard extending along the length of the flexible elongate body.

In any of the variations described herein, the cutting edge may project from the surface of the rung. Any appropriate cutting edge, as described below, may be used.

The devices may also include a tissue collection region in communication with the rung. In some variations, the tissue modification devices include at least one electrode configured for neural detection.

Any appropriate spacer may be used. For example, the spacer may be configured to provide a passage between adjacent rungs. In some variations, the spacer is a ferrule.

Also described herein are flexible tissue-modification device for removing tissue from a patient comprising: a flexible elongate body having a length, a width and a thickness, wherein the length is greater than the width and the width is greater than the thickness; an anterior surface extending proximally and distally across the width of the flexible elongate body; a plurality of cutting edges communicating with the anterior surface; wherein the flexible tissue-modification device is convertible from a first configuration, in which the anterior surface has a first proximal to distal shape, and a second configuration in which the anterior surface has a second proximal to distal shape; and a lock for locking the proximal to distal shape of the anterior surface of the tissue-modification device.

In some variations, a flexible tissue-modification device for removing tissue from a patient, the device includes: a flexible elongate body having a length, a width and a thickness, wherein the length is greater than the width and the width is greater than the thickness; a plurality of rungs that are flexibly connected, wherein each rung extends across the width of the body and forms an anterior surface; at least one cutting edge on two or more of the rungs; wherein the flexible tissue-modification device is convertible from a first configuration, in which the anterior surface has a first proximal to distal shape, and a second configuration, in which the anterior surface has a second proximal to distal shape; and a lock for locking the proximal to distal shape of the anterior surface of the tissue-modification device.

As mentioned, any of these devices may include a connector, such as a cable extending proximally and distally in the device and configured to change the shape of the proximal to distal shape of the anterior surface by applying tension to the cable.

The first proximal to distal shape of the anterior surface may be linear. The second proximal to distal shape of the anterior surface may be curved. For example, the second proximal to distal shape may be a C-shape, an S-shape, etc.

In addition, any of the devices described herein may include a guidewire coupler at the distal end of the flexible elongate body. Any of these devices may also include a handle or handle attachment region in communication with the proximal end of the flexible elongate body.

As mentioned, the anterior surface of the device may include a plurality of flexibly connected rungs, wherein each rung extends across the width of the flexible elongate body.

The device may also include a tissue collection region, such as a pouch, a bag, or the like. The tissue collection region may be expandable.

Also described herein are flexible tissue-modification device for removing tissue from a patient, the device having a flexible elongate body with an axial length, a width and a thickness, wherein the axial length is greater than the width and the width is greater than the thickness, the device comprising: a proximal handle; a connector extending longitudinally along the axial length of the device; a first set of tissue-cutting rungs that are flexibly connected to the connector, wherein the first set of tissue-cutting rungs include at least one cutting edge positioned between the lateral edges of each rung; a second set of tissue-cutting rungs that are flexibly connected to the connector, wherein the second set of tissue-cutting rungs include at least one cutting edge positioned at a lateral edge of the rung; and a guidewire coupler at the distal end.

One aspect of the devices described herein includes a flexible tissue-modification device for removing tissue from a patient. In some embodiments, the device includes a flexible elongate body having an axial length, a width and a thickness. The axial length is greater than the width and the width is greater than the thickness. The flexible elongate body includes a plurality of rungs that are flexibly connected and each rung extends at least partially across the width of the body. The device also includes at least one cutting edge on two or more of the rungs. The cutting edges are sized and configured to cut soft tissue.

In some embodiments, the device for removing tissue from a patient includes at least two flexible elongate cables that extend substantially adjacent to each other from the proximal end of the device to the distal end of the device. The device also includes a plurality of rungs that each extend between the cables. The device also includes at least one cutting edge on two or more of the rungs. The cutting edges are sized and configured to cut soft tissue.

The plurality of rungs may each have rounded edges along their length and may be connected such that a first rung is substantially contacting an adjacent rung along the length of the rung. The cutting edges may project from the surface of the rung. The cutting edge may project from the surface of the rung toward the outer edges of the rung and the cutting edge may be sized and configured to cut a strip of soft tissue and/or to cut an outline of the strip in the soft tissue. The cutting edge may include a serrated edge, a hooked shape, a concave curvature, a rounded convex curvature (e.g. a tombstone shaped edge). The cutting edge may be hatchet shaped or hook shaped. The cutting edge may be sized and configured to engage with soft tissue (e.g. ligamentum flavum) The rung may further include an axle about which the cutting edge may rotate.

In some embodiments, the device further includes at least one tensioning cleat on two or more of the rungs. The tensioning cleat may be sized and configured to tension soft tissue (e.g. ligamentum flavum). In some embodiments, the device further includes at least one raised platform on two or more of the rungs. The raised platform may include a first cutting edge and a second cutting edge. The first cutting edge may be sized and configured to cut soft tissue, and the second cutting edge may be sized and configured to engage with soft tissue (e.g. ligamentum flavum).

In some embodiments, two or more rungs include a base portion and at least two leg portions that define a U-shaped cross section. The leg portions may be flexible and/or have different lengths. The rung may define an opening sized and configured to receive a cable. The opening may be larger than the diameter than the cable. In some embodiments, two or more rungs have a cambered shape. The rung may be sized and configured to engage with a soft tissue such that the soft tissue bunches in the concave portion of the rung and the cutting edge may project from the surface of the concave portion of the rung. A hook shaped cutting edge may project from the surface of the concave portion of the rung, toward the center of the rung.

The rung may be sized and configured to engage with a soft tissue such that the soft tissue is over the convex portion of the rung and the cutting edge may project from the surface of the convex portion of the rung. A hooked shaped cutting edge may project from the surface of the convex portion of the rung, toward the center of the rung.

Another aspect of the devices described herein includes a flexible tissue-modification device for removing tissue from a patient. In some embodiments, the device includes at least two flexible elongate cables. The cables may extend substantially adjacent to each other from the proximal end of the device to the distal end of the device. The device further includes at least one cutting edge on at least one flexible elongate cable. In some embodiments, the cutting edge is crimped onto the cable. In some embodiments, the device further includes a plurality of rungs and each rung extends between the cables. The device may further include at least one cutting edge on two or more of the rungs. In some embodiments, the device further includes a second set of at least two flexible elongate cables. The second set of cables extend substantially in line with the first set of cables, and each rung extends between the second set of cables.

Another aspect of the devices described herein includes a flexible tissue-modification device for removing tissue from a patient. In some embodiments, the device includes a flexible elongate body having an axial length, a width and a thickness. The axial length is greater than the width and the width is greater than the thickness. The device includes a flexible elongate center cable that extends from the proximal end of the device to the distal end of the device and the elongate body includes a plurality of rungs coupled to the cable. The cable is coupled to each rung toward the center of each rung, and each rung extends at least partially across the width of the body. The device also includes at least one cutting edge on two or more of the rungs.

In some embodiments, the device also includes a second set of at least two flexible elongate cables, coupled to each rung at substantially the edge of each rung. The rungs may be sized and configured to rotate about the center cable such that the rungs maintain a substantially constant pressure against tissue across the surface of the rung. The rungs may be sized and configured to rotate about the center cable such that the rungs maintain a substantially constant contact with tissue across the surface of the rung.

BRIEF DESCRIPTION OF THE DRAWINGS

FIG. 6 shows one variation of flexibly connected rungs of a tissue modification device.

FIG. 7 shows another variation of flexibly connected rungs of a tissue modification device.

FIG. 8A shows another variation of flexibly connected rungs of a tissue modification device, and FIG. 8B illustrates the bending of the flexibly connected rungs illustrated in FIG. 8A.

FIG. 13A shows one variation of a substrate of a tissue collection region such as the one shown in FIG. 12A-12C.

FIGS. 13B1-13B3 illustrate one variation of a substrate for a tissue collection region in which the substrate may accordion.

FIG. 14A shows another variation of a substrate for a tissue collection region having expandable regions and semi-rigid regions, and FIG. 14B is a top view of a semi-rigid frame for a tissue collection region such as the one in FIG. 14A.

FIGS. 41-42 illustrate variations of a rung of a tissue modification device.

FIG. 43A-F illustrate one variation of a system including tools for treating spinal stenosis. This system includes two variations of a guidewire positioning probe tool (43A and 43B), a flexible neural localization tool (43C), a tissue modification device (43D), a removable guidewire handle (43E), and a guidewire (43F).

DETAILED DESCRIPTION INVENTION

Figure 1:
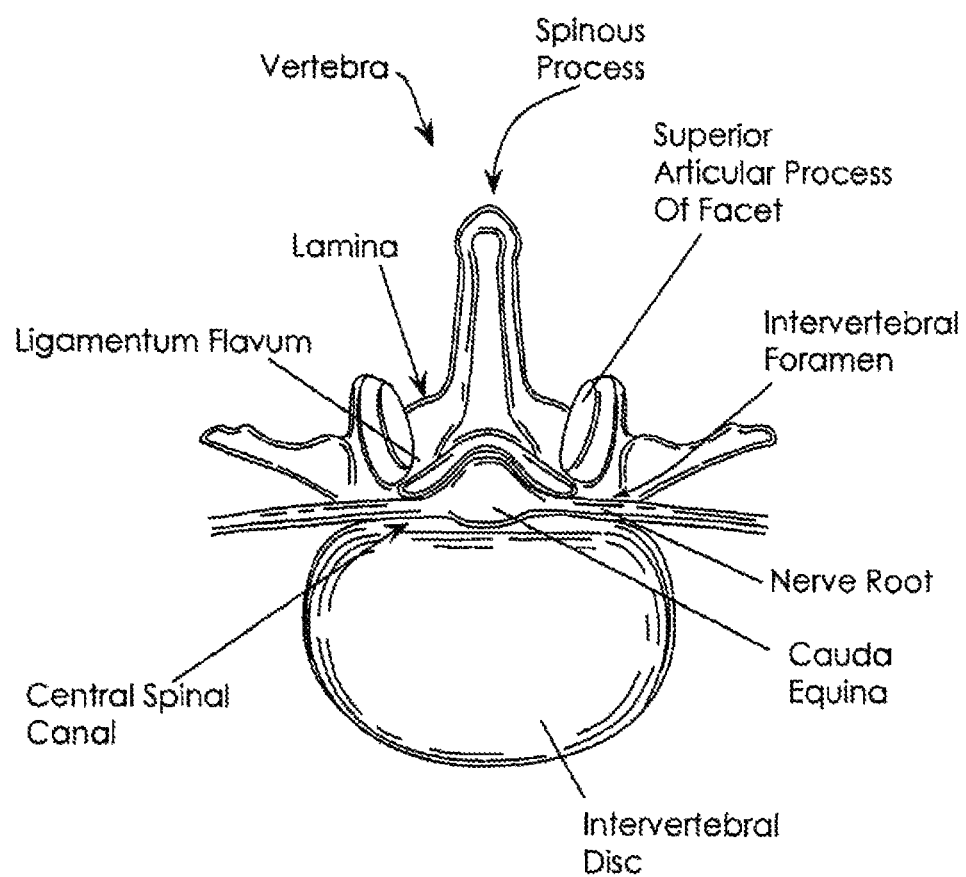
FIG. 1 is a top view of a vertebra with the cauda equina shown in cross section and two nerve roots branching from the cauda equina to exit the central spinal canal and extend through intervertebral foramina on either side of the vertebra.

Various embodiments of tissue modification devices and systems, as well as methods for making and using tissue modification devices and systems, are provided herein. In general, a flexible tissue-modification device as described herein is configured to remove tissue from a patient. In particular, these tissue-modification devices may be configured to decompress spinal stenosis. These devices typically include a flexible elongate body that extends proximally to distally (proximal/distal), and is configured to be inserted into a patient so that it extends around the target tissue, so that it can be bimanually pulled against the target tissue by applying tension to either end of the device. Thus, the device may be extended into, through, and/or around a spinal foramen. The device is flexible in at least one plane. For example, in variations in which the device has an elongated ribbon shape that is long and flat with a width greater than the thickness, the device includes a first major surface (e.g., a front) and a second major surface (a back), and has edges (minor surfaces) between the first and second major surfaces. The first major surface may be referred to as the anterior or front surface and the second major surface may be referred to as the posterior or back surface. The devices described herein may be flexible along the anterior and posterior surfaces, and the anterior or front surface may include one or more cutting edges configured to cut tissue as the anterior surface of the device is urged against a tissue. The posterior surface may be configured to shield or protect non-target tissue.

The tissue modification devices described herein also typically include one or more of the following features: all or a portion of the device maybe formed of flexibly connected rungs or links; the devices may include a tissue capture region having a fixed minimum volume; and the device may be configured so that the major/minor surfaces may have non-linear shapes along their length, or may be stitched between linear and non-linear shapes. A tissue modification device may include one or more of these features in any combination. Each of these features is described and illustrated in greater detail below.

Although much of the following description and accompanying figures generally focuses on surgical procedures in spine, in alternative embodiments, devices, systems and methods of the present invention may be used in any of a number of other anatomical locations in a patient's body. For example, in some embodiments, the flexible tissue modification devices of the present invention may be used in minimally invasive procedures in the shoulder, elbow, wrist, hand, hip, knee, foot, ankle, other joints, or other anatomical locations in the body. Similarly, although some embodiments may be used to remove or otherwise modify ligamentum flavum and/or bone in a spine to treat spinal stenosis, alternative embodiments, other tissues may be modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. In one alternative embodiment, for example, a flexible tissue modification device may be used to incise a transverse carpal ligament in a wrist while inhibiting damage to the median nerve, to perform a minimally invasive carpal tunnel release procedure. Thus, various embodiments described herein may be used to modify any of a number of different tissues, in any of a number of anatomical locations in the body, to treat any of a number of different conditions.

Flexibly Connected Rungs

In some variations, a tissue modification device is formed from a plurality of flexibly connected rungs. As used herein, a rung may also be referred to as a link or crosspiece. A rung may be stiff (e.g., made of a relatively rigid material) or flexible. The rungs may be connected to or may form the anterior (front) major surface. At least some of these rungs include one or more cutting edges, which may be configured as blades. The cutting edges may be formed as part of the rung, or attached to the rung.

Individual rungs may have any appropriate shape. For example, a rung may have a rectangular shape, an oval shape, a trapezoidal shape, or the like. In general, the rung is relatively flat (e.g., having a thickness that is substantially less than the length and width). A rung may be smooth, rough or some combination. Different rungs in the same device may be different shapes and sizes, as illustrated below. A rung may be directly or indirectly connected to adjacent rungs.

Figure 20A:
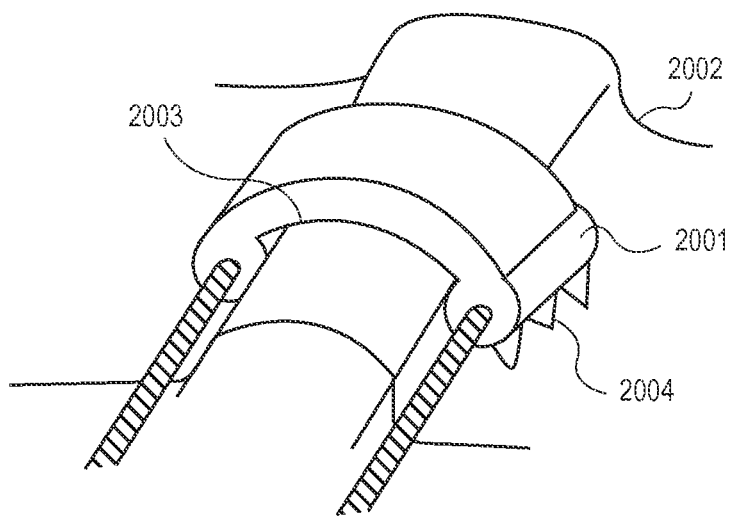
FIGS. 20A-21 illustrate a variation of a rung of the tissue modification device having a curved shape.
Figure 20B:
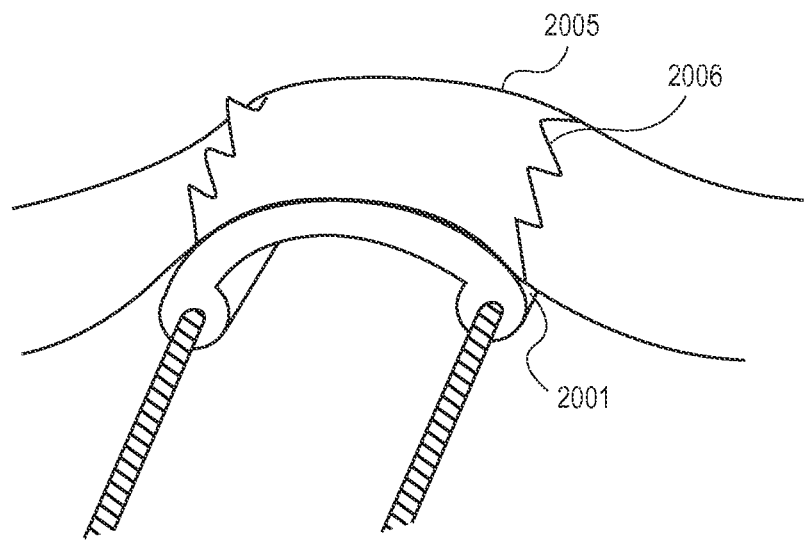
Figure 21:
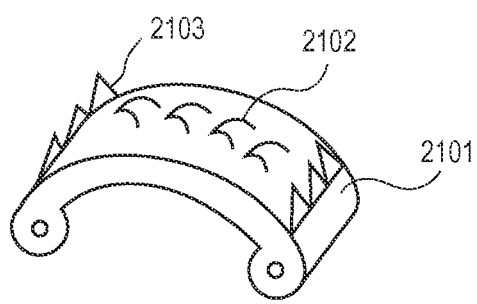

Some of the rungs may be curved. For example, as shown in FIGS. 20A-20B, rung 2001 has a cambered shape. In some embodiments, the cambered rung may be sized and configured to cut a swath of tissue 2002, for example, that may be wider than a swath of tissue cut by a non-curved rung. More specifically, the cambered rung may be sized and configured to cut a swath of ligament or other flexible and/or soft tissues. For example, the flexible and/or soft tissue may be ligamentum flavum in a spine of a patient. In some embodiments, the cambered rung may be sized and configured such that, as shown in FIG. 20A, a concave portion 2003 of the rung contacts the tissue such that the tissue may bunch or collect within the space defined by the concave portion of the cambered rung. Due to the bunching of the tissue, cutting edges 2004 (as described below) coupled to the rung (particularly, cutting edges toward the side edges of the rung) may contact the tissue at points further apart than blades on anon-curved rung may contact the tissue, thereby cutting a wider swath of tissue. In some embodiments, the cambered rung may be sized and configured such that, as shown in FIG. 20B, a convex portion 2005 of the rung contacts the tissue such that the tissue may be pushed apart by or stretched over the convex portion of the cambered rung. Due to the stretching of the tissue, cutting edges 2006 (as described below) coupled to the rung (particularly, cutting edges toward the side edges of the rung) may contact the tissue at points further apart than blades on a non-curved rung may contact the tissue, thereby cutting a wider swath of tissue. In some embodiments, as shown in FIG. 21, a cambered rung 2101 may have cutting edges 2102 coupled to the rung toward the center of the rung in addition to or in alternative to cutting edges 2103 coupled to the rung toward the side edges of the rung. The cutting edges may be hook-shaped as described in more detail below.

Figure 22A:
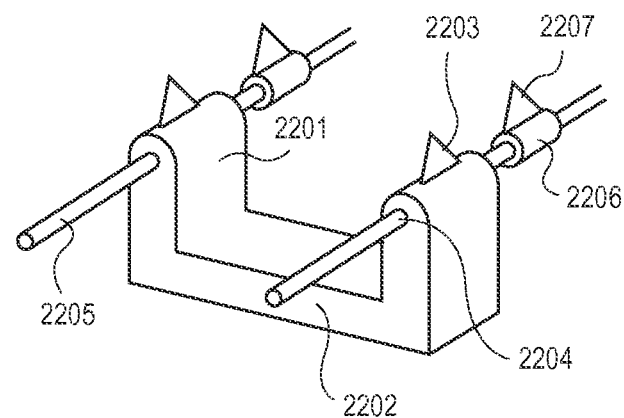
FIGS. 22A-22B illustrate a variation of a rung of the tissue modification device having a U-shaped cross section.
Figure 22B:
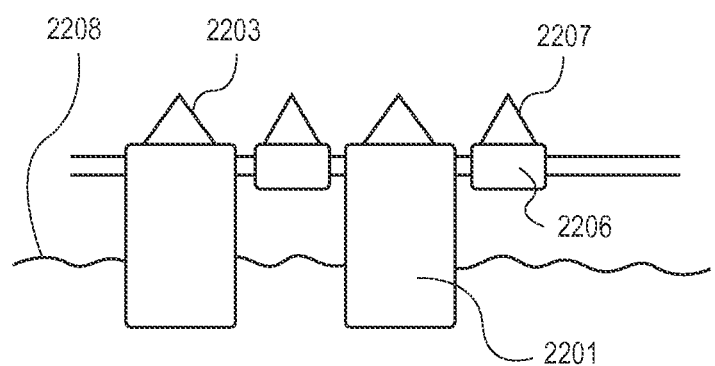
Figure 23A:
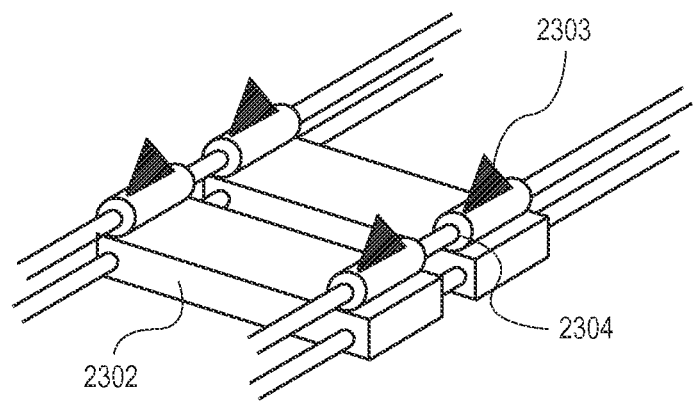
FIGS. 23A-23B illustrate another variation of a rung of the tissue modification device having a U-shaped cross section.
Figure 23B:
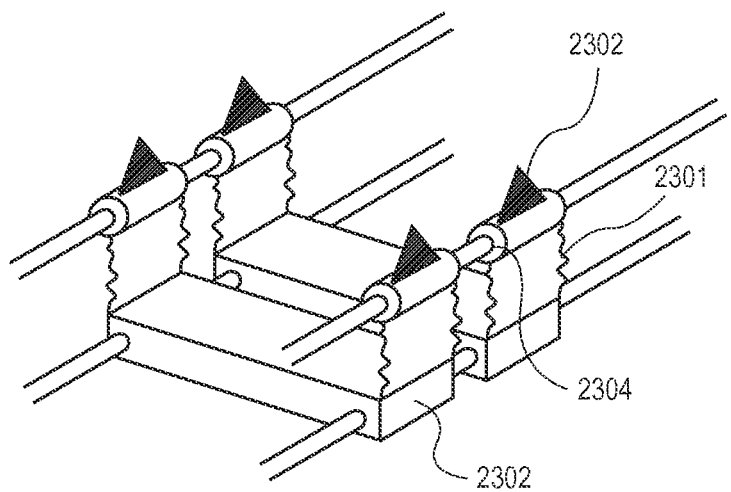

As shown in FIG. 22A, the rung may have a "U" shape (e.g. a rounded or a squared off U-shape). The rung may include two leg portions 2201 and a base portion 2202. The leg portions may be perpendicular to the base portion, or may be configured in any other suitable fashion. The leg portions may be substantially straight, or may have a curved configuration The rung may define an opening 2204 through which a cable 2205 or other connector may be threaded. In some embodiments, the rung may include a cutting edge 2203. The cutting edge may be coupled to the leg portions of the rung above the opening 2204. As shown in FIG. 22B, the U-shaped rungs may function to allow the legs of the rungs to pass through soft tissue 2208, such as ligament, as the cutting edges cut through the tissue, such that the base portion of the rung does not catch on the tissue or otherwise obstruct the cutting of the tissue. As shown, a number of U-shaped rungs may be coupled to a cable to form a modification device. In some embodiments, spacers 2206 may be coupled to the cable between two adjacent U-shaped rungs. The spacers 2206 may include a cutting edge 2207. In some embodiments, the leg portions may be flexible. As shown in FIGS. 23A-B, the leg portion 2301 of the U-shaped rung may be made from an expandable or stretchable material, such that as the cutting edge 2302 cuts through a tissue, the cutting edges and leg portions may extend further into the tissue (FIG. 23B), while the base portion 2302 remains on the surface of the tissue and does not catch on the tissue or otherwise obstruct the cutting of the tissue.

Figure 24A:
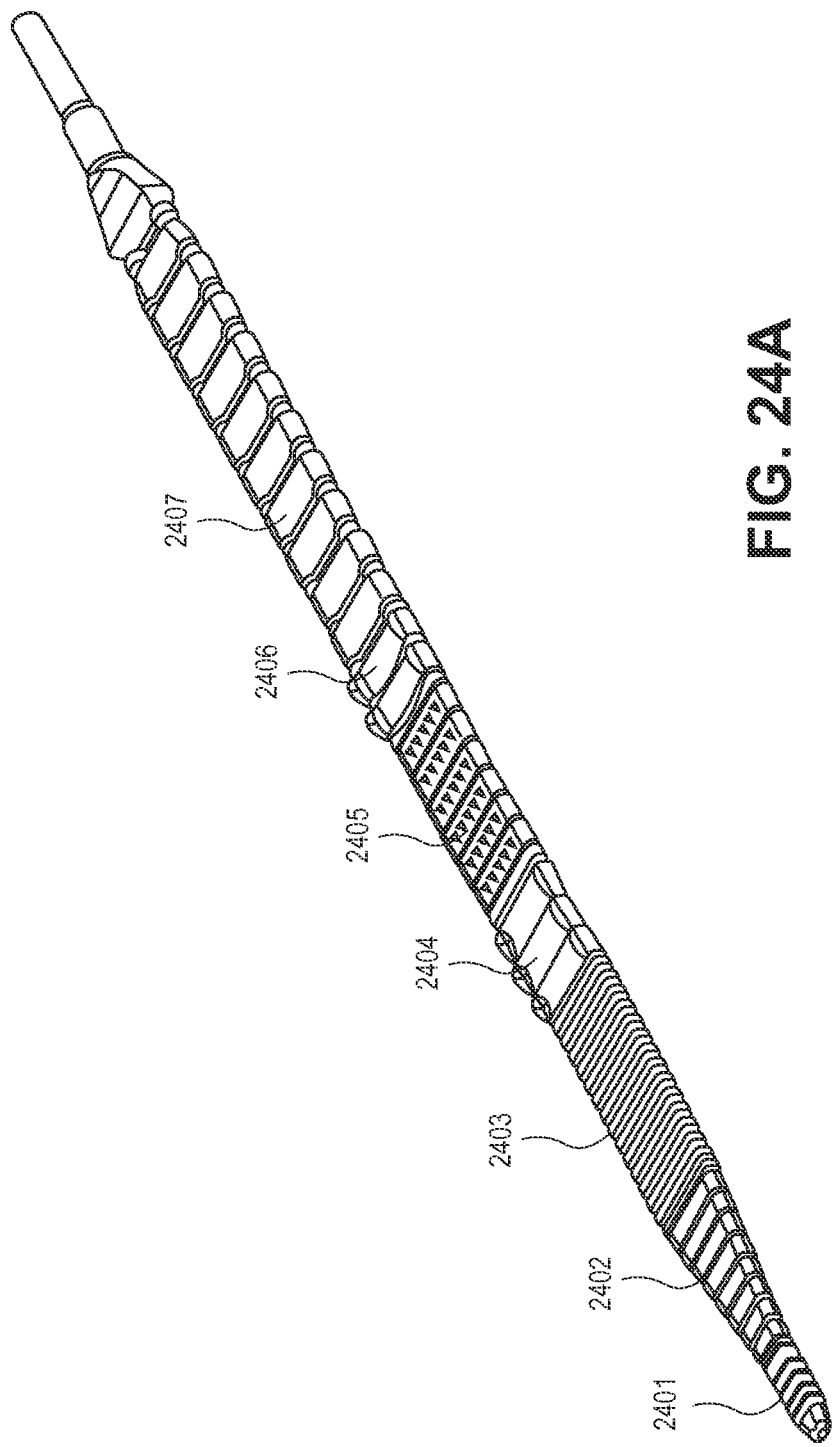
FIGS. 24A-F illustrate a variation of the tissue modification device.
Figure 24B:
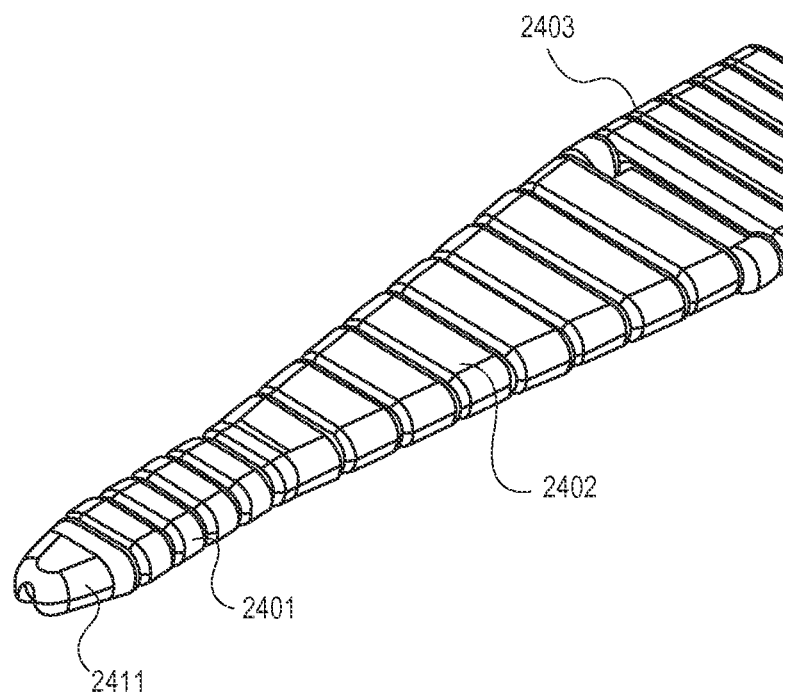
Figure 24C:
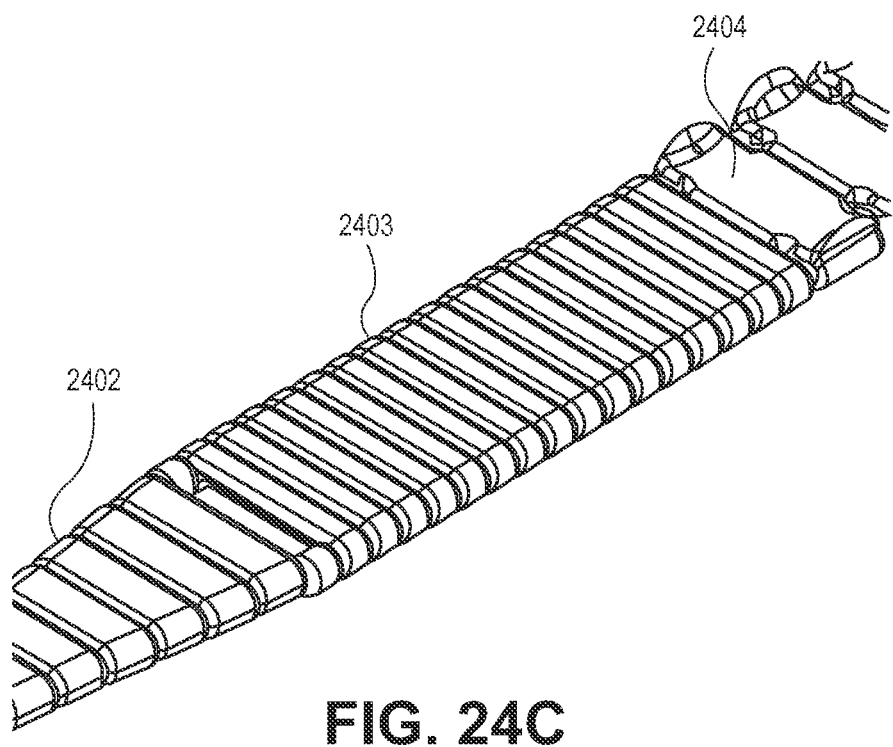

Rungs are flexibly connected to adjacent rungs and/or to another portion of the tissue modification device. A connector, such as a cable, wire, chain, string, sheet, ribbon, mesh, fabric, or the like, may be used to connect adjacent rungs. The connector may be flexible, or stiff. A connector may extend only between adjacent rungs, or it may extend along all or a portion of the length of the device so that multiple rungs may be attached to the same connector. More than one connector may be used to connect adjacent rungs. For example, as shown in FIGS. 24A-F, rungs may be connected between two parallel wires. As shown in FIGS. 24B-C, the rungs may be coupled to two parallel wires such that each rung is touching, or close to touching an adjacent rung, such that there are substantially no gaps between adjacent rungs. In some embodiments, the edges of the rungs are rounded such that, as the device flexes and bends, the adjacent rungs can fold or bend against one another and/or articulate relative to one another. The rungs spaced in this manner (i.e. such that the spacing between the rungs is reduced, and/or there are no gaps between the rungs), may function to reduce the risk of the edges of the rungs from tearing the soft tissue. The rungs spaced in this manner may allow the rungs to move over the soft tissue without tearing it, and may allow the cutting edges, coupled to the rungs, to cut the soft tissue. In some variations, the rungs are directly connected to adjacent rungs by a hinge joint or the like. Combinations of connectors and direct connections between rungs may be used. In some variations, rungs may be separated from each other by a space. The space may be an opening. In some variations, one or more spacers are used to separate adjacent rungs. The spacing between adjacent rungs may be different. In variations including one or more tissue collection regions, the spaces between rungs may provide a passage (or via) between the cutting surface on the anterior-facing surface of the rung, on which a cutting edge may be located (or may extend from) and the tissue collection region.

Figure 2A:
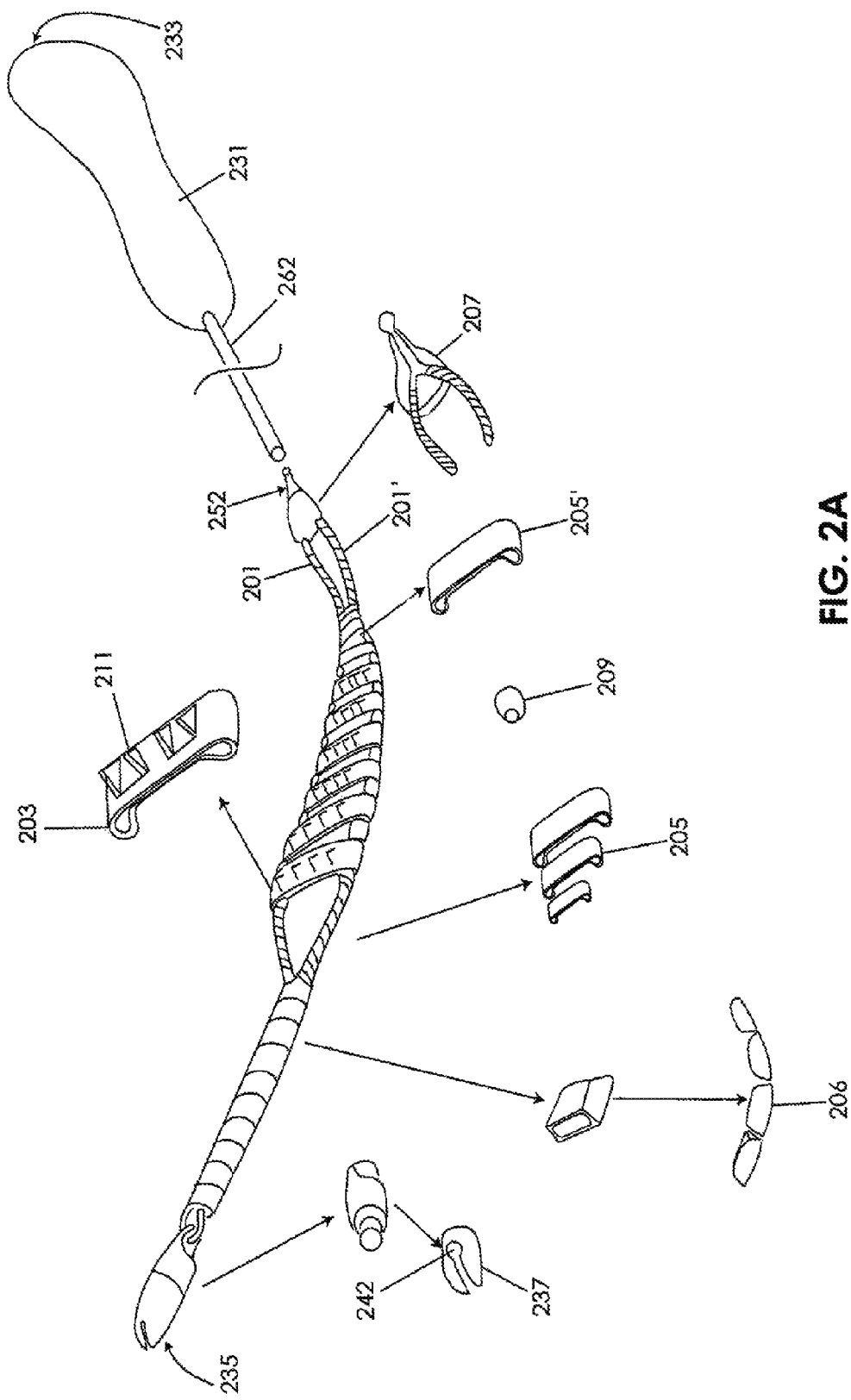
FIG. 2A is a partially exploded, perspective view of a flexible tissue modification device including a plurality of flexibly connected rungs.

For example, FIG. 2A illustrates one variation of a tissue modification device having a plurality of rungs. FIG. 2A is a partially exploded, perspective view illustrating enlargements of various regions. The tissue-modification device shown in FIG. 2A is flexible and includes individual rungs that may articulate relative to each other. This device includes two parallel cables 201, 201' and a plurality of rungs 205, 205', 206, 203 extend between the cables. The cables are the connectors that link adjacent rungs. In this example, the two cables are joined at the proximal 233 and distal 235 regions. In some variations, the cable is joined at the proximal and distal ends, or is formed from a single cable; in some variations the two cables are separate. At least a portion of the cable is flexible. Any appropriate cable may be used, including metal or polymeric cables. Cables may be single-filament or formed of multiple filaments. The portion of the cable towards the distal end of the device, as shown in this example, may be hinged, and the links between distal and proximal sections may be connected in flexible junctions. As mentioned, FIG. 24A illustrates another variation of a tissue modification device having a plurality of rungs. The tissue-modification device shown in FIG. 24A is flexible and includes individual rungs that may articulate relative to each other. This device includes two parallel cables and a plurality of rungs 2401, 2402, 2403, 2404, 2405, 2406, 2407, for example, that extend between the cables.

In some embodiments, the links or rungs 205, 205', 206, 203 spanning the cables have different shapes and sizes. The rungs 203 in the central region each include one or more cutting edges 211 projecting from the anterior (target tissue facing) surface. These cutting rungs 203 may form a tissue modifying region of the device. The cutting edges shown are triangular or pointed, although any appropriate shape may be used. Further, these cutting edges may be oriented in any desired manner; the orientation of the cutting edges may help steer or guide the device as it is urged against a target tissue to cut the tissue. In this example the cutting edges are oriented in parallel with the long axis (the distal/proximal axis) of the device.

Figure 25:
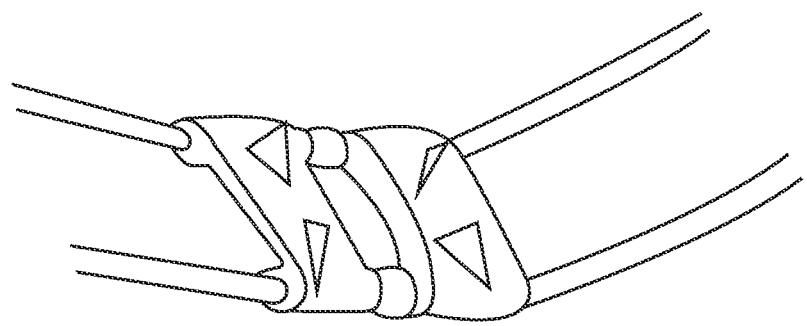
FIG. 25 illustrates a variation of rungs having angles cutting edges.

In some embodiments, the cutting edged may be angled inward toward the longitudinal center of the modification device. In some embodiments, each rung may have cutting edges with the same orientation, or each rung may have a different orientation or an alternating orientation. For example, as shown in FIG. 25, an adjacent pair of rungs may have cutting edges that are angled in opposite directions, such that the cutting edges are oriented or angled toward a center point. In some embodiments, the angled cutting edges may be sized and configured to guide or collect tissue toward the center point. More specifically, in some embodiments, the angled cutting edges may be sized and configured to guide or collect ligament or other flexible and/or soft tissues. For example, in some embodiments, the flexible and/or soft tissue may be ligamentum flavum in a spine of a patient.

Figure 26:
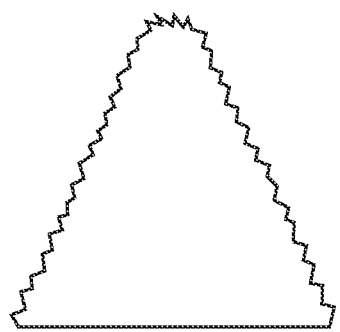
FIGS. 26-32 illustrate variations of cutting edges of a tissue modification device.
Figure 27:
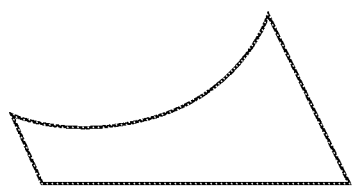
Figure 28:
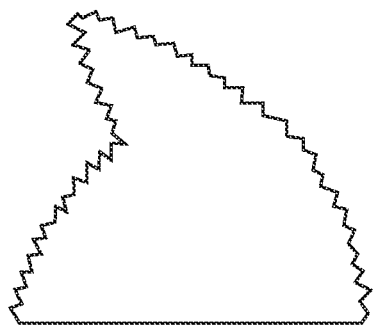
Figure 29:
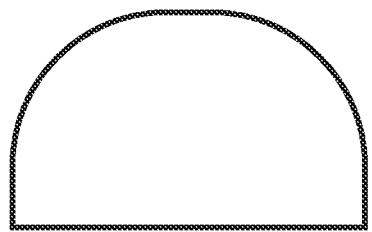

The cutting edges may have one of several suitable shapes and sizes, or any combination of shapes and sizes. In some embodiments, the cutting edges and/or the rungs of the tissue modification device are configured to cut soft tissue, such as ligament. The cutting edges may function to cut the ligament rather than to tear and/or shred it. The cutting edges may have serrated edges (FIG. 26), skate edges (FIG. 27), "shark-tooth" shaped edges (FIG. 28), "tombstone" shaped edges (FIG. 29), hatchet shaped edges (FIG. 30), roller edges (FIG. 31), and/or any other suitable cutting edge configuration or shape. As shown in FIG. 26, in some embodiments, a serrated edge includes several smaller edges around a portion of the cutting edge. As shown in FIG. 32, for example, in some embodiments, the cutting edge may include serrated portions along the sides 3201 of the cutting edge, while the top portion 3202 may not have serrated edges. In FIG. 32, the cutting edge may have a flat top portion, rather than a pointed top portion. As shown in FIG. 27, in some embodiments, a skate edge includes a curved portion of the blade oriented toward the cutting edge of the blade. As shown in FIG. 28, a "shark-tooth" edge may also include a serrated edge, and may have a curved or hooked shape. A "tombstone" shaped edge may include a rounded edge. In some embodiments, the heights of the "tombstone" shaped edge vary from rung to rung.

Figure 24D:
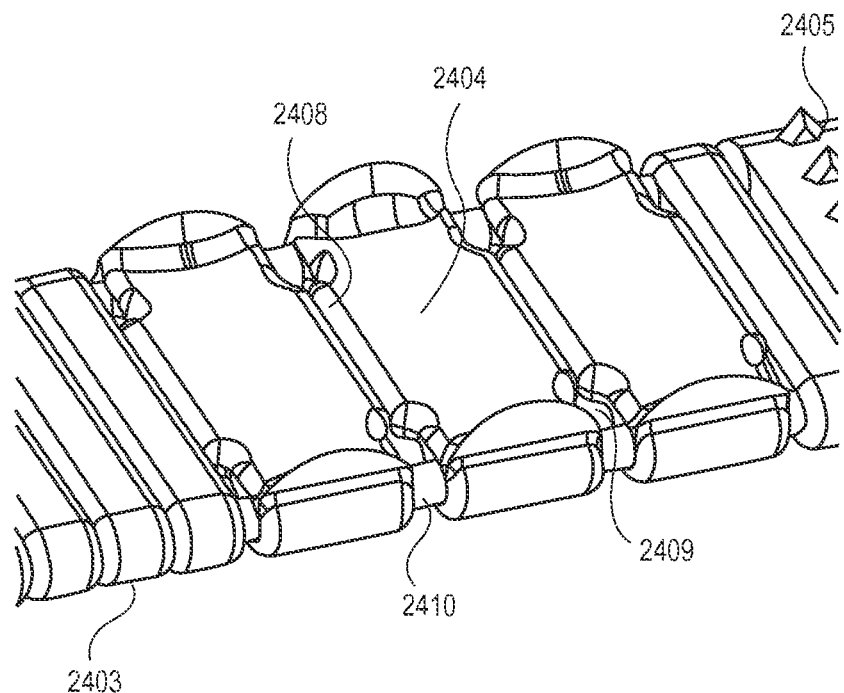
Figure 24E:
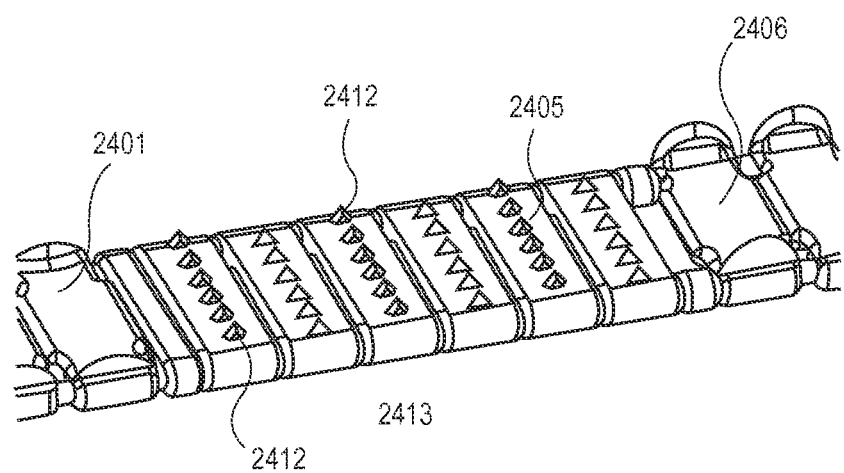

The variation shown in FIGS. 24A-F, includes both rungs having a triangular (or other suitable shaped cutting edge) and rungs having tombstone shaped cutting edges. In some embodiments, the tombstone shaped cutting edges are located toward the outer side or edge of the rung (FIGS. 24D and 24F), while the triangular shaped cutting edges may be located toward the center of the rung (FIG. 24E). For example, the tombstone cutting edges may be sized and configured to cut a flexible and/or soft tissue, including ligament, such as ligamentum flavum in a patient's spine; while the triangular shaped cutting edges may be sized and configured to cut a rigid tissue, including bone, such as the bone of a facet joint, the bone that defines a central canal, and/or the bone that defines a neural foramen of a spine of a patient, including a pedicle. The tombstone cutting edges positioned toward the outer edges of the rung, will cut a swath or strip of soft tissue. By positioning the cutting edge toward the outer edge of the rung, the cutting edge will cut an outline of the swath or strip into the soft tissue. A rung may include fixed bone cutting edges and soft tissue cutting edges that are flexible or foldable, such that they engage with tissue and/or pop up from the rung only as desired. Alternatively, the soft tissue cutting edges may be fixed while the bone cutting edges are movable.

Figure 30:
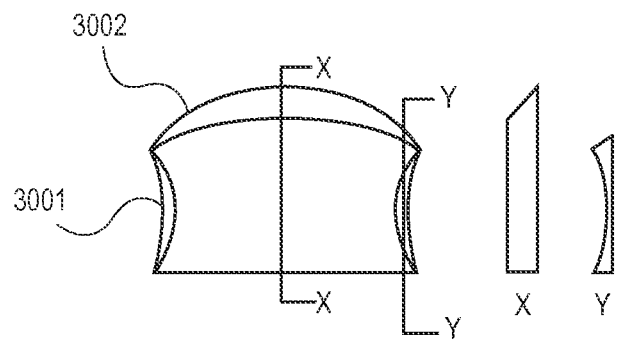
Figure 33:
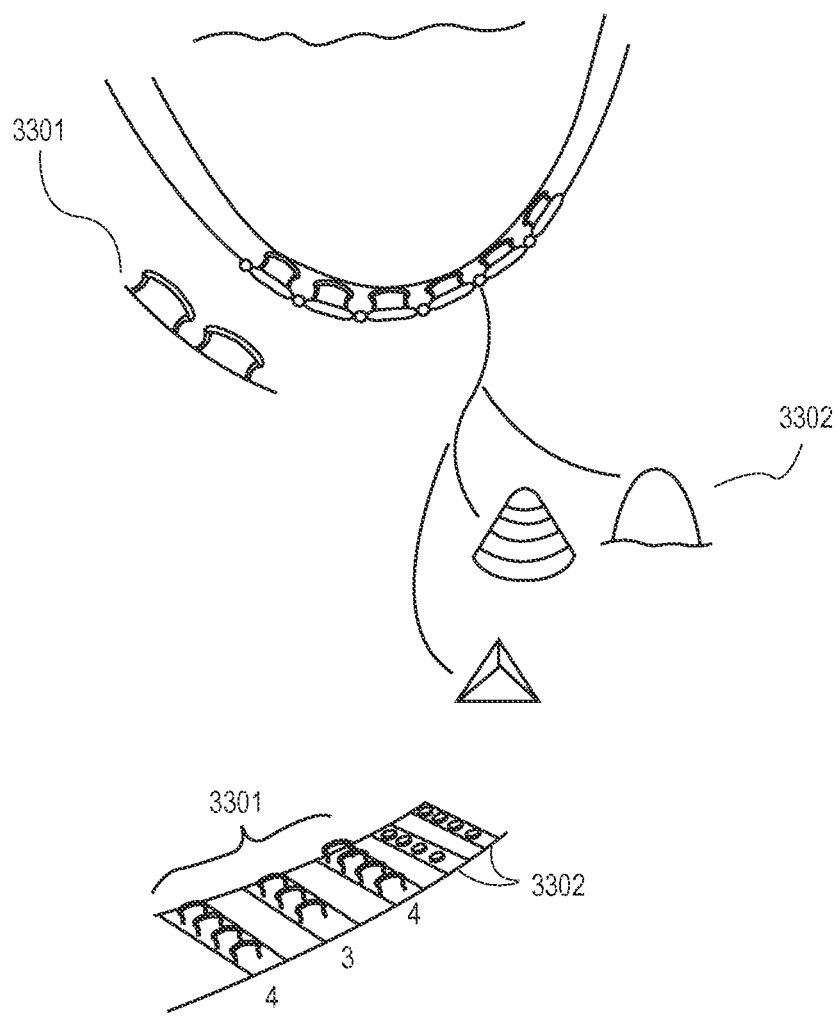
FIGS. 33-34 illustrate variations of cutting edges and tensioning cleats of a tissue modification device.
Figure 34:
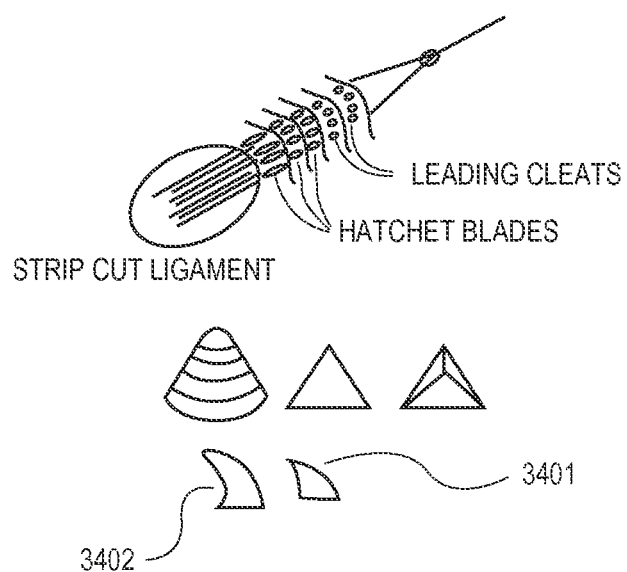

In some embodiments, as shown in FIG. 30, a cutting edge has a hatchet shape. The sides 3001 of the hatchet shaped cutting edge (i.e. leading and trailing edges), may function to hook into and slice a target tissue. More specifically, the sides of the cutting edge may function to hook into and slice a soft tissue, such as a ligament, such as a ligamentum flavum in a spine of a patient. A top surface 3002 of the cutting edge may apply pressure to a tissue and cut it. For example, the top surface may apply pressure to a soft tissue against a bone to cut the soft tissue. The top edge of the blade may also act as a lead when traveling over the bone to avoid ratcheting of the modification device, for example to prevent a portion of the device (such as the rungs) from catching on tissue or otherwise. As shown in FIG. 33, a portion of the rungs of the device may include hatchet shaped cutting edges 3301, while a portion of the rungs may include tensioning cleats 3302 that function to pull and tension a soft tissue. In some embodiments, the cleats are low profile and may have a blunt shape such as a blunt triangular shape or a blunt conical shape. In some embodiments, the cleats are distal to the cutting edges, such that as the device is pulled distally across the target tissue, the cleats are pulled across the tissue first and may function to tension the tissue. The cutting edges may then be pulled across the tissue and cut the tensioned tissue. A modification device may have cutting edges on rungs toward the center of the device, and may have tensioning cleats on rungs toward the proximal and distal portion of the device. In this embodiment, the tissue may be tensioned as the device is pulled both distally and proximally. In FIG. 34, the tension cleats are blunt on one side 3401, and have a sharp, barbed, and/or hooked configuration 3402 on the opposite side, such that the opposite side of the cleat may function to couple to and remove tissue. For example, the cleat may function to tension the tissue as the device is pulled distally, and then may function to couple to and remove the tissue as the device is pulled proximally.

Figure 31:
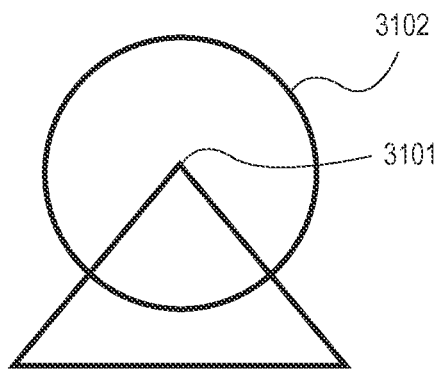
Figure 32:
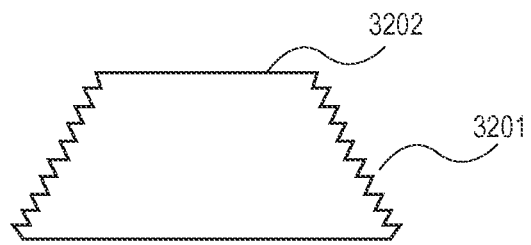

In some embodiments, as shown in FIG. 31, the cutting edges may be roller edges. The cutting edges may have an axle 3101 about which the cutting edge 3102 may rotate. The cutting edge may be circular, but may alternatively have other suitable shapes such as oval or polygonal, (e.g., a star shape). In some embodiments, the axle may be coupled to a rung of the device.

Figure 35:
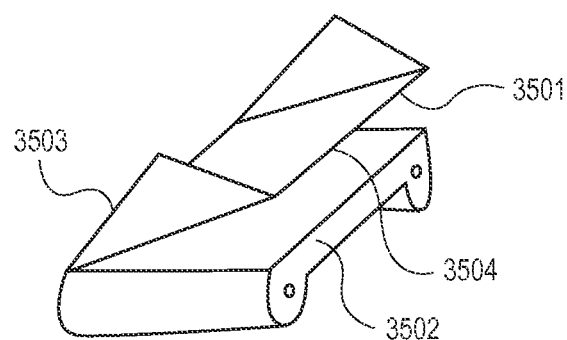
FIG. 35 illustrates a rung of a tissue modification device having a raised platform.

In the embodiments, shown in FIG. 35, the cutting edge includes a raised platform 3501. In some embodiments, the raised platform is coupled to the rung 3502 toward one side of the rung such that it may angle up from the rung, as shown. The raised platform may include a first cutting edge 3503 and a second cutting edge 3504. In some embodiments, the first cutting edge is coupled to the top side of the raised platform, and in some embodiments, the second cutting edge is the exposed edge of the raised platform or may be coupled to the exposed edge or underside of the raised platform. The first cutting edge may be located toward the outer side or edge of the rung.

The first cutting edge may be sized and configured to cut a flexible and/or soft tissue, such as ligament (e.g. ligamentum flavum in a patient's spine). In some embodiments, the second cutting edge is sized and configured to scrape and/or remove tissue soft tissue cut by the first cutting edge. The first cutting edge may be oriented towards the distal end of the tissue modification device, such that, for example, as the device is pulled into a patient, and/or toward a target anatomy, the first cutting edge cuts the target tissue. In some embodiments, the second cutting edge is oriented towards the proximal end of the tissue modification device, such that, for example, as the device is pulled out of a patient, and/or away from target anatomy, the second cutting edge may contact and/or engage with the swath of tissue, and pull the swath of tissue along with the device.

Figure 36:
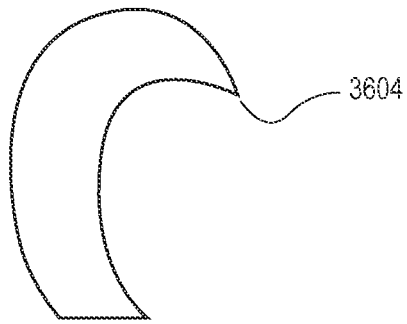
FIG. 36 illustrates a variation of a cutting edge.

As shown in FIG. 36, the cutting edges may be hook-shaped. In some embodiments, the hook-shaped cutting edges are sized and configured to couple to and remove a swath of tissue. More specifically, the hook-shaped cutting edges may be sized and configured to couple to and remove a swath of ligament or other flexible and/or soft tissues. For example, the cutting edges may be configured to remove ligamentum flavum in a patient's spine. In some embodiments, the tips 3601 of the hook-shaped cutting edges are oriented towards the proximal end of the tissue modification device, such that, for example, as the device is pulled out of a patient, or away from target anatomy, the tips of the hooked-shaped cutting edges may couple to the swath of tissue, and pull the swath of tissue along with the device. In some embodiments, the hooked-shaped cutting edges may contact and/or engage with the swath of tissue by piercing the tissue and hooking onto the tissue.

A rung may include hook-shaped cutting edges toward the center of the rung and blade shaped (e.g. triangular or tombstone shaped) cutting edges toward the side or edge of the rung. In some embodiments, the side edges function to cut a swath of tissue, and the hooked-shaped edges function to contact and/or engage with and remove that swath of tissue. In some embodiments, a portion of the rungs may include hooked shaped cutting edges, while a portion of the rungs may have side edges. In some embodiments, the hooked rungs and the blade rungs alternate, while in some embodiments, a portion of the device includes hooked rungs and a second portion of the device includes blade rungs.

In some embodiments, the device further includes a sheath that covers the cutting edges while the device is being introduced into a patient. Once the device has been introduced, and/or once a swath of tissue, for example, has been cut, the sheath may be removed, and the hook-shaped (or other suitable shaped) cutting edges may contact and/or engage with and remove the swath of tissue. In some embodiments, the sheath further functions to remove the cut tissue. The hook-shaped cutting edges may be flexible or foldable such that when they are pulled in a distal direction (toward a target tissue), they do not engage with the tissue, and alternatively, when they are pulled in a proximal direction (away from a target tissue), the hooks engage with the tissue, and may contact and/or engage with and remove the tissue. The hook-shaped cutting edges contacting and/or engaged with tissue may be pulled out of a patient, pulling along the tissue. In some embodiments, once outside of the patient, a user may remove (by suction, irrigation, manually, etc.) the tissue from the hooks. The device may then be reinserted to cut and/or capture additional tissue.

Figure 37:
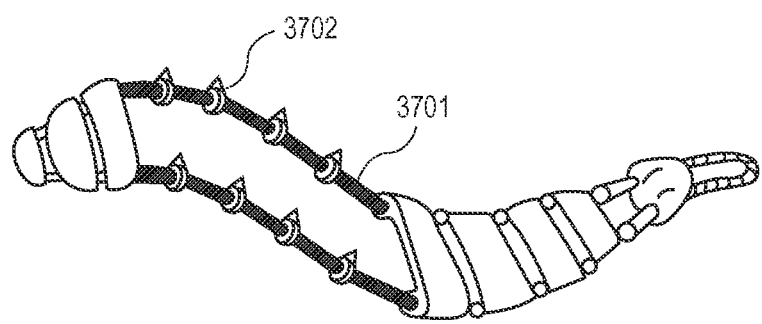
FIGS. 37-38 illustrate variations of a tissue modification device having a cutting cable.
Figure 38:
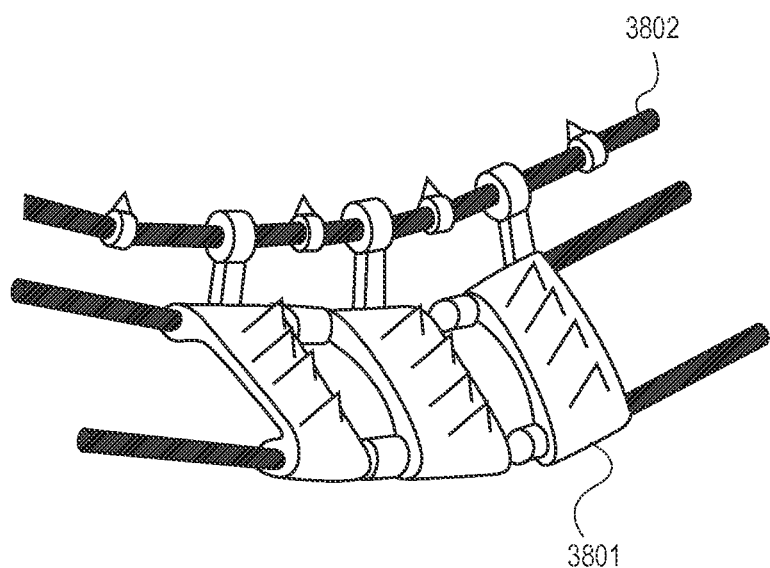

The tissue modification device may include cutting edges directly coupled to a cable, rather than including a rung with a cutting blade. As shown in FIG. 37, the cable 3701 may include cutting elements 3702 such as beads, blades, wires, or other suitable cutting elements. In some embodiments, the cutting elements may be crimped onto the wire or attached by other suitable methods. The cutting cables may cut tissue using an energy such as heat or radio frequency energy. The energy may function to desiccate and/or shrink the tissue, rather than cutting it. As shown in FIG. 37, a portion of the device may include cutting cables, while a portion of the device includes rungs threaded onto cables (with or without cutting edges on the rungs). The cutting cables and the cables onto which the rungs are threaded may be the same or different cables. As shown in FIG. 38, a tissue modification device may include rungs 3801 along a portion of the device, and may further include a cutting cable 3802 coupled to the rung portion of the device.

As mentioned above in reference to FIGS. 22A-B, the cutting cables may be coupled to a U-shaped rung. The U-shaped rung may function to allow the legs of the rungs to pass through soft tissue 2208, such as ligament, as the cutting edges cut through the tissue, such that the base portion 2202 of the rung does not catch on the tissue or otherwise obstruct the cutting of the tissue. The U-shaped rung may further function to support the cutting cable, and prevent two parallel cables from approximating toward one another. In some embodiments, spacers 2206 may be coupled to the cable between two adjacent U-shaped rungs. The spacers 2206 may include a cutting edge 2207.

The device may include a shield coupled to the cutting cables. The shield may be coupled to the cutting cables such that while the cables are adjacent to the target tissue, the shield protects the adjacent non-target tissue, such as neural tissue, and/or may collect the tissue cut by the cutting cable. In some embodiments, the cutting cables function to slide distally and proximally within or over a substantially stationary shield. In some embodiments, the shield may function to contact and/or engage with and remove a swath of tissue (for example, soft tissue such as ligament) cut by the cutting cables.

In some embodiments, the rungs may have varying widths along the length of the tissue modification device. For example, as shown in FIG. 24A, the rungs toward the distal end of the device (e.g. rungs 2401) may have a small width, while rungs towards the proximal end of the device (e.g. rungs 2404, 2405, and 2406) may have a larger. For example, the small width may be on the order of 1 to 6 mm, while the large width may be on the order of 6 to 8 mm. Thus, there may be an intermediate region along the length of the tissue modification device region having rungs 2402) over which the width of the device (approximately the width of the rungs in some variations) transitions from relatively narrow to relatively wider. In some embodiments, there may be rungs of a medium width in the center portion of the device. These transition rungs may include cutting edges or may alternatively be non cutting rungs.

Figure 2B:
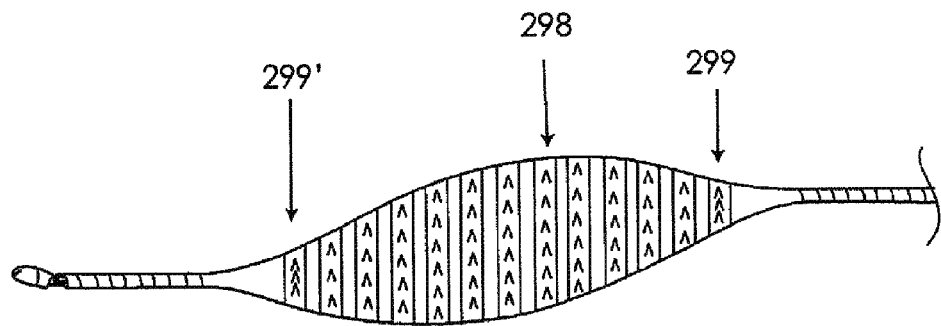
FIG. 2B is a perspective view of another variation of a tissue modification device with progressively larger and smaller blades arranged along the length.
Figure 24F:
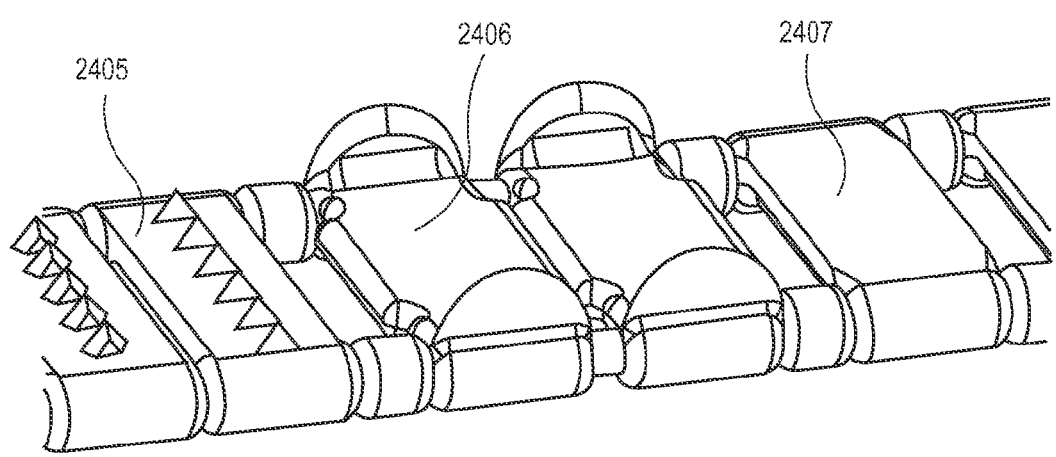

In one variation, as shown in FIG. 2B, the cutting edges may have different heights on different rungs. For example, in FIG. 2B the cutting edges on the rungs toward the center of the device 298 may have a first height, while the cutting edges on the rungs toward the proximal 299 and/or distal 299' ends of the device may have a second height. The first height may be larger than the second height, allowing the device to cut first a shallow cut, and then a deeper cut as the device is pulled along against tissue. The cutting edges in this configuration may function to provide a smooth transition as the device is pulled along against tissue and the sequentially higher cutting edges begin to engage with the tissue. Alternatively, the second height may be larger than the first height. In some embodiments, as shown in FIG. 24, adjacent cutting edges may have different heights. For example, in FIG. 24D a first set of cutting edges includes a cutting edge having a first height, a cutting edge having a second height, and a third cutting edge also having the first height. In FIG. 24D, the second height is taller than the first height. There may be any suitable number of adjacent cutting edges having each of either the first height or the second height, and in some variations, there may be a number of cutting edges having any other suitable height. As shown in FIG. 24F, a tissue modification device may include a second set of cutting edges having a third height. For example, FIG. 24A, the third height may be taller than the second and/or first height. In some embodiments (e.g. FIG. 24A) the first set of cutting edges may be distal to the second set of cutting edges.

In some variations, the cutting edges are formed from the material forming the rung, and the cutting edge (e.g., blade) is machined as part of the rung. For example, a rung may have an initial thickness measuring the height of the rung and the blade. The material at this initial thickness is machined (or otherwise removed) to form a series of blades projecting from the surface of the rung. Alternatively, the cutting edges may be cut out of the surface of the rung, and bent out of the surface of the rung such that the cutting edge or blade is substantially perpendicular to the rung. The cutting edge may be cut by Wire EDM machining (Electrical Discharge Machining), or any other suitable process. In some embodiments, the cutting edges or blades may be manufactured separately and connected to the rung.

In FIGS. 2A and 24A the rungs are threaded onto the cables by openings or channels formed in the rung. For example, a tissue-modification device such as the one shown in FIG. 2A and 24A may be formed by threading the various components (e.g., rungs, spacers, etc.) onto the cable(s) connecting them. In some variations (described in greater detail below), a tissue collection region may be connected below the rungs. In some variations the rungs may be rings, or may include space for tissue collection or a tissue-collection region.

Figure 2C:
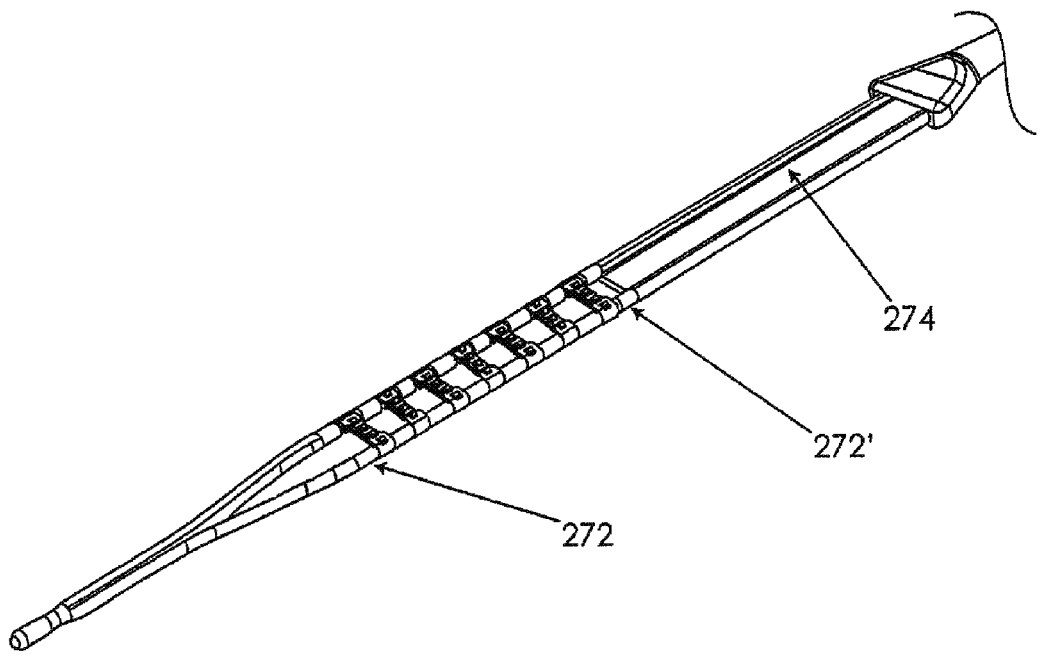
FIG. 2C is another variation of a tissue modification device.

In some embodiments, as shown in FIG. 2C, crimping elements 272, 272' may also be threaded onto the cables by openings or channels formed in the crimping elements. Once in place, the elements may be crimped to the cable or fixed to the cable in any other suitable fashion, such as by welding. The crimping elements fixed to the cable function to hold the rungs and other various components in place, and may further function to avoid loading the proximal and/or distal portions and/or ends of the tissue modification device.

The cables or rungs in one or more regions along the device may be covered or protected. For example, in FIG. 2C, the proximal portions of the tissue modification device includes a protector region, such as a solid material or covering element over the cables. Thus, the tissue modification device may have a solid proximal end protector region or portion 274. This solid portion may be a polymer extrusion, or any other suitable material in any suitable configuration.

Figure 2D:
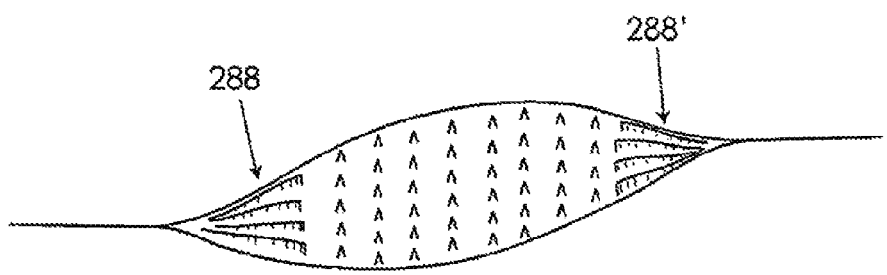
FIG. 2D is another variation of a tissue modification device including two ramp regions.

A widener or ramp region or regions may also be included as part of the tissue modification device. For example, FIG. 2D shows one variation of a tissue modification device having ramp regions 288, 288' at the proximal and distal portions of the tissue modification device. In some embodiments, the ramp begins towards the proximal and/or distal ends of the device, at a height approximately flush with the device, and increase. For example, the height may increase to approximately the height of any blades or cutting surfaces, or slightly higher. In some embodiments, the height of the ramp increases to a height approximately equal to or just below the height of the blades. The ramp may function to provide a smooth transition as the device is pulled along against tissue and the cutting edges begin to engage with the tissue. The ramp may extend across multiple rungs, a single rung, or may be coupled to the cables of the device. The ramp may be a solid structure, or a ribbed structure (as shown in FIG. 2D).

Rungs 203 with cutting edges 211 may extend over a portion of the length of the device. As illustrated in FIG. 2A, the device may include two or more rungs with cutting edges or blades 203 (e.g., "cutting rungs"). In this example, these cutting rungs 203 are separated by a gap formed by spacing elements 209 between the rungs. These spacing elements are also attached to the connector 201, 201' that flexibly connects the rungs. In FIG. 2A the spacers are threaded on the two parallel cables. The sizes of the connectors and/or spacing elements 209 may be varied to change the spacing between the rungs, and also the longitudinal shape (curvature) of the device, as described in greater detail, below. As shown in FIG. 24D, in some embodiments, a spacer 2408 may be integrated into the rung 2404. The spacer may be sized and configured such that two adjacent rungs define a space 2409 between them (cable 2410 can be seen in the space 2409 between the adjacent rungs).

Returning to FIG. 2A, in addition to the cutting rungs 203, other rungs may also be included that do not have a cutting surface. For example, linking rungs 205, 205' may be used. In FIG. 2A distal linking rungs 205 are shown removed from the device, but may be included. These rungs may protect the cable, and/or the tissue, and may be different sizes. Nearer to the distal end 235 of the device shown in FIG. 2A, smaller rungs 206 may be used to house the cable or cables connecting the rungs. These rungs 206 may be shaped to allow the device to be flexible in one or more direction (e.g., up/down relative to the major surface), while limiting the flexibility in other directions.

In some embodiments, the cutting rungs, non-cutting rungs, spacing elements, or any other suitable portion of the device may include a tracking element. For example, a tracking element may be disposed in the distal end of the device, such that the tip of the device may be tracked as it is inserted into a patient and/or moved within the patient. Alternatively, the device may include multiple tracking elements disposed along the length of the device, or multiple tracking elements disposed along a portion of the length of the device (for example along the cutting region of the device). In some embodiments, the tracking element is a material that is detectable by an imaging system. Some examples of suitable tracking elements include echogenic materials or substances (i.e. configured to form an echogenic surface) detectable by an ultrasound system, and radio-opaque materials detectable by a radiograph system, such as a fluoroscope. Alternatively, the tracking element may be configured to be detectable by an MRI or Infrared system. In some embodiments the tracking element is preferably a coil configured to be detected by an electromagnetic tracking or navigation system. For example, the devices described herein may incorporate a tracking system such as the AXIEM™ Electromagnetic Tracking Technology, e.g., the StealthStation® AXIEM™ (Medtronic Navigation, Louisville, Colo. USA). In some embodiments, the device is configured to generate an electromagnetic field around a patient's target anatomy that can be tracked to triangulate the positioning of devices having tracking elements.

The proximal end 233 of the device shown in FIG. 2A includes a handle 231 which may be permanently or removeably attached to the proximal end. The distal end 235 shown in FIG. 2A includes a guidewire coupler 237 that is flexibly attached to the distal end of the device. As shown FIGS. 24A and B, guidewire coupler 2411 is also flexibly attached to the distal end of the device. In some embodiments, the guidewire coupler has a tapered shape such that it has a first width at the distal end and has a wider width toward the proximal end of the coupler. In some embodiments, the proximal end of the coupler has substantially the same width as rungs 2401. A guidewire coupler as shown in FIG. 24B, may function to move (and thereby guide the trailing device) over, under, or around a soft tissue, such as ligament, rather than cutting or ripping through the tissue.

A guidewire coupler is configured to attach to a guidewire (e.g., one end of a guidewire) so that the device can be manipulated, at least in part, by pulling on the guidewire after the guidewire has been secured to the device. For example, in some variations a guidewire may be inserted into the body from a first location outside of the body, then passed around the target tissue (e.g., around a spinal foramen) and out of the body from a second position. The distal end of the guidewire may then be coupled to the flexible tissue modification device (such as the one shown in FIG. 2A) and pulled through the body until the tissue modifying region of the device, e.g., the portion of the device including cutting rungs 203, is positioned opposite the target tissue. In some variations the guidewire used includes a tip region that is enlarged and may engage the guidewire coupler. For example, the guidewire may have a proximal end with a flange or ball. This enlarged region may be configured to fit into an opening on the guidewire coupler 242 so that the guidewire can be pulled distally from outside of the patient. In some variations the distal end of the device may be completely withdrawn, so that it can be grasped and manipulated. In other variations, the distal end of the tissue-modification device remains coupled to the guidewire, and the guidewire may be grasped to manipulate the distal end of the tissue-modification device. A handle may be attached to the guidewire.

The overall tissue-modification device shown in FIG. 2A has an elongate body formed of the plurality of substantially rigid rungs. This variation has a length (an axial length, from proximal to distal) and a width. The length of the device is longer than the width of each rung. In some embodiments, the ratio of the length of the device to the width of each rung is greater than five. Alternatively, in some embodiments, the ratio may be greater than ten. The device is also relatively thin; in this variation the thickness is smaller than the width of each rung. In some embodiments, the ratio of the width of each rung to the thickness of each rung is greater than two. Alternatively, in some embodiments, the ratio may be greater than five. The use of two cables for the device shown in FIG. 2A allows the articulation of the links.

Figure 3A:
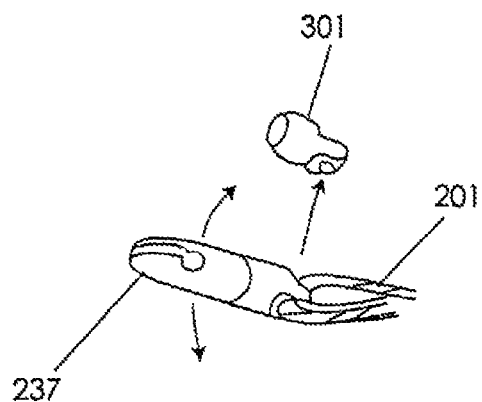
FIG. 3A shows one variation of a distal end of a tissue modification device, including a guidewire coupler.
Figure 3B:
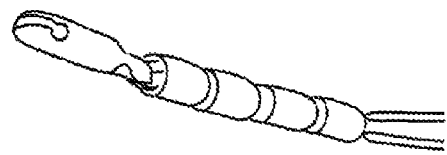
FIG. 3B shows another variation of the distal end of a tissue modification device, including a guidewire coupler.

The distal end of the device 235 (including the guidewire coupler region) is hinged, as is the connection to the proximal end 252. In some variations the couplings at the proximal and distal regions allow rotation of the connection with respect to the tissue modification region such that torque (twisting motion) is not transferred to the tissue modification region. For example, FIG. 3A illustrates one variation of the distal end of the tissue modification device in which the distal end includes a guidewire coupler 237 that is rotatably connected to the tissue modification device, more specifically to cable 201, by connector 301. Alternatively, the distal end, including a guidewire coupler, may be rigidly attached to the cable, as shown in FIG. 3B. The distal ends of the cable include rungs 206 (as shown in FIG. 2A), protector portion, or links that cover the cable, and may help prevent damage to tissue by presenting a relatively atraumatic surface.

In FIG. 2A, the flexible portion of the device formed by connected rungs or links is joined to the proximal end of the device, which may be less flexible, and may include a handle or an attachment region for a handle. This interface between the links forming the flexible region and the proximal end is shown as joint 252. The proximal joint 252 near the proximal end 233 is a ball joint 207 to which the cables are attached. The ball joint allows the rotation of the handle and/or proximal portion of the device with respect to the tissue modification region of the device. Thus, the proximal handle may be rotated along the long axis of the tissue modification device, but will not substantially torque the tissue modification region of the device.

The variation shown in FIG. 2A may also include a proximal connecting region 262 near the proximal end 233 of the device to which the handle 231 is attached. This connecting region may be relatively stiff (or inflexible), or it may also be flexible.

As mentioned, in operation, the device is urged against the target tissue and may be moved in the proximal/distal direction to modify (e.g., cut) the target tissue. For example, both the proximal and distal ends of the tissue-modification device may be pulled to urge the device against the target tissue, and may each be alternately pulled to a greater degree than the other handle to slide the device over the target tissue, allowing the cutting edges to cut and modify the target tissue. In this example, as the blade(s) cut the tissue, a moment is generated between the tip of the blade and the base of the blade, on the rung, where the cable runs through the rung. Thus, in some variations, the base of the blade rung must be sufficiently wide to resist rotating about the length of the cable. Furthermore, it may be advantageous to include fixed rigid sections.

In some embodiments, as rungs of the device are urged against the target tissue, a portion of a rung may contact the target tissue, while a second portion of the rung may not. Furthermore, a portion of a rung may contact the target tissue with a larger pressure than a second portion of the rung. It may be advantageous to maintain a substantially equal pressure and or substantially equal contact across the width of a rung. This may be achieved in one of several ways. For example, the rungs may be flexible or jointed. In this embodiment, as the device is urged against the target tissue, the rungs may function to conform across their width around the target tissue, and thereby maintain a substantially equal pressure and or substantially equal contact across the width of a rung.

Figure 39:
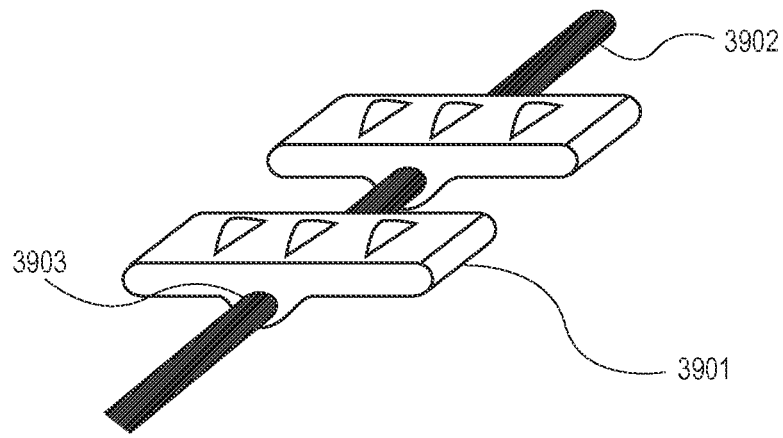
FIGS. 39-40 illustrate variations of a tissue modification device having a center cable.
Figure 40:
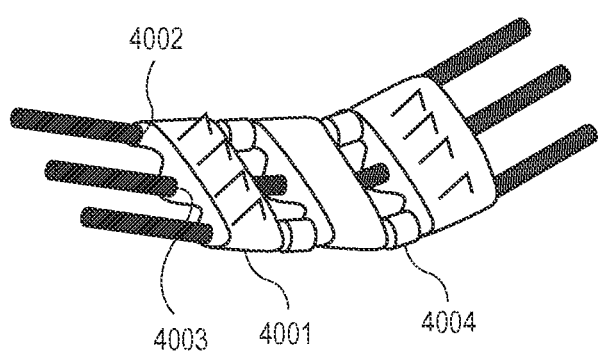

In FIG. 39, the rungs 3901 are coupled to a single load bearing cable 3902, running longitudinally along the device, coupled toward the center of the device, such that the rungs may rotate about the center cable, and thereby maintain a substantially equal pressure and or substantially equal contact across the width of a rung. In this fashion, the rungs of the tissue modification device will be maintained substantially parallel and/or flush to the plane of soft tissue (e.g. ligamentum flavum), preventing the device from preferentially cutting on one side. In some cases, if the device cuts preferentially with one side, the device can slide under the soft tissue rather than cutting a swath or strip of tissue, thereby potentially leaving target soft tissue behind after the procedure, which may be undesirable. As shown in FIG. 39, the rung may include a channel or opening 3903 toward the center of the rung such that the rungs can be threaded onto a load bearing cable through the opening or channel formed in the center of the rung. The rung may include more than a single load bearing cable toward the center of the width of the device. As shown in FIG. 40, the rung 4001 may include openings 4002 toward the sides of the rung in addition to the center opening 4003. The rungs may be threaded onto additional side cables. For example, the side cables may include spacers 4004 between the rungs as described above.

In some embodiments, as shown in FIG. 41, the rung is held at a first height 4101 above a first cable and a second height 4102 above a second cable. A shown, the first height is greater than the second height, such that the rung is at an angle, and may thereby maintain a substantially equal pressure and or substantially equal contact across the width of a rung. As shown in FIG. 42, the rung may include a channel or opening 4201 that is larger than the diameter of the cable 4202 onto which the rung is threaded. As shown, the rung may move on the cable such that it may maintain a substantially equal pressure and or substantially equal contact across the width of a rung.

In some embodiments, the cable(s) onto which the rungs are threaded remain lose prior to inserting the device into a patient. Once the device has been inserted, and the rungs are adjacent to the target tissue, the cables may be tightened such that both sides of the rung contact the tissue and maintain a substantially equal pressure and or substantially equal contact across the width of a rung. In this embodiment, the cables are tightened to different lengths. In some embodiments, as the device is urged against the target tissue, and pulled in a distal direction, a larger force may be applied to a first cable than to a second cable. Then, as the device is urged against the target tissue, and pulled in a proximal direction, a larger force may be applied to the second cable than to the first cable.

In some embodiments, the cables are stretchable. For example, a first cable may stretch to a length longer than the second cable such that both sides of the rung contact the tissue and maintain a substantially equal pressure and or substantially equal contact across the width of a rung. In some embodiments, the cables and/or rungs may be made out of an elastic or shape memory material. In this embodiment, the device may be inserted into a patient in a first configuration, and then once in portion, the device may shape change or reshape into a second configuration, wherein the second configuration is one that conforms to the target tissue, thereby maintaining a substantially equal pressure and or substantially equal contact across the width of a rung.

As mentioned, the rungs forming the device may be flexibly connected by hinges between the rungs. The connections shown in FIG. 2A are flexible connections, and individual rungs are not directly connected, but are instead connected via a cable. Since the cable is flexible, the flexion point is concentrated between rung and mating ferrule (spacer).

Figure 4:
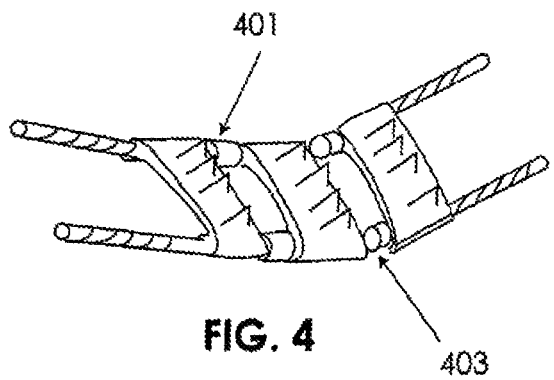
FIG. 4 shows a partial perspective view of a region of a tissue modification device.

FIG. 4 shows a portion of a tissue modification device similar to that shown in FIG. 2A. In FIG. 4, the cutting rungs each include a plurality of cutting edges. These cutting edges are again shown as oriented along the long axis of the device, although other orientations may be used. The cutting edges may be offset from each other along the long axis of the device, so a wider cutting area is formed. Alternating adjacent rungs may have different cutting edge configurations such that the cutting edges may be offset from each other along the long axis of the device. For example, as shown in FIG. 24E, a first rung may have cutting edges in configuration 2412 such that the position of the blades is biased toward a first side of the device (toward the top of FIG. 24A), a second rung may have cutting edges in configuration 2413 such that the position of the blades is biased toward a second side of the device (toward the bottom of FIG. 24A), a third rung may have cutting edges in configuration 2412 such that the position of the blades is biased toward the first side of the device, and so on.

In addition the cutting edges may be spaced from the sides of the rungs, allowing the edges of the tissue modification device to be relatively atraumatic. FIG. 4 also illustrates spacers between each rung or link, on either side of the device (i.e., on each of the cables). In FIG. 4, different spacers are shown, including relatively long ferrules 401, and bead-like spacers 403. The different spacers may modify the flexibility of the device.

Figure 5B:
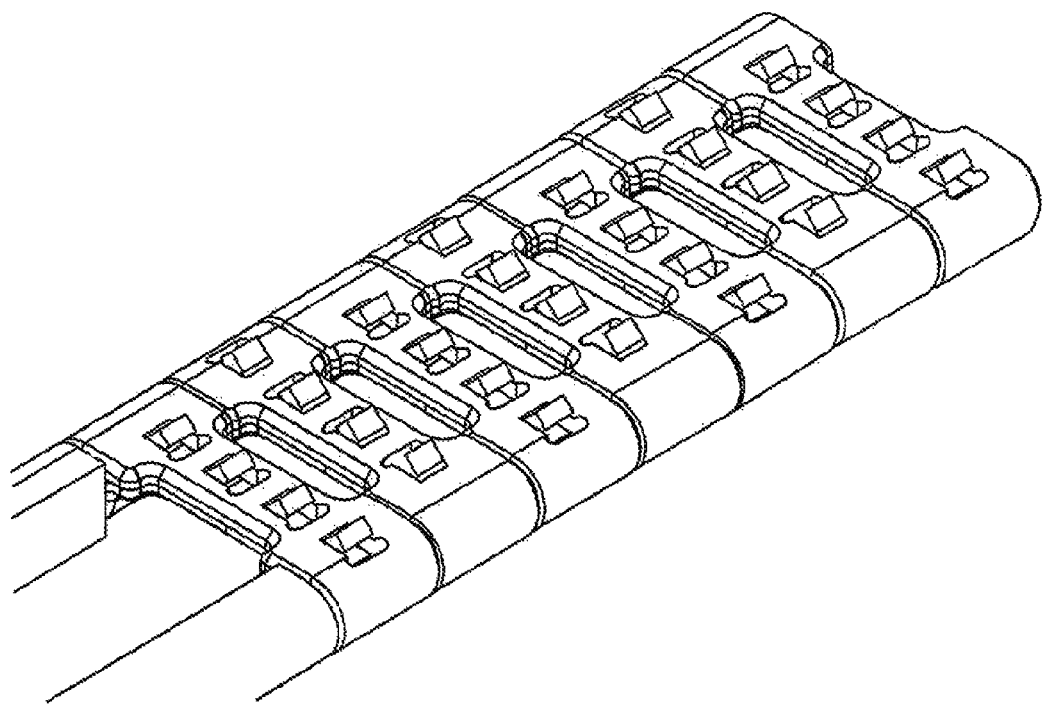
FIG. 5B is a partial perspective view of another variation of a tissue modification device.
Figure 5A:
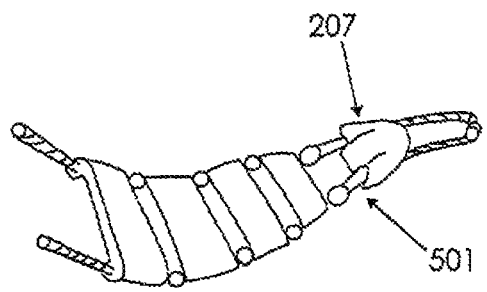
FIG. 5A is a partial perspective view of another region of a tissue modification device.

FIG. 5A illustrates a portion of the proximal end of the tissue modification device shown in FIG. 2A in which the cables are attached to the joint 207 by coils 501 that permit the cables to flex during operation. In some variations, these coils may be springs.

In some variations, as shown in FIG. 5B, the rungs forming the device may be flexibly connected by hinges between the rungs without spacers. The connections shown in FIG. 5B are flexible connections. Individual rungs are not directly connected, but are instead connected via a cable. Since the cable is flexible, the flexion point is concentrated between each rung. The length of each rung may be designed such that every transition point between each rung is a hinge point. As shown in FIG. 5B, the rungs may be configured such that a pair of rungs defines an opening between them. This opening may provide a location through which tissue may travel and/or be collected.

In some embodiments, as shown in FIGS. 6-8A, a tissue-modification device may include flexibly connected rungs or links that do not require the connection by a proximal-distal cable illustrated in FIG. 2A. For example, FIGS. 6-8A show various methods of flexibly connecting rungs or links. In FIG. 6, two adjacent cutting rungs are joined together so that they may move relative to each other as the device is flexed. In this example the devices are hinged. FIGS. 7 and 8A illustrate alternative variations similar to FIG. 6. In FIGS. 6-8B, the adjacent rungs or links are directly connected to each other and can be bent or moved as illustrated by the arrows. As shown in FIG. 8B, the devices can be bent (at least partially). In FIG. 8B, the hinged region may be formed by bending two regions of the adjacent links over each other. In these variations, a separate connector (e.g., cable, etc.) is not necessary to allow adjacent links to flex. Alternatively, the hinged regions may include a hinge pin (not shown).

Figure 9A:
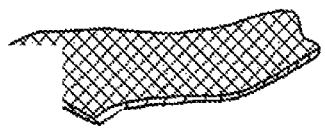
FIG. 9A shows a flexible material that may be used as a connector to connect rungs forming a tissue modification device.
Figure 9B:
FIG. 9B illustrate one variation of a rung that may be used with the connector shown in FIG. 9A.
Figure 9C:
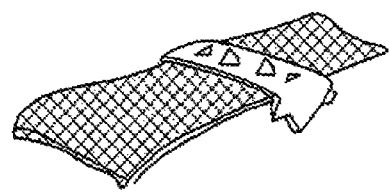
FIG. 9C illustrates the attachment of the rung of FIG. 9B onto the material of FIG. 9A.
Figure 9D:
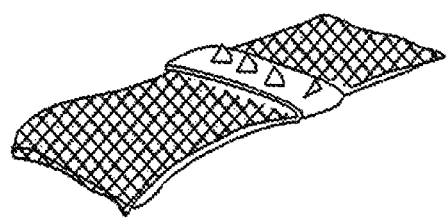
FIG. 9D shows the rung assembled on the connector material.

FIGS. 9A-9D illustrate another alternative method of connecting adjacent rungs or links to allow flexion or provide flexibility. FIGS. 9A-9D show an embodiment in which adjacent links are connected via a woven ribbon to which the rungs are secured. A portion of flexible material is shown in FIG. 9A. Any appropriate (flexible) material, including meshes, woven, non-woven, and polymeric materials may be used. For example, the flexible material could be made from several materials, for example: stainless steel, aramid fibers, carbon fibers, glass fibers etc. Rungs can be attached to the flexible material by any appropriate method. For example, FIG. 9B shows a rung having downward-pointed edges configured to either pierce the woven ribbon or to be bent around the connector material, as illustrated in FIGS. 9C and 9D. The bottom side of the material and/or rungs can be softened by molding a polymer 904 to the material, as illustrated in FIG. 9H. The material may be formed into a ribbon or band shape. Additional rungs (of different or similar dimensions), may also be secured to the connector material forming the device.

Figure 9E:
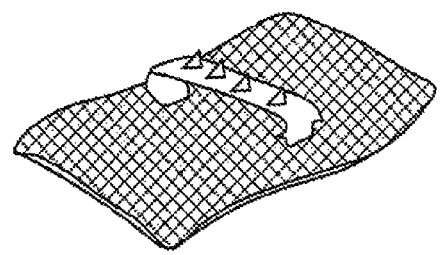
FIG. 9E shows an alternative attachment of the rung of FIG. 9B onto a material such as the connector material of FIG. 9A.
Figure 9F:
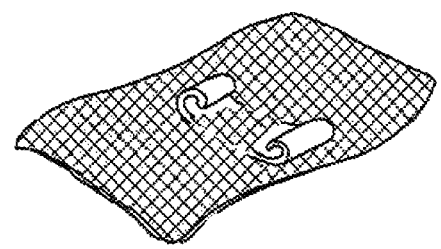
FIG. 9F shows a bottom view of the rung and connector assembly of FIG. 9E.
Figure 9G:
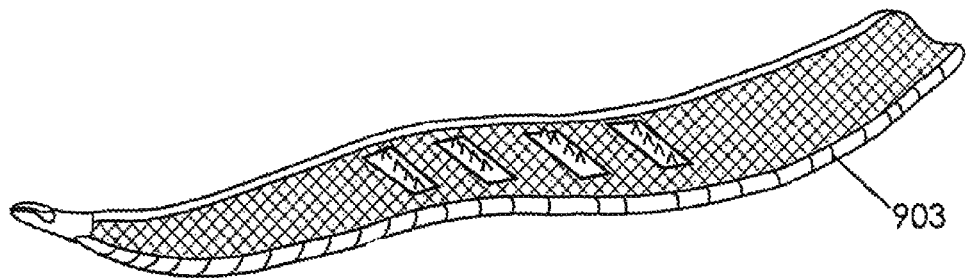
FIG. 9G is a partial perspective view of one variation of a tissue modification device.
Figure 9H:
FIG. 9H is a side cross-section through the tissue modification device of FIG. 9G.

FIGS. 9E and 9F show another variation in which the downward-pointed edges of the rungs penetrate the material and pass through it so that they can be and secured to it. For example, In FIG. 9E, the downward pointing edges pierce the material (though the material may also include pre-formed holes). The downward-pointed regions can then be bent back up to secure the rung to the connector material. Other means for fastening the rung to the connector material may also be used. In the example shown in FIGS. 9E-9G, the edge of the rungs is not concurrent with the edge of the tissue-modification device. FIG. 9G shows a portion of an exemplary tissue-modification device including a flexible connector connecting multiple rungs having cutting edges extending from them. In FIG. 9, the rungs are spaced from the edge of the tissue cutting device, and an atraumatic edge 903 is included along the outer periphery (along the major surface).

Figure 10:
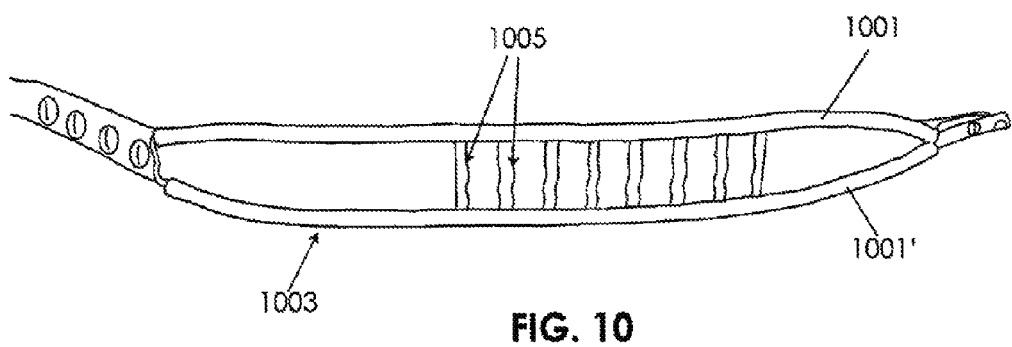
FIG. 10 is a bottom view of a tissue modification device including protective side covers.
Figure 11:
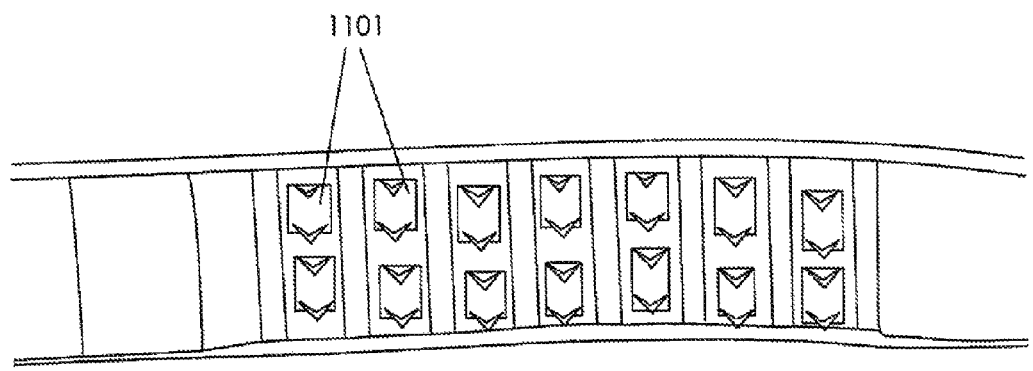
FIG. 11 is a top view of a tissue modification device including protective side covers.

Spacing the rungs from the edge in this manner may reduce the risk of side cutting. Other variations, including variations having a connector cable(s), the cable and rungs can be protected on the side by a separate tube like elements on the edges that are interlaced with the rungs and the cable, as illustrated in FIGS. 10 and 11. In FIG. 10, for example, the cables 1001, 1001' on either sides of the device are covered by a protective cover 1003. Rungs 1005 span the distance between the two cables. FIG. 11 shows a slightly higher magnification of the tissue modification region of the device shown in FIG. 10. In FIG. 11, the cutting edges 1101 are shown extending from the rungs.

Fixed Tissue Capture Region

The blade rung "ladder" design described above for the tissue modification devices having flexibly linked rungs may include spaces between the rungs. In some variations the tissue cutting region may also include holes or openings. These spaces between the rungs, holes, and/or openings may form part of a tissue capture region, or may act as vias or channels to direct cut tissue into a tissue capture region. As the tissue modification region modifies and/or removes the tissue, at least a portion of (and preferably the majority of) the cut tissue may be lodged between the cutting edges or blades and/or between the rungs of the device, such that the captured tissue is removed from the patient along with the device as the device is removed from the patient. Alternatively, in some variations, the space between the rungs may channel cut tissue into a tissue capture region. As the cutting edges (e.g., the triangular "teeth" shown in some of the figures, above) cut the tissue, the tissue may be driven into a tissue capturing or collection region. In some variations, the edge of the adjacent rung may shear the tissue as the device is urged against the tissue and moved. In some variations, the edge of the rung may also be sharp, or may include a sharp region. Thus, tissue may pass through the blade rungs and into a tissue collection region. The (typically upward) pressure of urging the device against the target tissue may therefore aide in packing the tissue into a tissue capture region. In some embodiments, the device may have elements to aid in the movement of the cut tissue. For example, the rungs may be designed such that two adjacent rungs function as a one way valve, allowing the tissue to enter through the space between the rungs, and then kept between or below the rungs and prevented from moving back out. Each rung may include a flap or a wing that couples to a flap or wing of an adjacent rung to function as a one way valve. The rungs may alternatively be designed in any other suitable fashion.

In general, a tissue capture region may require some amount of force or pressure to drive the cut tissue into the capture region. This may be particularly true for expandable tissue capture regions, such as an expandable bag that is attached behind the tissue modification region behind or within the rungs including cutting edges). As the tissue fills the area below the blades, the bag may expand to accommodate the increase volume. Increased pressure may be required to 'pack' the tissue into the tissue cutting region.

In some applications it would be beneficial to provide pre-expanded tissue capture regions, or tissue capture regions having a minimum volume that is fixed. The fixed minimum volume typically refers to a fixed open volume. Fixed minimum volume tissue capture regions typically include a minimum open volume, but this open volume may be increased as the device is operated; for example, the volume may be expandable from the fixed minimum open volume. Alternatively, the total volume of the tissue capture region maybe fixed or predetermined. Having a fixed minimum open volume allows tissue to enter the tissue capture region without having to apply additional force to drive the tissue into the tissue capture region.

In some variations a tissue collection region having a fixed minimum open space may be defined by the space between the openings into the tissue collection region (which may be the rungs of the tissue modification region) and a tissue collection substrate. The tissue collection substrate is typically spaced apart from the tissue modification side of the rungs by a thickness that forms the open space. The tissue collection region may have a length that extends at least along the tissue modification region of the tissue modification device (e.g., the cutting rungs in variations including rungs), but may extend further proximally/distally.

Figure 12A:
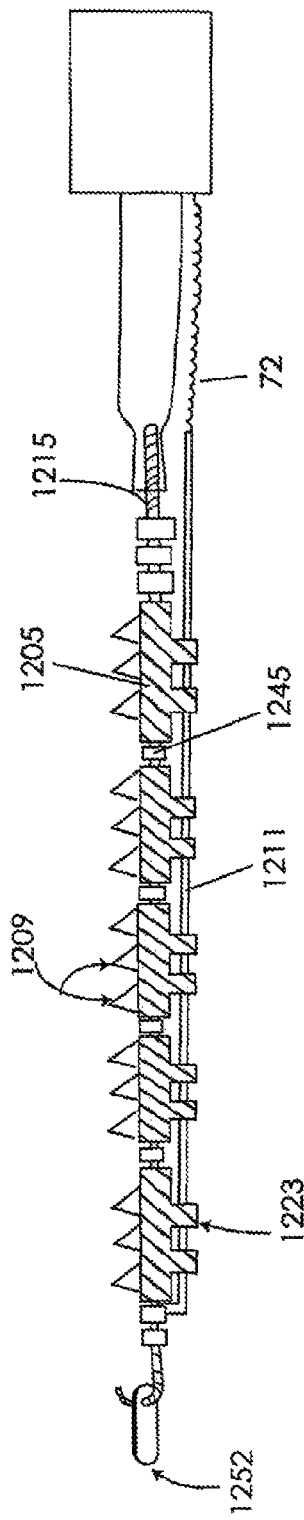
FIG. 12A is a side view of one variation of a tissue modification device including a fixed minimum open volume tissue collection region.
Figure 12C:
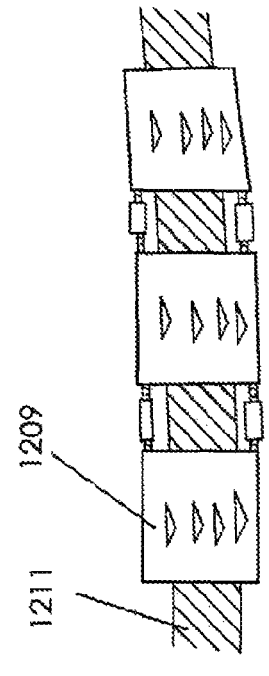
FIG. 12C is a top view of the tissue modification device of FIG. 12A.
Figure 12B:
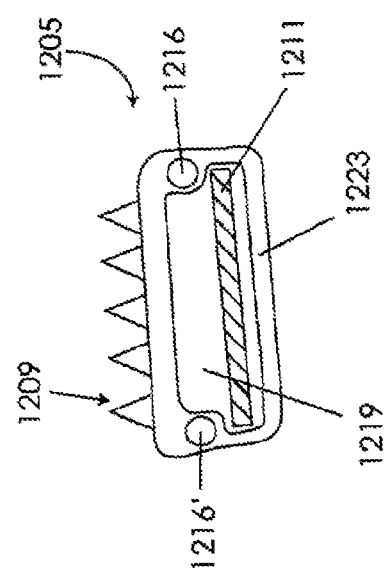
FIG. 12B is a cross-sectional view through the tissue modification device of FIG. 12A.

For example, FIGS. 12A-12C illustrate one variation of a tissue modification device including a tissue collection region having a fixed minimum open space. FIG. 12A shows a cross-section along the tong (distal/proximal) axis of the device. In this variation the device includes a plurality of flexibly connected rungs 1205 that are connected by a connector (a cable 1215). The rungs in the tissue modification region include cutting edges 1209. A tissue collection region 1219 (illustrated in FIG. 12B) is formed between the top of the rungs 1205 and a tissue collection substrate 1211. In this example, the tissue collection substrate 1211 is a semi-rigid substrate element that extends along the proximal/distal length of the device. In some embodiments, the substrate element may additionally include guiding features to move and/or position the tissue in a desired direction, such as toward the outer portions of the device, beneath the non-cutting rungs. For example, a guiding element may be one or more ridges in the substrate that are arrow or chevron shaped, with the vertex of the shape pointed toward the outer regions of the device. The distal end of this variation also includes a guidewire coupler or coupling region 1252, and individual links 1205 may be separated by spacers (shown as ferrules) 1245.

FIG. 12B shows a cross-section through one of the rung elements 1205 shown in FIG. 12A. In this variation, the rung 1205 includes two channels 1216 and 1216' through which the cables 1215 (FIG. 12A) may pass. The top (anterior) of the rung includes a plurality of cutting edges 1209. Within the rung 1205 is a fixed open volume 1219 that is formed between the top of the rung and a tissue collection substrate 1211 on the bottom of the rung. The tissue collection substrate may be secured within the rung by loops or straps 1223 that extend across the bottom of the rung. FIG. 12C shows a top view of the tissue modification device of FIGS. 12A and 12B.

The tissue-collection substrate portion of the tissue modification device shown in FIGS. 12A-12C is slideable within the rungs (e.g., along the straps of the rungs). One end of the tissue collection substrate may be fixed (e.g., near the distal end of the device) and the other end may include an elastic or spring element 1272 that allows the tissue-collection substrate to slide as the tissue modification device is bent during operation. FIGS. 13A-13D illustrate variations of tissue-collection substrates that may be used. For example, in FIG. 13A, the tissue collection substrate 1211 is a semi-rigid sheet of material as shown in FIG. 12A-12C. The tissue-collection substrate may be formed of any appropriate material, including metals or alloys (e.g., stainless steel, titanium, NiTi, aluminum, etc.), plastics (e.g., PEAK, PET, PP, EP, PET, etc.), and elastic materials (e.g., urethanes, silicones, etc.). Other materials may also be used. Since the overall device (including the tissue collection substrate) is flexible at least in the plane forming the major surfaces, the tissue collection substrate may be bendable. Thus, when more rigid materials are used (e.g., metals) to form the substrate, the substrate may be relatively thin.

Figure 12D:
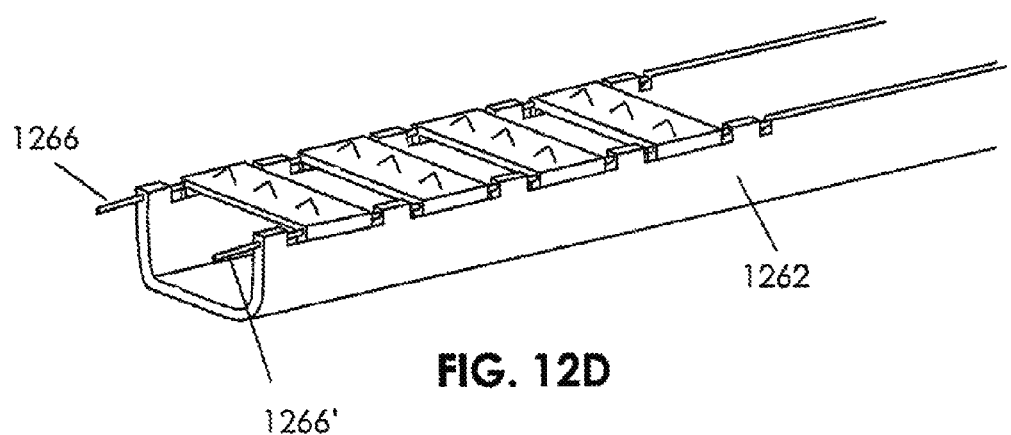
FIG. 12D shows a partial perspective view of a portion of a tissue modification device.
Figure 12E:
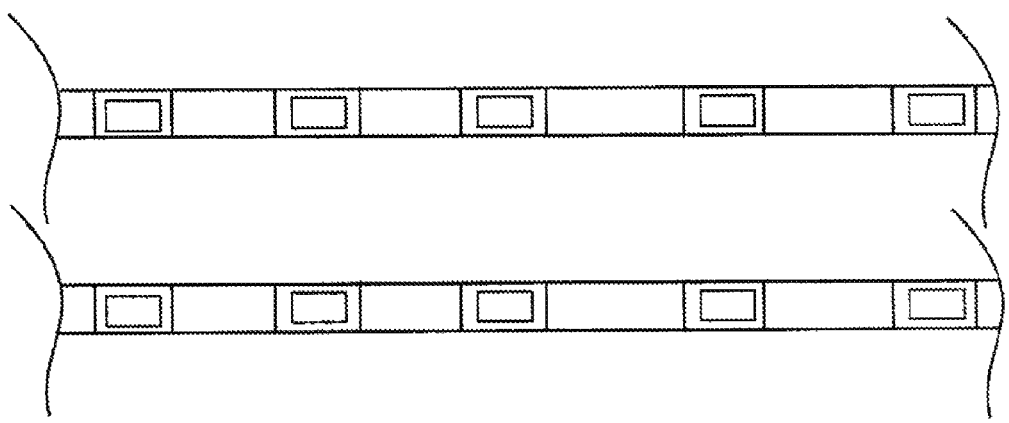
FIG. 12E is a top view of the tissue collection region of FIG. 12D.
Figure 12F:
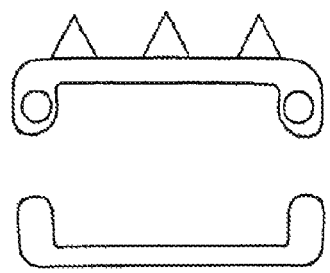
FIGS. 12F and 12G illustrate sections through the device shown in FIG. 12D.
Figure 12G:
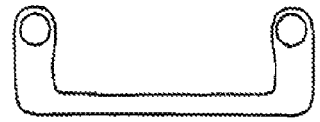

FIGS. 12D-12G illustrate another variation of a tissue modification device including a tissue collection region having a fixed minimum open space. FIG. 12D shows a perspective view of a portion of a tissue modification device including a tissue collection region 1262. This tissue collection region has sides and a bottom region, and includes a channel through which connectors (shown as cables 1266, 1266' in FIG. 12D) may pass. The tissue collection region may be a single, flexible piece, as indicated in FIG. 12D, or it may be a plurality of pieces linked by the connector. In this variation, the tissue collection region also includes spaced into which rungs may fit so that the connectors may pass through the rungs. This is also apparent from the top view shown in FIG. 12E. FIGS. 12F and 12G illustrate sectional views taken through a portion of the tissue modification device including a cutting run (shown in FIG. 12F) and a portion of the tissue modification device that is between adjacent cutting rungs (shown in FIG. 12G).

Alternatively, the tissue collection region may include projections that project into a space or slot formed on the rungs; the connectors may pass through these projections and through the rungs. In addition, spacers (e.g., ferrules, beads, etc.) may be used between the rungs.

In some variations, the substrate may be configured to expand/contract as the tissue modification device is flexed. For example, as described above, in some variations the tissue collection substrate may be connected at one (or both) axial ends via a spring or elastic member. FIGS. 13B1 to 13B3 illustrate a side view of another variation of a substrate that is configured to accordion along its length as the device it is attached to is flexed. For example, when the tissue modification device is flexed or bent in a first direction the substrate may contract or accordion closed, as shown in FIG. 13B1. In the relaxed state the substrate is 'neutral', with folds that may be expanded or contracted, as shown in FIG. 13B2. When the tissue modification device is bent in a second direction the substrate may expand or accordion open, as shown in FIG. 13B3.

In an alternative variation the substrate is expandable, and includes rigid edge with an expandable element between, as illustrated in FIG. 14A. In this variation the rigid portion may be secured to the tissue collection device (e.g., to the links of a tissue collection device), and the expandable portion may be made of a mesh or thin plastic material. FIG. 14B shows just the rigid portion of one variation of this embodiment, in which the rigid frame 1401 surrounding an expandable portion 1403 includes cross-struts 1407. Substrates including expandable regions may be useful to allow the tissue collection region to expand even beyond the minimum fixed volume, allowing the collection of additional tissue even after the minimum fixed volume is filled.

Figure 15A:
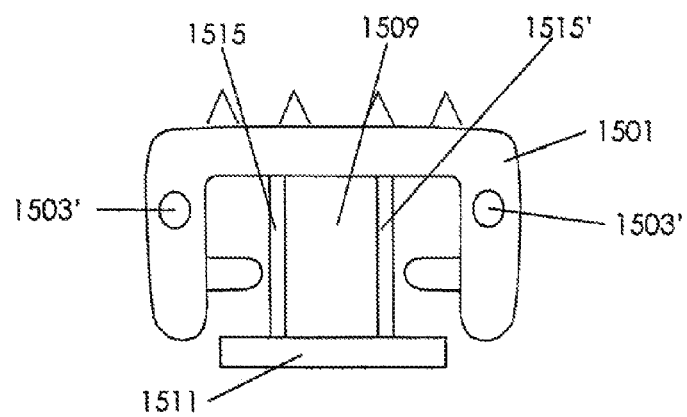
FIG. 15A is a cross-section through another tissue modification device having a fixed minimum open volume tissue collection region.
Figure 15B:
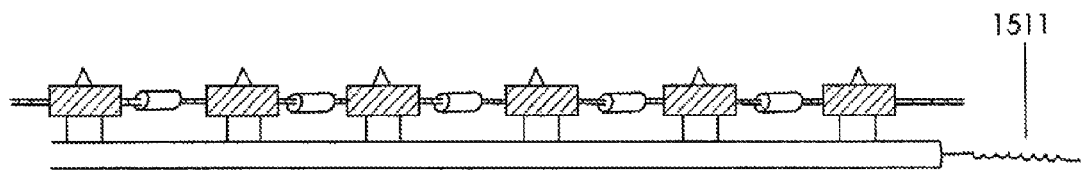
FIG. 15B shows a partial side view of a tissue modification device having a fixed minimum open volume tissue collection region.
Figure 15C:
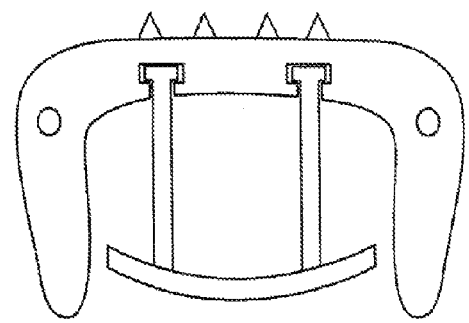
FIG. 15C is a cross-section through another tissue modification device having a fixed minimum open volume tissue collection region.

In general, the tissue collection substrate may be held to the tissue modification device by one or more connectors linking the tissue collection substrate to the rung. In FIGS. 12A-12C the tissue collection region is bounded by the tissue collection substrate that is secured to the link via a strap or loop that is formed by the rung. In some variations the connectors are not part of the rungs, but are separate elements. For example, FIGS. 15A-15C illustrate variations in which the tissue collection substrate is secured to the device by a cable or rod connector between each rung and the tissue collection substrate. In some variations, the connector is formed as a part of the tissue collection substrate. FIG. 15A shows a cross-section through a flexible tissue modification device having rungs 1501 and a tissue collection region 1509 that is formed between the top of the rung 1501 and a substrate 1511 that is secured to the rung by a pair of cables 1515, 1515' or rods. FIG. 15C shows a similar variation in which the substrate is secured to the rung by connectors that may swing or slide. As described, the rung shown may be flexibly connected via one or more cables 1503, 1503'. In all of these examples of tissue collection regions there is a minimum open volume that has a fixed minimum, so that, even when flexed, the tissue collection region has a non-collapsible open space so that tissue can enter the space. In some variations this minimum fixed space is formed by a separation of between about 2 and about 6 mm between the rung forming the top of the space and the substrate.

FIG. 15B shows a cross-section through the tissue modification region of a tissue modification device including rung and tissue collection design shown in FIG. 15A. As before, the tissue collection substrate in this example is shown axially connected to the device via a spring 1511.

In operation, tissue cut by the blades may be collected into the tissue collection regions described. As mentioned, openings between the rungs may act as channels or vias through which cut tissue may pass into the collection region(s). In some variations, the tissue modification device may include openings adjacent to the cutting edge(s) through which tissue may pass. Although the examples described above include tissue collection regions having a fixed minimum open volume as part of a tissue modification device comprising a plurality of rungs, a fixed minimum open volume tissue collection region may be incorporated as part of any tissue collection region, even those not having rungs.

Other examples of tissue capturing mechanisms which may be used are described, for example, in U.S. Ser. No. 11/687,558 (titled "FLEXIBLE TISSUE REMOVAL DEVICES AND METHODS"), filed on Mar. 16, 2007, and U.S. Ser. No. 11/687,548 (titled "TISSUE REMOVAL WITH AT LEAST PARTIALLY FLEXIBLE DEVICES"), filed on Mar. 16, 2007, and U.S. Ser. No. 11/952,934 (titled "TISSUE REMOVAL DEVICES AND METHODS"), filed on Dec. 7, 2007; these references are all incorporated by reference herein.

Figure 16A:
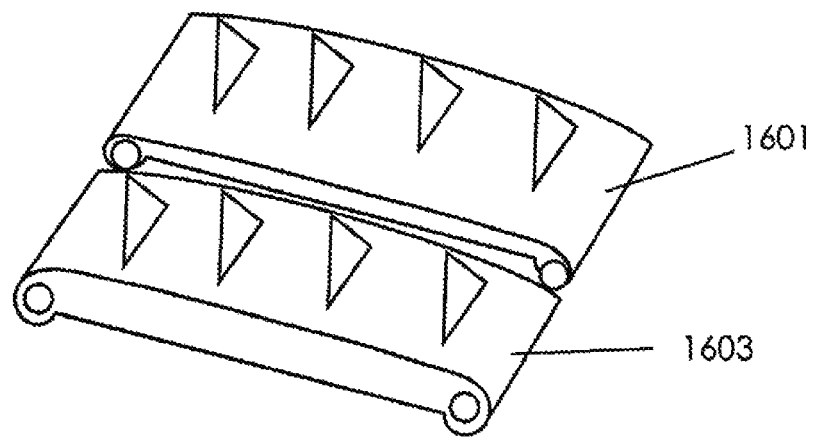
FIG. 16A shows perspective views of two adjacent rungs having alternating tissue cutting edges or blades.
Figure 16B:
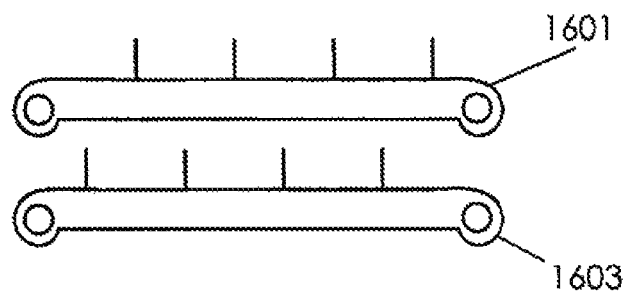
FIG. 16B shows a side view of both of the two rungs illustrated in FIG. 16A.
Figure 16C:
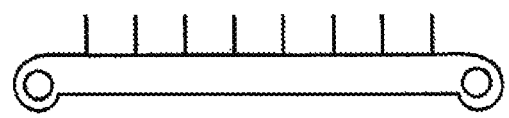
FIG. 16C shows a side view of the two rungs shown in FIGS. 16A and 16B when the two rung has been positioned adjacent to each other.

As mentioned above, the spacing and orientation of the cutting edges of the tissue modification devices may be arranged to optimize performance. For example, FIG. 16A to 16C illustrate one arrangement of cutting edges (blades) in which adjacent rungs have blades that are offset from each other. Offsetting the blade in this manner may allow them to more uniformly cut as the device is operated to modify tissue. Blade density may be important when it comes to cutting both soft tissue and bone. To improve the density and allow for material to pass through blade teeth, the leading and following blades may be interdigitated. FIGS. 16A-16C show the interdigitation of a set of blades. The first rung 1601 (Rung-A) cuts a leading path and the second rung 1603 (Rung-B) cuts a following path. This arrangement of cutting edges and rungs may help maximize the material removal for one cut stroke. FIG. 16C is a side view of Rung-A directly in front of Rung-B.

Non-Linear Shapes and Shape Morphing

In addition to the substantially linear tissue modification devices described above, any of these tissue-modification devices may also be configured to have a non-linear shape (e.g., axial shape) and/or be shape-morphing devices that can convert between linear and non-linear shapes. Non-linear devices may be pre-formed into a curved or bent shape (such as "s"-shaped, or serpentine, device or "c"-shaped devices, or the like). Alternatively, a non-linear device may be a shape-morphing device that can be changed from a linear to a non-linear shape, either before or during use of the device to modify tissue.

The phrase 'linear' and 'non-linear' shapes typically refer to the shape of the device along the major (distal/proximal) axis, when looking down on the major (tissue-modifying) surface.

Figure 17A:
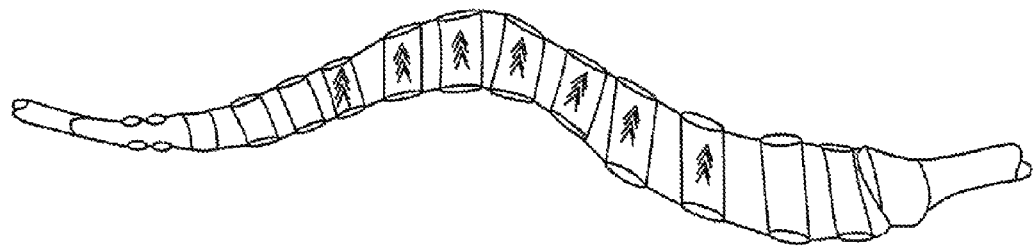
FIG. 17A shows one variation of a tissue modification device having a non-linear axial shape.
Figure 18:
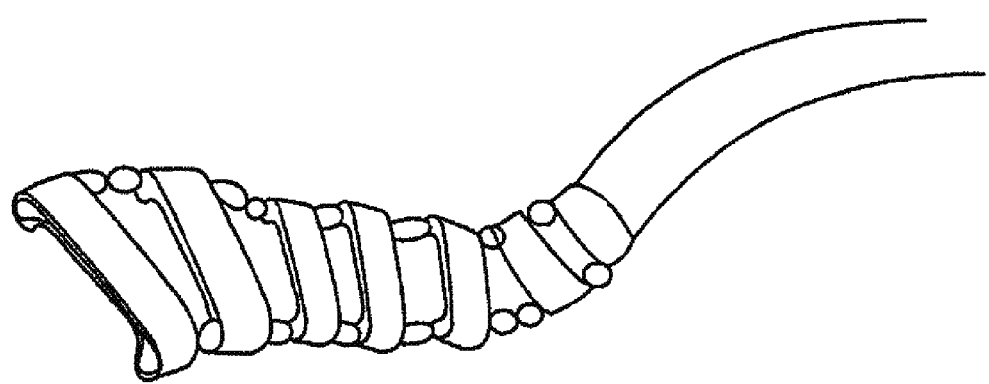
FIG. 18 is a partial perspective view of a flexible tissue modification device having a non-linear axial shape.

For example, FIG. 17A illustrates a device having S-shape (or serpentine) shape. This is a non-linear device (since the major surface does not travel in a line, but is curved). The device can be constructed using the cable (or wire) rung design, as illustrated in FIG. 18. In FIG. 18, the links are separated by one or more spacers that are unequal in length from one side of the device (e.g., one cable) to the other. This difference in spacing causes the device to curve, as shown. For example, the side of a device with a larger radius of curvature may include spacers such as relatively long ferrules 401 (shown in FIG. 4), and the side of a device with a smaller radius of curvature may include bead-like spacers 403 (shown in FIG. 4). Curved devices may have a wider stroke length when cutting the tissue, and may therefore cut a wider region of tissue. For given stroke length, the amplitude (peak to peak of the curve) becomes the effective width of the device, producing a kerf wider than the individual rung.

Additionally the devices can be deployed into the spine in a linear configuration and then changed to a non linear configuration. This conversion in shape may be achieved in-situ by pulling on a cable on one side of the rung more than the other side. Alternatively, you can pull both sides with the same tension in combination with variably compressible ferrules/spacers between the rungs in selected locations. For example to achieve a concave curve to the device on the right side, the right side would have more compressible ferrules (elastomeric) than the left side. Once the new non-linear shape was achieved, the cable wire(s) could be locked in position near the proximal end and/or handle. If desired, the cables could be readjusted to form a linear shape to the device prior to device removal. For example, a device may be increased in width by shift parallel links from an oblique angle to perpendicular with the cable, shown in the images below.

Figure 17B:
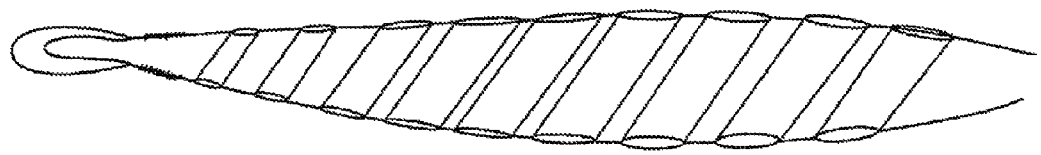
FIGS. 17B-17C illustrate one variation of a tissue modification device that may be expanded from a first, narrower, configuration (shown in FIG. 17B), into a second, wider, configuration (shown in FIG. 17C).
Figure 17C:
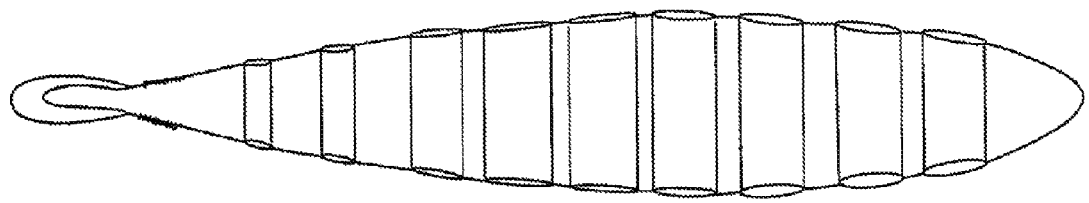

In some variations, the shape-morphing devices may be transitioned between a first straight (e.g., linear) configuration and a second straight configuration, with the first configuration being narrower than the second configuration. Two examples of this are shown in FIGS. 17B-17C and 17D-17E. In FIG. 17B the tissue modification device has a relatively narrow profile and can be expanded into a wider profile as illustrated in FIG. 17C. The rungs in 17B are initially diagonal, relative to the parallel cables flexibly connecting them. By pulling on one of the cables, one side of the device to which the rungs are connected, may be pulled to align the rungs perpendicular to the long axis of the device. Since the rungs are relatively rigid, this will expand the width of the tissue modification device, as indicated in FIG. 17C.

Figure 17D:
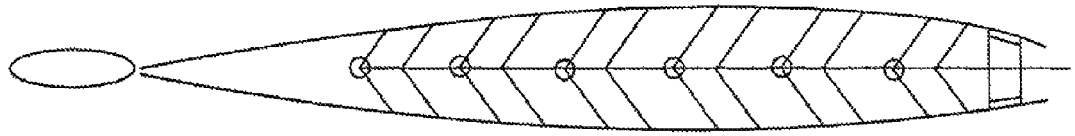
FIGS. 17D-17E illustrate another variation of a tissue modification device that may be expanded from a first, narrower, configuration (shown in FIG. 17D), into a second, wider, configuration (shown in FIG. 17E).
Figure 17E:
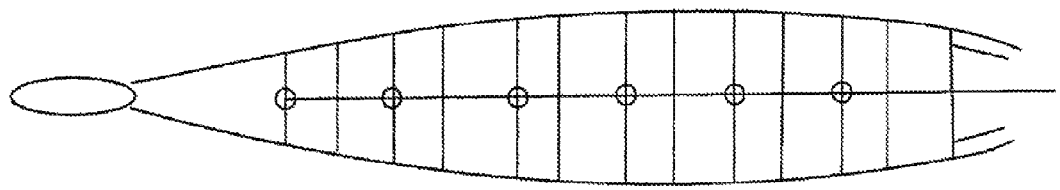

FIGS. 17D and 17E illustrate a similar variation, in which the tissue modification device may be expanded from a first linear configuration, in which the rungs are chevron-shaped when viewed from the top as in FIG. 17D, to a second linear configuration that is wider, in which the rungs can be pulled so that they are perpendicular to the long axis (proximal/distal axis) of the device, as illustrated in FIG. 17E. In this variation, a cable, pull wire, or the like may be connected to the rungs to convert them from the first to the second shapes. The rungs may be adapted hinged) for conversion. In some variations each run is actually a two rungs that are joined end-to-end.

Decompressing Spinal Regions

Any of the tissue modification devices described herein may be used to decompress one or more spinal regions, as mentioned above. In particular, any of these devices may be used to decompress nerve roots placed within the spinal anatomy along various paths, including those shown in FIGS. 19A-19C. Because these devices are flexible, and may be appropriately sized and shaped to fit within a neural foramen, these devices may be used to accesses appropriate regions of the spine from a single access point (e.g., from the patient's midline or near-midline region). The procedure may be used to decompress spinal nerve roots on the unilateral or bilateral side from the access point. A probe or guide may be introduced into the spinal epidural space (or along or just within the ligamentum flavum) at an appropriate spinal level using image guidance and/or tracking (e.g., electromagnetic tracking). In some embodiments, in which the probe or guide may be introduced just within the ligamentum flavum, the device may be used to cut a portion of the ligamentum flavum and in some cases may be used to cut a portion of the underlying bone, while leaving the surface of the ligamentum flavum intact. Introduction may be either via percutaneous puncture or open laminotomy.

Figure 19A:
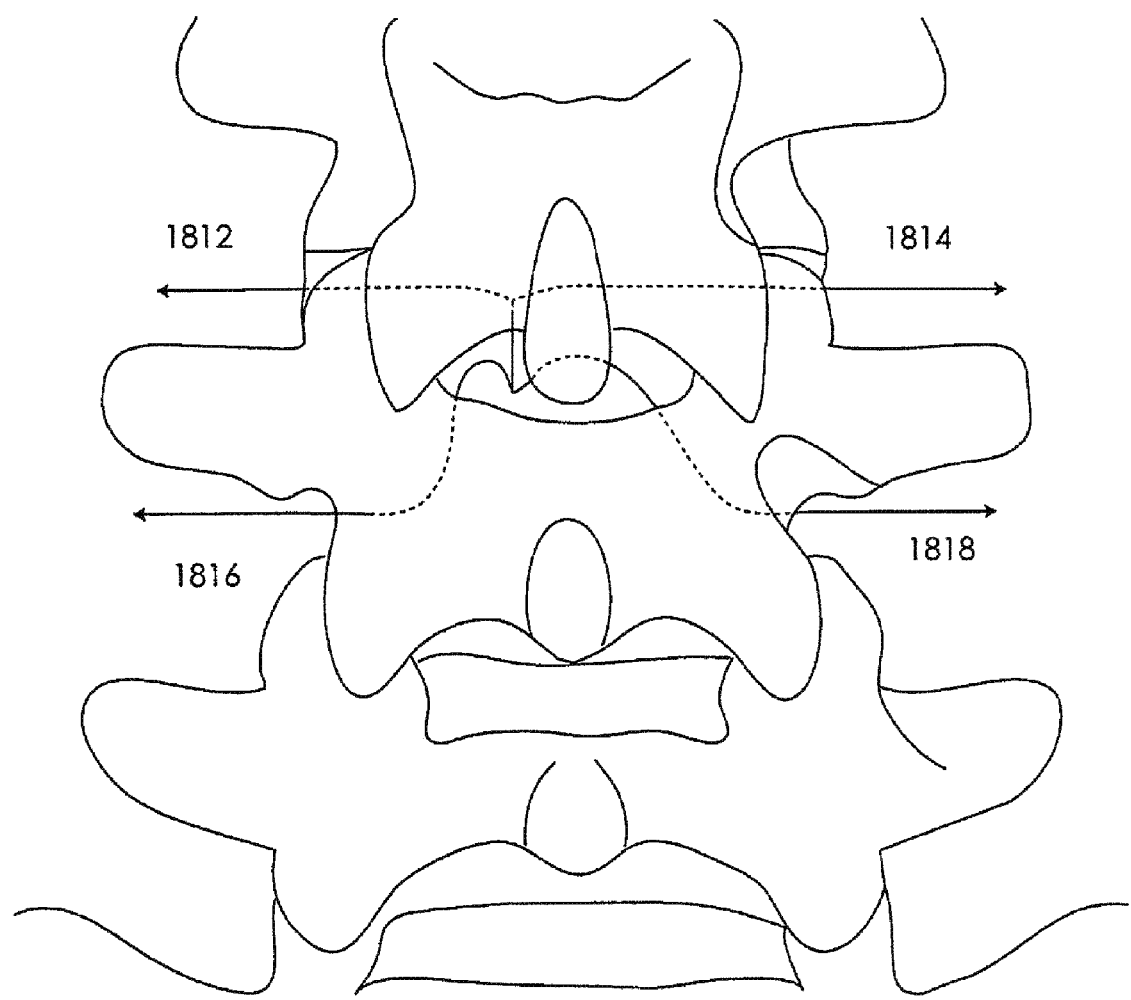
FIG. 19A is a posterior view of the spine indicating decompression paths at disk level and along the nerve root.

As shown in FIG. 19A, the device may be used to decompress an ipsilateral or contralateral proximal nerve (in a lateral recess). A guide may be deployed immediately cephalad to the caudal segment pedicle on the appropriate side (e.g., location 1810). This access point can be confirmed radiographically. If neural structures adjacent to the guide cannot be directly visualized, the relationship of these structures to the guide or tissue modification devices can be determined using electrical stimulation, ultrasound imaging, endoscopic mean or other techniques. In some variations, once the guide is deployed and optional neural localization is complete, a guidewire is passed via the cannulated guide. The guidewire can be sharp on its distal end and penetrate the skin dorsolaterally after exiting the foramen. The guidewire may include a wire exchange tip on its proximal end, as mentioned above. As shown in FIG. 19A, the guidewire may be threaded along a path from location 1810 to where it exits through the foramen, as shown by at least one of arrows 1812 (for ipsilateral decompression of the nerve root origin at the disk level) and 1814 (for contralateral decompression of the nerve root origin at the disk level). In some embodiments, the probe/guide is removed once the guidewire has been positioned.

Next, a flexible tissue modification device is attached to the proximal wire exchange tip, and a distal handle may be secured to the distal wire tip. The device can then be introduced into the epidural space and then into the lateral recess by careful upward force applied to the distal handle. In some embodiments, the device is pulled by the guidewire on the path through the spinal anatomy. As described above, suitable paths include paths shown by arrows 1812 and 1814 to decompress the nerve root origin at disk level. Once the device is in place as confirmed visually or radiographically, bimanual reciprocating strokes may be utilized to decompress dorsal impinging bone or soft tissue at the nerve root origin. In some embodiments, approximately 30-40 reciprocating strokes are required to complete the decompression. This may be confirmed radiographically or with palpation by instruments. The device may then be detached and the wire removed.

The probe/guide may be reinserted to decompress the ipsilateral or contralateral distal (foraminal) portion of the nerve root, so that the same (or a different) tissue modification device may be used to decompress another region of the spine (or nerve root) using the same access or entry site. Thus, a guide may be deployed immediately caudal to the caudal segment pedicle on the appropriate side. The guide may be deployed in the same access point (location 1810) as described above. Transforaminal positioning and the relationship to neural elements can again be confirmed visually, radiographically, and/or with electrical stimulation, ultrasound or alternative means. Once appropriate localization is confirmed, the guidewire can be passed and probe/guide removed. As shown in FIG. 19A, the guidewire may be threaded along a path from location 1810 to where it exits through the foramen, as shown by at least one of arrows 1816 (for ipsilateral decompression along the nerve root) and 1818 (for contralateral decompression along the nerve root). A handle is attached to the distal guidewire and the tissue modification device to the proximal exchange tip. The device is then introduced into the spine (e.g., the epidural space, or the region anterior to the posterior edge of the ligamentum flavum) with careful upward force applied to the distal handle. In some embodiments, the device is pulled by the guidewire on the path through the spinal anatomy. As described above, and as shown in FIG. 19A, suitable paths include paths shown by arrows 1816 and 1818 to decompress along the nerve root. The foraminal decompression is performed using bimanual reciprocating strokes to remove impinging bone and soft tissue. In some embodiments, approximately 30-40 strokes are required to decompress the root. Confirmation of decompression may be done radiographically or using instruments to palpate along the root. The device can then be detached and the guidewire removed.

Figure 19B:
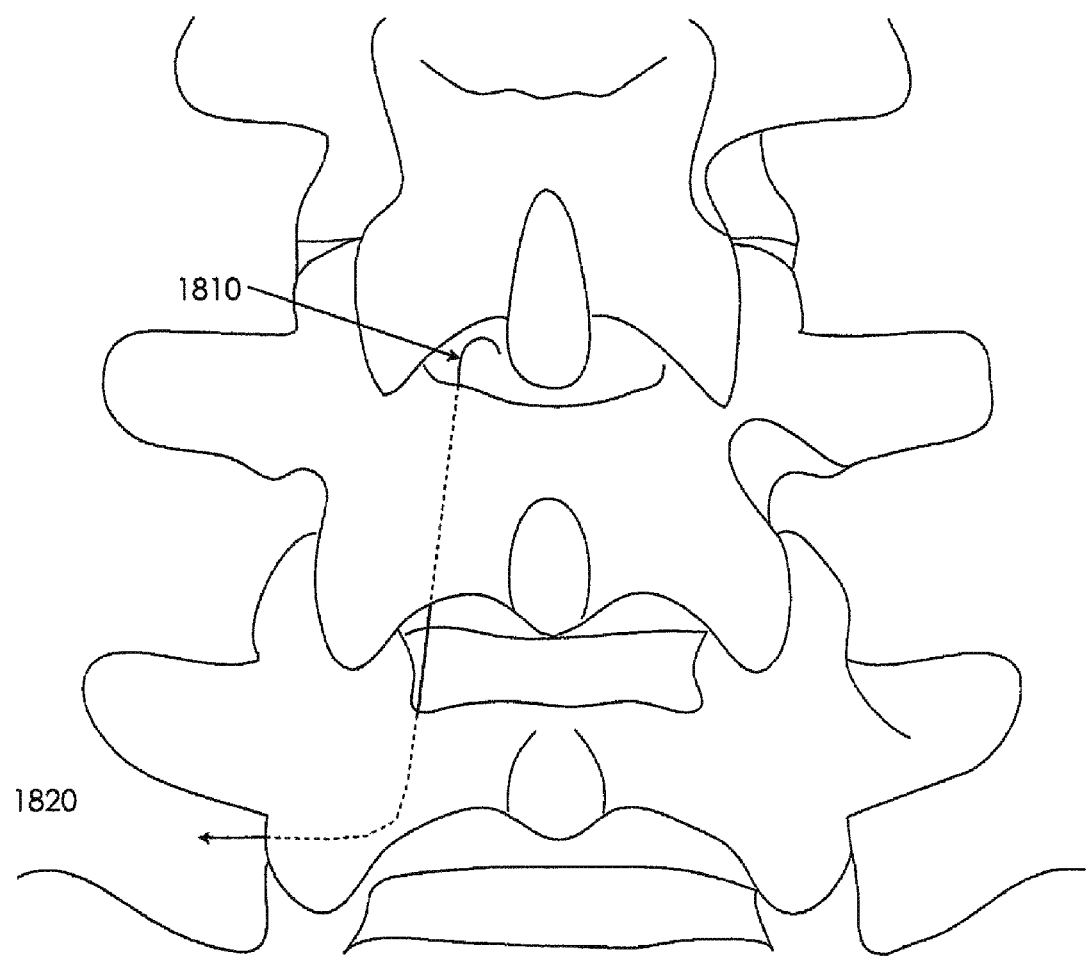
FIG. 19B is a posterior view of the spine indicating a decompression path for adjacent level lateral recess decompression.
Figure 19C:
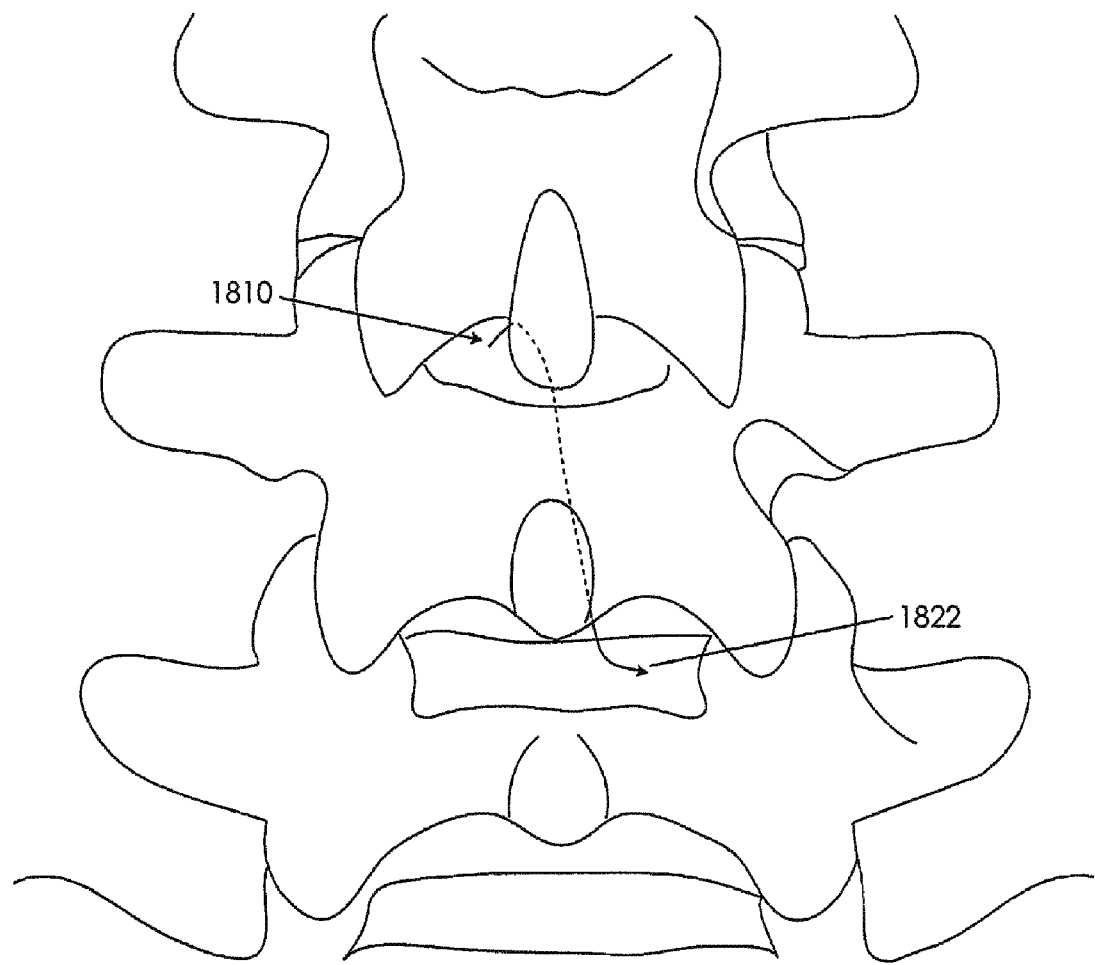
FIG. 19C is a posterior view of the spine indicating a decompression path for central canal decompression.

As shown in FIG. 19B, the devices described herein can used to decompress the ipsilateral or contralateral (not shown), or both, regions adjacent the level proximal to the nerve root (lateral recess). A guide may be deployed in the same access point (location 1810) as described above. Transforaminal positioning and the relationship to neural elements are once again confirmed visually, radiographically, and/or with electrical stimulation, ultrasound or alternative means. Once appropriate localization is confirmed, the guidewire may be passed and the probe/guide removed. As shown in FIG. 19B, the guidewire can then be threaded along a path from location 210 to where it exits through the foramen, as shown by arrow 220 (for ipsilateral decompression of the adjacent nerve root origin). A handle can be attached to the distal guidewire and the guidewire can then be attached to the distal end of one of the tissue modification devices described herein. The device can then be introduced into the spine by pulling on the guidewire. In some embodiments, the decompression device is pulled by the guidewire on the path through the spinal anatomy as illustrated in FIG. 19A, 19B, or 19C. As described above, and as shown in FIG. 19B, suitable paths include the path shown by arrow 1820 the adjacent nerve root origin. The lateral recess decompression may be performed using bimanual reciprocating strokes to remove impinging bone and soft tissue. In some embodiments, approximately 30-40 strokes are required to decompress the nerve. Confirmation of decompression may be done radiographically or using instruments to palpate along the root.

As shown in FIG. 19C, a probe/guide may be used to introduce a tissue modification device as described herein to decompress the central canal. The guide may be deployed in the same access point (location 1810) as described above. Once appropriate localization is confirmed, the guidewire may be passed and probe/guide removed. As shown in FIG. 5, the guidewire can be threaded along a path from location 1810 to where it exits through the intralaminar window, as shown by arrow 1822 (not the adjacent foramen). A handle may be attached to the distal guidewire and, the tissue modification device may be coupled to the proximal end of the guidewire. The device can then be introduced into the epidural space by pulling the distal end of the guidewire on the path through the spinal anatomy, drawing the device into position adjacent the target tissue in the spinal canal. As described above, and as shown in FIG. 19C, suitable paths include the path shown by arrow 1822 to decompress tissue associated with the central canal and may be effective in treating patients with central spinal stenosis. The decompression may be performed using bimanual reciprocating strokes to remove impinging bone and soft tissue. In some embodiments, approximately 30-40 strokes are required to decompress the root. Confirmation of decompression may be done radiographically or using instruments to palpate along the nerve.

In some embodiments, the probe, guide, or guidewire may also include a tracking element or plurality of tracking elements. The tracking element may be similar to the tracking element of the tissue modification device. As described above, in some embodiments the tracking element is a material that is detectable by an imaging system, while in some embodiments the tracking element is preferably a coil configured to be detected by an electromagnetic tracking or navigation system.

Any of the procedures described herein can be done in combination with other techniques including an open or minimally invasive decompression procedure where tools such as rongeurs and powered drills are used to remove tissue primarily around the proximal end of nerve root (lateral recess). Such techniques may include laminotomies, etc.

FIGS. 43A-F illustrate one variation of a system including one embodiments of the tissue modification device described above. Any of the tissue modification devices (and embodiments of these devices) described herein may be included in a system for treating spinal stenosis. In this variation, the system includes two types of tools for positioning a guidewire (43F), as shown in 43A and 43B. These tools are typically cannulated devices that may be used to position the guidewire around the target tissue. These cannulated tools may be steerable, or may have distal ends that are curved and/or extendable for steering the guidewire around the target tissue. During guidewire positioning, the location of one or more nerves may be configured using a neural localization device (e.g., FIG. 43C) that is configured to be positioned by pulling into place using the guidewire, similar to the method described herein for positioning an operating the tissue modification device. The neural localization device may include one or more electrodes for creating a localized electromagnetic field capable of stimulating only nearby nerves (thereby confirming they are adjacent to the pathway of the guidewire, or one or more sides of the guidewire pathway). In some variations the tissue modification device includes one or more neural localization devices. A handle may also be included, for attaching to the guidewire, better control of the guidewire. For example, in the system shown in FIGS. 43A-43F, the handle (FIG. 43E) is configured to connect to the guidewire (FIG. 43F), allowing the distal end of the guidewire to be pulled when the proximal end of the guidewire is coupled to the tool (e.g., the tissue modification device, FIG. 43D).

Any of the devices illustrated herein may be used to modify tissue, as discussed above. FIGS. 44A-44E illustrate one embodiment of a method for modifying tissue using one of the flexible tissue modification devices 10 described herein. In FIGS. 44A-44E, a patient's skin, target tissue TT and non-target tissue NTT are shown diagrammatically, rather than as specific structures. In one embodiment, the method of FIGS. 44A-44E may be employed in the spine, to remove ligamentum flavum, bone or both, with device 10 passing through an intervertebral foramen between two vertebrae. In other embodiments, other tissue in other areas of the body may be removed.

Figure 44A:
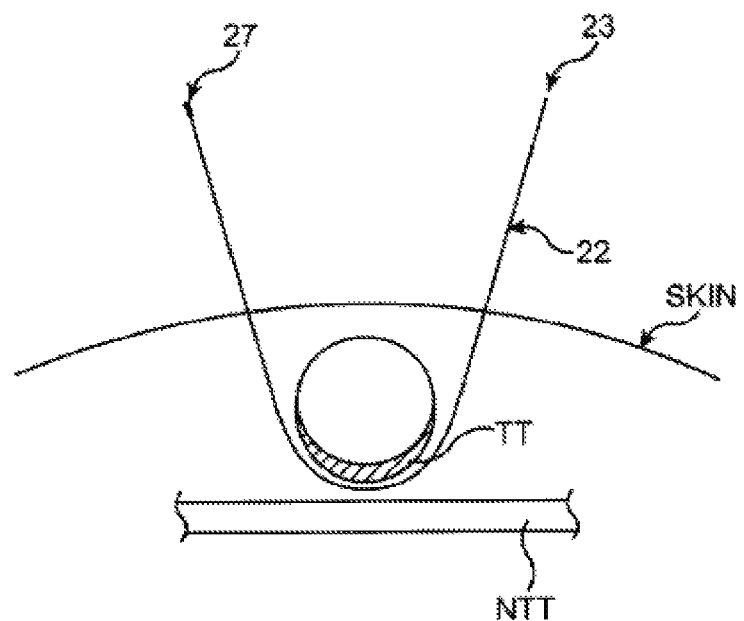
FIGS. 44A-E illustrates one variation of a tissue modification device being inserted into the tissue and manipulated to modify the tissue. Tools such as those shown in FIG. 43A-43F may be used for this procedure.

As shown in FIG. 44A, guidewire 22 with sharp tip 23 and shaped end 27 may be passed into the skin, between target and non-target tissue, and out of the skin. The guidewire may also be referred to a pullwire, since it is used to pull one or more devices into position, as described. Methods for passing guidewire/pullwire 22 are described further, for example, in U.S. patent application Ser. Nos. 11/457,416, 11/468,247 and 11/468,252, which were previously incorporated by reference. As described in those references, in various embodiments, guidewire 22 may be placed using a percutaneous method, such as with a needle, or using an open method, such as with a probe. In some embodiments, localization of neural tissue, such as with nerve stimulation on a guidewire passing probe or guidewire passing guide member may be used, to confirm that guidewire 22 is passed between target and non-target tissue. For example, a neural localization device (as shown in FIG. 43C, above) may be used by pulling into position using the guidewire/pullwire.

In some embodiments where the method is performed in the spine, one or more substances or devices may be placed into the epidural space of the spine before or after placing guidewire 22, to create additional space between target tissues, such as ligamentum flavum, and non-target tissues, such as cauda equina and nerve root. Substances may include, for example, any of a number of fluids or gels, such as radiographic contrast medium. Devices may include, for example, a barrier or shield device. Injection of substances into the epidural space to create a safety zone is described in U.S. patent application Ser. No. 11/193,557 (Pub. No. 2006/0036211), titled "Spinal Ligament Modification Kit," assigned to X-Sten, Inc., and filed Jul. 29, 2005, the full disclosure of which is hereby incorporated by reference. Various barrier devices for placement in the spine are described, for example, in U.S. patent application Ser. No. 11/405,859, titled "Tissue Modification Barrier Devices and Methods," and filed Apr. 17, 2005, the full disclosure of which is hereby incorporated by reference.

Figure 44B:
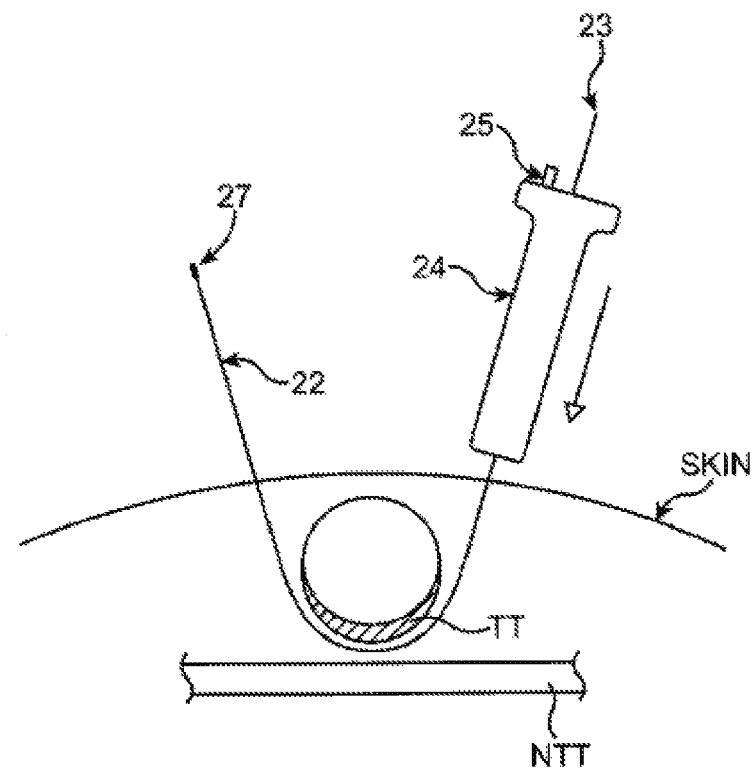

Referring to FIG. 44B, distal handle 24 (another variation of which is shown in FIG. 43E) may be passed over sharp tip 23 and tightened around guidewire 22, such as by moving tightening lever 25. In some variations, the handle captures or otherwise holds the sharp distal tip, to prevent injury or interference. Distal handle 24 may be coupled with guidewire 22 at this point in the process or at a later point, according to various embodiments.

Figure 44C:
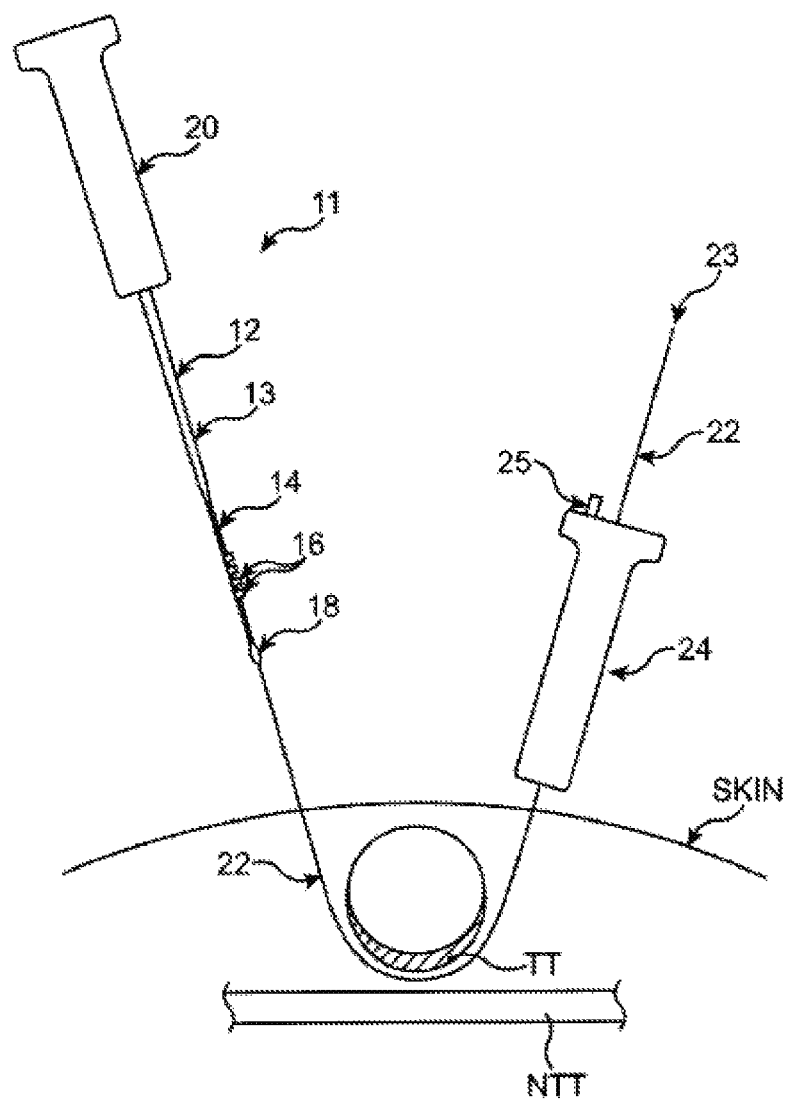

As shown in FIG. 44C, guidewire 22 may next be coupled with proximal device portion 11, by coupling shaped guidewire end 27 (not visible) with guidewire coupler 18. In the embodiment shown, for example, guidewire shaped end 27 may be placed into coupling member 18 (hollow-tipped arrow).

Figure 44D:
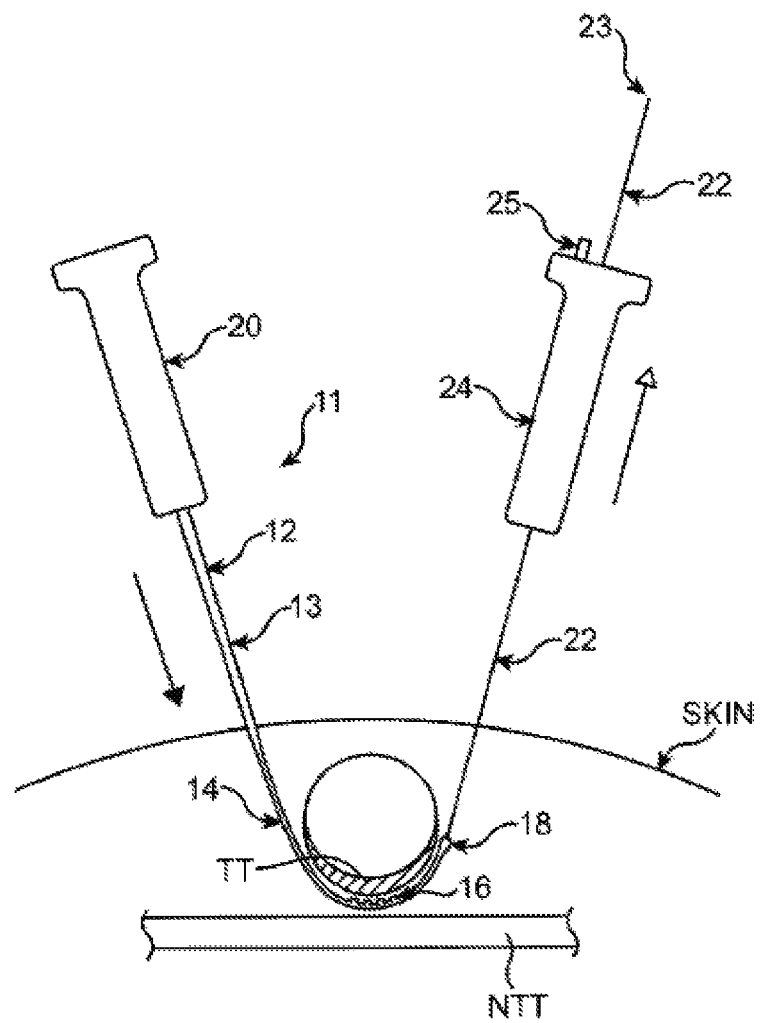

Referring to FIG. 44D, distal handle 24 may then be pulled (hollow-tipped arrow) to pull device 10 into the patient and to thus position tissue modifying members 16 in contact with target tissue TT. In some embodiments, such as when device 10 is used in a spinal procedure and passes through an intervertebral foramen, a surgeon or other physician user may use tactile feedback of device 10 passing into the foramen, such as when coupling member 18 and/or tissue modifying members 16 pass into the foramen, to determine when tissue modifying members 16 are positioned in a desired location relative to target tissue TT. Alternatively or additionally, a surgeon may confirm that a desired placement has been achieved by using radiographic imaging, such as fluoroscopy, direct visualization, such as in an open surgical case, or a combination of multiple methods.

In some embodiments in which device 10 is used in the spine to treat spinal stenosis and/or neural or neurovascular impingement, device 10 may be passed into the patient and to a position for modifying tissue without removing any vertebral bone. More specifically, in some embodiments, device 10 may be advanced into the patient, through an intervertebral foramen, and out of the patient without removing bone. This is contrary to the majority of current surgical methods for treating spinal stenosis, which typically include removal of at least some vertebral bone, such as performing a laminotomy or laminectomy, and which often remove significant amounts of vertebral lamina, spinous process, facet and/or pedicle bony tissue, simply to access the surgical site. In one embodiment, for example, device 10 may be advanced percutaneously into the patient, used to remove ligamentum flavum only, and withdrawn from the patient, without removing any vertebral bone.

Figure 44E:
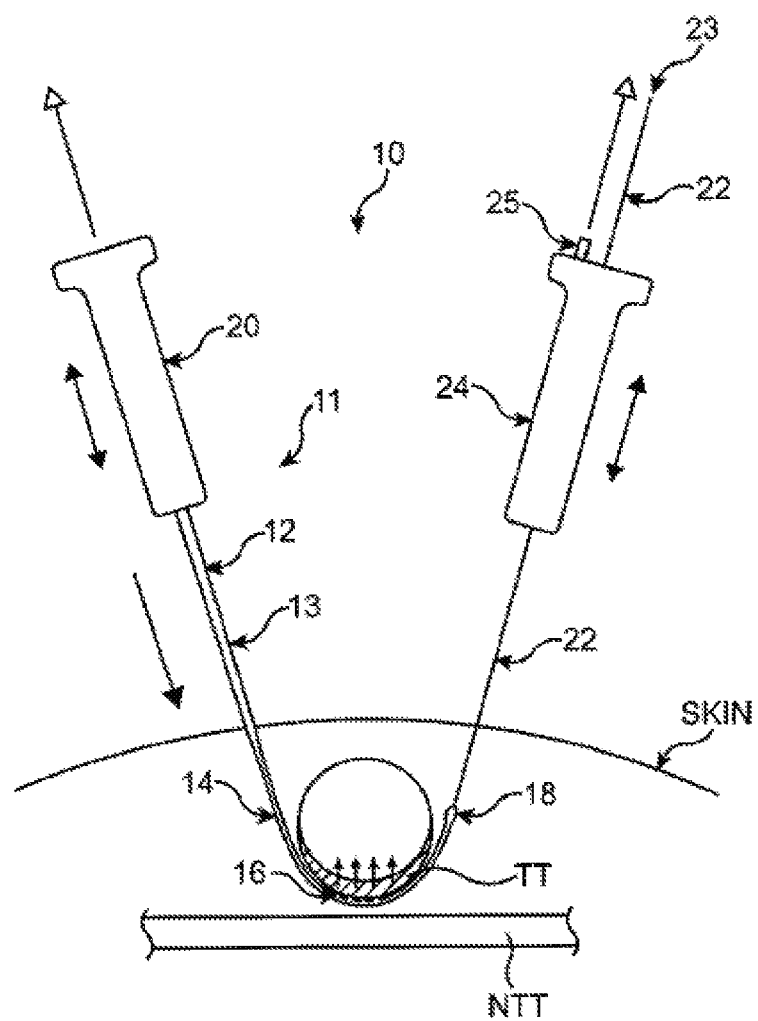

As shown in FIG. 44E, once tissue modifying members 16 (e.g., rungs including tissue modification surfaces, as described above) are positioned as desired, relative to target tissue IT, proximal handle 20 and guidewire handle 24 may be pulled (hollow-tipped arrows) to urge tissue modifying members 16 against target tissue TT (solid-tipped, single-headed arrows). While maintaining pulling/tensioning force, handles 20, 24 may be used to reciprocate device 10 back and forth (solid-tipped, double-headed arrows) to remove target tissue TT. In some variations, the tissue modification device includes a rigid (or semi-rigid or rigidifiable) proximal shaft portion 13 that may be used to help steer device 10, or more specifically flexible distal shaft portion 114, relative to the target TT. For example, a rigid shaft portion 113 may be used to move flexible portion 14 laterally or to pivot shaft 12 about an axis located along flexible portion 14. In one embodiment, for example, rigid portion 13 may be used to manipulate flexible portion 14 within an intervertebral foramen, such as by pivoting shaft 12 or moving flexible portion 14 laterally in a caudal and/or cephalad direction, relative to the patient. The rigidity of rigid proximal shaft portion 13 may generally facilitate such steering, as compared to a completely flexible device.

When a desired amount of tissue is removed, device 10 may be removed from the patient, such as by detaching guidewire handle 24 from guidewire 22 and pulling proximal handle 20 to withdraw device 10 and guidewire 22 out of the patient. In some embodiments, device 10 or an additional device may be reinserted into the patient and used in a second location to remove additional tissue. For example, in a spinal stenosis treatment procedure, device 10 may be used to remove tissue from (and thus decompress) a first intervertebral foramen and then my be removed and reinserted to remove tissue from a second foramen. This process may be repeated to remove tissue from any number of foramina. In one embodiment, device 10 may include a guidewire lumen, so that a guidewire may be placed into a second foramen while device 10 is in the epidural space of the patient. Device 10 may then be removed along with the first guidewire 22, attached to the second guidewire, and reinserted into the second foramen to remove tissue. In some embodiments, tissue may be removed from device 10 before reinserting device 10 into the patient to remove more tissue.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What is claimed is:

1. A flexible tissue-modification device for removing tissue from a patient, the device having an elongate body with an axial length, a width and a thickness, wherein the axial length is greater than the width and the width is greater than the thickness, the device comprising:
    a flexible connector extending longitudinally along the axial length of the elongate body;
    a plurality of rigid tissue-cutting rungs that are flexibly connected by the connector, wherein each rung in the plurality of tissue-cutting rungs extends at least partially across the width of the elongate body;
    at least one cutting edge on each of the tissue-cutting rungs;
    a plurality of spacers, wherein each rung in the plurality of tissue-cutting rungs is separated from an adjacent rung by a spacer, wherein the spacer forms an opening though the device between adjacent rungs that extends across the width of the elongate body; and
    a guidewire coupler attached to the connector at a distal end of the device, wherein the guidewire coupler includes a tapered distal end region that is configured to fit an enlarged proximal end of a guidewire so that the guidewire engages with the guidewire coupler when pulled distally.

2. The device of claim 1, wherein the plurality of tissue-cutting rungs comprises rungs having different configurations or sizes.

3. The device of claim 1, wherein the connector comprises at least one cable.

4. The device of claim 1, further comprising at least one protective side guard extending along the axial length of the elongate body.

5. The device of claim 1, wherein the cutting edge projects from a surface of the rung.

6. The device of claim 1, further comprising a tissue collection region in communication with the rung.

7. The device of claim 1, wherein the opening through the device is configured to provide a passage between adjacent rungs.

8. The device of claim 1, wherein the spacer is a ferrule.

9. The device of claim 1, wherein the plurality of rigid tissue-cutting rungs and the plurality of spacers are threaded on the connector.

10. A flexible tissue-modification device for removing tissue from a patient, the device having an elongate body with an axial length, a width and a thickness, wherein the axial length is greater than the width and the width is greater than the thickness, the device having an anterior, tissue-facing surface, the device comprising:
    a proximal handle;
    a flexible connector extending longitudinally along the axial length of the device from the handle;
    a first set of rigid tissue-cutting rungs that are flexibly connected to the connector, wherein the first set of tissue-cutting rungs include at least one first cutting edge projecting from the anterior surface of and positioned between lateral edges of each rung of the first set of rigid tissue-cutting rungs and each first cutting edge extends substantially perpendicular to the axial length;
    a second set of rigid tissue-cutting rungs that are flexibly connected to the connector, wherein the second set of tissue-cutting rungs include at least one second cutting edge projecting from the anterior surface of and extending along the axial length of a lateral edge of each rung of the second set of rigid tissue-cutting rungs, each second cutting edge extending substantially along the axial length; and
    a guidewire coupler attached to the connector at a distal end of the device.

11. The device of claim 10, wherein each second cutting edge is sized and configured to cut a strip of soft tissue.

12. The device of claim 11, wherein each second cutting edge includes a tombstone shaped edge.

13. The device of claim 11, wherein the soft tissue is ligamentum flavum.

14. The device of claim 1, further comprising a proximal handle attached to the connector.

15. The device of claim 1, wherein the connector comprises at least two flexible elongate cables, wherein the cables extend substantially adjacent to each other from a proximal end region of the device to a distal end region of the device.

16. The device of claim 1, wherein the plurality of rigid, tissue-cutting rungs are I-shaped such that the spacer is integral with the rung.

17. A flexible tissue-modification device for removing tissue from a patient, the device having an elongate body with an axial length, a width and a thickness, wherein the axial length is greater than the width and the width is greater than the thickness, the device comprising:
    a flexible connector comprising two lengths of cable extending adjacently along the axial length of the device;
    a plurality of rigid, tissue-cutting rungs that are connected to the lengths of cable, wherein each rung extends at least partially across the width of the body between the two lengths of cable and is separated from adjacent rungs by a spacer forming an opening though the device between adjacent rungs;
    a cutting edge on each of the tissue-cutting rungs; and
    a guidewire coupler attached to the connector at a distal end of the device, wherein the guidewire coupler includes a tapered distal end region that is configured to fit an enlarged proximal end of a guidewire so that the guidewire engages with the guidewire coupler when pulled distally.

18. The device of claim 17, wherein the spacer is integral with the rung.

19. The device of claim 17, wherein the spacer is separate from the rung and positioned between adjacent rungs.

* * * * *